(12) United States Patent
Rikihisa et al.

(10) Patent No.: US 6,893,640 B2
(45) Date of Patent: May 17, 2005

(54) **OUTER MEMBRANE PROTEIN OF *EHRLICHIA CANIS* AND *EHRLICHIA CHAFFEENSIS***

(75) Inventors: Yasuko Rikihisa, Worthington, OH (US); Norio Ohashi, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/314,639

(22) Filed: Dec. 9, 2002

(65) Prior Publication Data

US 2003/0103991 A1 Jun. 5, 2003

Related U.S. Application Data

(62) Division of application No. 09/314,701, filed on May 19, 1999, now Pat. No. 6,544,517.
(60) Provisional application No. 60/100,853, filed on Sep. 18, 1998.
(51) Int. Cl.$^7$ .................. A91K 39/00; A91K 39/38; A91K 39/02
(52) U.S. Cl. ................. 424/184.1; 424/185.1; 424/190.1; 424/191.1; 424/234.1; 435/243; 530/300; 530/350; 536/23.7; 536/23.32; 536/23.33
(58) Field of Search .................. 424/184.1, 185.1, 424/190.1, 191.1, 234.1; 435/243; 530/300, 350; 536/23.7, 23.32, 23.33

(56) References Cited

U.S. PATENT DOCUMENTS

| | | |
|---|---|---|
| 5,401,656 A | 3/1995 | Dawson |
| 5,413,931 A | 5/1995 | Dawson et al. |
| 5,789,176 A | 5/1995 | Dawson et al. |
| 5,869,335 A | 2/1999 | Munderloh et al. |
| 6,025,338 A | 2/2000 | Barbet et al. |
| 6,544,517 B1 | 4/2003 | Rikihisa et al. |

FOREIGN PATENT DOCUMENTS

WO 98/16554 4/1998

OTHER PUBLICATIONS

"Transcriptional Analysis of p30 Major Outer Membrane Multigene Family of *Ehrlichia canis* in Dogs, Ticks, and Cell Celture at Different Temperatures" by Unver et al., *Infection and Immunity*, vol. 69, No. 10, Oct. 2001, pp. 6172–6178.

"Transcriptional Analysis of p30 Major Outer Membrane Protein Genes of *Ehrlichia canis* in Naturally Infected Ticks and Sequence Analysis of p30–10 of *E. canis* from Diverse Geographic Regions" by Felek et al., *Journal of Clinical Microbiology*. vol. 41, No. 2, Feb. 2003. pp. 886–888.

"Cloning and Characterization of Multigenes Encoding the Immunodominant 30–Kilodalton Major Outer Membrane Proteins of *Ehrlichia Canis* and Application of the Recombinant Protein for Serodiagnosis" by Ohashi, et al., *Journal of Clinical Microbiology*, vol. 36, No. 9, Sep. 1998, pp. 2671–2680.

"Immunodominant Major Outer Membrane Protein of *Ehrlichia chaffeensis* Are Encoded by a Polymorphic Multigene Family" by Ohashi, et al., *Infection and Immunity*, vol. 66, No. 1, Jan. 1998, pp. 132–139.

Abstract D–79, "Binding of Outer Membrane Proteins of *Ehrlichia chaffeenis* to DHB2 Cells" by Zhang et al., 97th General Meeting of the American Society for Microbiology, Miami Beach, Florida, May 4–8, 199.

Abstract D–80, "Immunoprotective 28–kDa outer membrane protein of *Ehrlichia chaffeensis* is a member Of multi–sized protein antigen family" by Ohashi, et al., 97th General Meeting of the American Society for Microbiology, Miami Beach. Florida, May 408, 1997.

Abstract D–28, "Cloning, Sequencing, and Overexpression of *Ehrlichia Canis* Immunoreactive Protein Gene Homologous to Members of *Ehrlichia Chaffeensis* omp–1 Gene Family" by Ohashi, et al., 98th General Meeting of the American Society for Microbiology, May 17–2, 1998, Atlanta, Georgia.

Abstract D–29, "Dot Immunoblot Assay for Crime Ehrlichiosis: Using Recombinant Major Protein Antigen of *Ehrlichia Canis*" by Unver, et al., 98th General Meeting of the American Society for Microbiology, May 17–21, 1998, Atlanta, Georgia.

GenBank Accession AF078553, Oct. 27, 1998.
GenBank Accession AF078554, Oct. 27, 1998.
GenBank Accession AF078555, Oct. 27, 1998.
GenBank Accession AF021338, Feb. 19, 1998.
GenBank Accession U72291, Feb. 19, 1998.

(Continued)

*Primary Examiner*—Rodney P Swartz
(74) *Attorney, Agent, or Firm*—Calfee, Halter & Griswold, LLP

(57) ABSTRACT

Diagnostic tools for for serodiagnosing ehrlichiosis in mammals, particularly in members of the Canidae family and in humans are provided. The diagnostic tools are a group of outer membrane proteins of *E. chaffeensis* and variants thereof, referred to hereinafter as the "OMP proteins", a group of outer membrane proteins of *E. canis* and variants thereof referred to hereinafter as the "P30F proteins", and antibodies to the OMP proteins and the P30F proteins. The OMP proteins of *E. chaffeensis* encompass OMP-1, OMP-1A, OMP1-B, OMP-1C, OMP1-D, OMP1-E, OMP1-F, OMP1-H, OMP-1R, OMP-1S, OMP-1T, OMP-1U, OMP-1V, OMP-1W, OMP-1X, OMP-1Y and OMP-1Z. The P30F proteins of *E. canis* encompass P30, P30a, P30-1, P30-2, P30-3, P30-4, P30-5, P30-6, P30-7, P30-8, P30-9, P30-10, P30-11, and P30-12. Isolated polynucleotides that encode the *E. chaffeensis* OMP proteins and isolated polynucleotides that encode the *E. canis* P30F protein are also provided. The present invention also relates to kits containing reagents for diagnosing human ehrlichiosis and canine ehrlichiosis, and to immunogenic compositions containing one or more OMP proteins or P30F proteins.

2 Claims, 35 Drawing Sheets

OTHER PUBLICATIONS

GenBank Accession L01987, Mar. 17, 1994.
GenBank Accession X74250, Oct. 10, 1994.
GenBank Accession U07862, Jan. 5, 1995.
GenBank Accession U36193, Aug. 8, 1996.
GenBank Accession U50830, Jul. 15, 1996.
GenBank Accession U50831, Jul. 15, 1996.
GenBank Accession U50832, Jul. 15, 1996.
GenBank Accession U50833, Jul. 15, 1996.
GenBank Accession U50834, Jul. 15, 1996.
GenBank Accession U50835, Jul. 15, 1996.
GenBank Accession AF062761, Jul. 19, 1998.
GenBank Accession AF068234, Jun. 8, 1998.
GenBank Accession AF077732, Aug. 13, 1998.
GenBank Accession AF077733, Aug. 13, 1998.
GenBank Accession AF077734, Aug. 13, 1998.
GenBank Accession AF077735, Aug. 13, 1998.
GenBank Accession AF082745, Oct. 20, 1998.
GenBank Accession AF082746, Oct. 20, 1998.
GenBank Accession AF082747, Oct. 20, 1998.
GenBank Accession AF082748, Oct. 20, 1998.
GenBank Accession AF082749, Oct. 20, 1998.
GenBank Accession AF082750, Oct. 20, 1998.
"Molecular Characterization of a 28 kDa Surface Antigen Family of the Tribe Ehrlichiae" by G. Reddy, et al. *Biochemical and Biophysical Research Communications*, vol. 247, No. 3, 1998, pp. 636–643.
"Sequence Heterogeneity of the Major Antigen Protein 1 Genes from *Cowdria ruminantium* Isolates from Different Geographical Areas" by G. Reddy, et al., *Clinical and Diagnostic Laboratory Immunology*, vol. 3, No. 4, Jul. 1996, pp. 417–422.
"Derivation of the complete *msp4* gene sequence of *Anaplasma marginale* without cloning" by Oberle, et al., *Gene*, vol. 136, Dec. 1993, pp. 291–294.
"Molecular Cloning, Sequence Analysis and Expression of the Gene Encoding the Immunodominant 32–Kilodalton Protein of *Cowdria ruminantium*" by van Vliet, et al., *Infection and Immunity*, vol. 62, No. 4, Apr. 1994, pp. 1451–1456.
"Sequence and characterization of an *Ehrlichia chaffeensis* gene encoding 314 amino acids highly homologous to the NAD A enzyme" by Yu, et al., *FEMS Microbiol Lett*, Sep. 1, 1997, 154 (1), pp. 53–58.
"E: Enzyme–Linked Immunosorbent Assay and Western Immunoblot Analyses of *Ehrlichia Canis* and a Canine Granulocytic *Ehrlichia* Infection" by Rikihisa, et al., *Journal of Clinical Microbiology*, vol. 20, No. 2, Jan. 1992, pp. 143–148.
"Serological evidence for antigenic relationships between *Ehrlichia canis* and *Cowdria ruminatium*" by Kelly, et al., *Res Vet Sci*, 56 (2), Mar. 1994, pp. 170–174.
"The interface between research and the diagnoses of an emerging tick–borne disease, human ehrlichiosis due to *Ehrichia chaffensis*" by Dawson, et al., *Archives of Journal of Medicine*, vol. 156, No. 2, Jan. 22, 1996, pp. 137 (6).
"Western Immunoblotting analysis of the antibody responses of patients with human monocytotropic *ehrlichiosis* to different strains of *Ehrlichia chaffeensis* and *Ehrlichia canis*" by Chen, et al., *Clin Diagn Lab Immunol*, Nov. 1997, 4 (6), pp. 731–735.

"Analysis and untrastructural localization of *Ehrlichia chafeensis* proteins with monoclonal antibodies" by Chen, et al, *The American Journal of Tropical Medicine and Hygiene*, 1996, 54 (4) pp. 405–412.
"Identification of the antigenic constituents of *Ehrlichia chaffeensis*" by Chen, et al., *Am J Trp Med Hyg* Jan. 1994, 50 (1) pp. 52–58.
"Antigenic characterization of *ehrlichiae*: a protein immunoblotting of *Ehrlichia canis, Ehrlichia sennetsu,* and *Ehrlichia risticii*" by Brouqui, et al., *J Clin Microbiol*, May 1992, 30 (5) pp. 1062–1066.
"Serologic diagnosis of human monocytic *ehrlichiosis* by immunoblot analysis" by Brouqui, et al., *Clin Diagn Lab Immunol*, Nov. 1994, 1(6) pp. 645–649.
Abstract D/B–126, "Characterization of *p30* Multigene Family of *Ehrlichia canis*" by Ohashi, et al., Ninety–ninth General Meeting of the American Society for Microbiology, May 30–Jun. 3, 1999, Chicago, Illinois, p. 233.
Abstract D/B–138, "Western and Dot Blotting Analysis of *Ehrlichia chaffeensi*–IFA Positive and –Negative Human Sera Using Native and Recombinant *E. chaffeensis* and *E. canis* Antigen" by Unver, et al., Ninety–ninth General Meeting of the American Society for Microbiology, May 30–Jun. 3, 1999, Chicago, Illinois, p. 236.
"Molecular Cloning of the Gene for a Conserved Major Innumoreactive 28–Kilodalton Protein of *Ehrlichia canis*: a Potential Serodiagnostic Antigen" by McBride, et al., *Clinical and Diagnostic Laboratory Immunology*, vol. 6, No. 3, May 1999, pp. 392–399.
"The *mag1* Gene of *Cowdria ruminantium* is a Member of a Multigene Family Containing Both Conserved and Variable Genes" by Sulsona, et al., *Biochemical and Biophysical Research Communications*, 257, 300–305 (1999).
"Comparison of *Ehrlichia chaffeensis* Recombinant Proteins for Serologic Diagnosis of Human Monocytotropic *Ehrlichiosis*" by Yu, et al., *Journal of Clinical Microbiology*, vol. 37, No. 8, Aug. 1999, pp. 2568–2575.
"Genetic Diversity of the 28–Kilodalton Outer Membrane Protein Gene in Human Isolates of *Ehrlichia chaffeensis*" by Yu, et al., *Journal of Clinical Microbiology*, vol. 37, No. 4, Apr. 1999, pp. 1137–1143.
"Molecular characterization of a new 28–kilodalton protein gene and a multigene locus encoding five homologous 28–kilodalton immunodominant outer membrane proteins of*Ehrlichia canis*" by McBride, et al., *Rickettsiae and rickettsial diseases at the turn of thethird millenium*, D. Raoult, P. Brouqui, eds., Elsevier, Paris, Jun. 1999, pp. 43–47.
"Characterization of the genus–common outer membrane proteins in *Ehrlichia*" Yu, et al., *Rickettsiae and rickettsial diseases at the turn of the third millenium*, D. Raoult, P. Brouqui, eds., Elsevier, Paris, Jun. 1999, pp. 103–107.
GenBank Accession No. AF125279.
GenBank Accession No. AF125278.
GenBank Accession No. AF125277.
GenBank Accession No. AF125276.
GenBank Accession No. AF125275.
GenBank Accession No. AF125274.

```
                                                              GGCATAAATGGGAATTTCTACATCAGTGGAAAATACATGCCAAGTGCTTCGCATTTTGGA     60
                                                                       ←─────── FECH1 primer
                                                                D  P  A  G  S  G  I  N  G  N  F  Y  I  S  G  K  Y  M  P  S  A  S  H  F  G    25
GTATTCTCTGCTAAGGAAGAAAGAAATACAACAGTTGGAGTGTTTGGACTGAAGCAAAATTGGGACGGAAGCGCAATATCCAACTCCTCC    150
 V  F  S  A  K  E  E  R  N  T  T  V  G  V  F  G  L  K  Q  N  W  D  G  S  A  I  S  N  S  S     55
CCAAACGATGTATTCACTGTCTCAAATTTATTCATTTAAATATGAAAACAACCCGTTTTTAGGTTTTGCAGGAGCTATTGGTTACTCAATG    240
 P  N  D  V  F  T  V  S  N  Y  S  F  K  Y  E  N  N  P  F  L  G  F  A  G  A  I  G  Y  S  M    85
GATGGTCCAAGAATAGAGCTTGAAGTATCTTATGAAACATTTGATGTAAAAATCAAGGTAACAATTATAAGAACACATAGATAT    330
 D  G  P  R  I  E  L  E  V  S  Y  E  T  F  D  V  K  N  Q  G  N  N  Y  K  N  E  A  H  R  Y    115
TGTGCTCTATCCCATAACTCAGCAGCAGACATGAGTAGTGCAAGTAATGAAGGCCATATACCTTTCTCTAAAAATGAAGGATTACTTGACATATCA    420
 C  A  L  S  H  N  S  A  A  D  M  S  S  A  S  N  E  G  H  I  P  F  S  K  N  E  G  L  L  D  I  S    145
TTTATGCTGAACGCTACAAATCCTAAATTCTTACCAAGAAAGTTAGGTTTAAGCTACTCTATAAGCCCAGAAGCTTCTGTGTTTATTGGT    510
 F  M  L  N  A  C  Y  D  D  V  V  G  E  G  I  P  F  S  P  Y  I  C  A  G  I  G  T  D  L  V  S    175
ATGTTTGAAGCTACAAATCCTAAATTCTTACCAAGAAAGTTAGGTTTAAGCTACTCTATAAGCCCAGAAGCTTCTGTGTTTATTGGT    600
 M  F  E  A  T  N  P  K  I  S  Y  Q  G  K  L  G  L  S  Y  S  I  S  P  E  A  S  V  F  I  G    205
GGGCACTTTCATAAGGTAATAGGGAACGAATTTAGAGATATTCCTACTATAATACCTACTGGATCAACACTTGCAGGAAAAGGAAAGTAC    690
 G  H  F  H  K  V  I  G  N  E  F  R  D  I  P  T  I  P  T  G  S  T  L  A  G  K  G  N  Y    235
CCTGCAATAGTAATACTGGATGTATGCCACTTTGGAATAGAACTTGGAGGAAGGTTTGCTTTCTAA    756
 P  A  I  V  I  L  D  V  C  H  F  G  I  E  L  G  G  R  F  A  F  *    256
                                       ─────── RECH2 primer
```

Fig. 1

```
         10         20         30         40         50         60
ATGAATTACA AAAAAGTTTT CATAACAAGT GCATTGATAT CATTAATATC TTCTCTACCT
         70         80         90        100        110        120
GGAGTATCAT TTTCCGACCC AGCAGGTAGT GGTATTAACG GTAATTTCTA CATCAGTGGA
        130        140        150        160        170        180
AAATACATGC CAAGTGCTTC GCATTTGGA GTATTCTCTG CTAAGGAAGA AAGAAATACA
        190        200        210        220        230        240
ACAGTTGGAG TGTTTGGACT GAAGCAAAAT TGGGACGGAA GCGCAATATC CAACTCCTCC
        250        260        270        280        290        300
CCAAACGATG TATTCACTGT CTCAAATTAT TCATTTAAAT ATGAAAACAA CCCGTTTTTA
        310        320        330        340        350        360
GGTTTTGCAG GAGCTATTGG TTACTCAATG GATGGTCCAA GAATAGAGCT TGAAGTATCT
        370        380        390        400        410        420
TATGAAACAT TTGATGTAAA AAATCAAGGT AACAATTATA AGAATGAAGC ACATAGATAT
        430        440        450        460        470        480
TGTGCTCTAT CCCATAACTC AGCAGCAGAC ATGAGTAGTG CAAGTAATAA TTTTGTCTTT
        490        500        510        520        530        540
CTAAAAAATG AAGGATTACT TGACATATCA TTTATGCTGA ACGCATGCTA TGACGTAGTA
        550        560        570        580        590        600
GGCGAAGGCA TACCTTTTTC TCCTTATATA TGCGCAGGTA TCGGTACTGA TTTAGTATCC
        610        620        630        640        650        660
ATGTTTGAAG CTACAAATCC TAAAATTTCT TACCAAGGAA AGTTAGGTTT AAGCTACTCT
        670        680        690        700        710        720
ATAAGCCCAG AAGCTTCTGT GTTTATTGGT GGGCACTTTC ATAAGGTAAT AGGGAACGAA
        730        740        750        760        770        780
TTTAGAGATA TTCCTACTAT AATACCTACT GGATCAACAC TTGCAGGAAA AGGAAACTAC
        790        800        810        820        830        840
CCTGCAATAG TAATACTGGA TGTATGCCAC TTTGGAATAG AACTTGGAGG AAGGTTTGCT
        850        860        870        880        890        900
TTCTAA....  .........  .........  .........  .........  .........
```

Fig. 3A

```
         10         20         30         40         50         60
MNYKKVFITS ALISLISSLP GVSFSDPAGS GINGNFYISG KYMPSASHFG VFSAKEERNT
         70         80         90        100        110        120
TVGVFGLKQN WDGSAISNSS PNDVFTVSNY SFKYENNPFL GFAGAIGYSM DGPRIELEVS
        130        140        150        160        170        180
YETFDVKNQG NNYKNEAHRY CALSHNSAAD MSSASNNFVF LKNEGLLDIS FMLNACYDVV
        190        200        210        220        230        240
GEGIPFSPYI CAGIGTDLVS MFEATNPKIS YQGKLGLSYS ISPEASVFIG GHFHKVIGNE
        250        260        270        280        290        300
FRDIPTIIPT GSTLAGKGNY PAIVILDVCH FGIELGGRFA F.........  .........
```

Fig. 3B

|      10    |     20     |     30     |     40     |     50     |     60     |
|------------|------------|------------|------------|------------|------------|
| ATGAATTACA | AGAAAATTTT | TGTAAGCAGT | GCATTAATTT | CATTAATGTC | AATCTTACCT |
|      70    |     80     |     90     |    100     |    110     |    120     |
| TACCAATCTT | TTGCAGATCC | TGTAACTTCA | AATGATACAG | GAATCAACGA | CAGCAGAGAA |
|     130    |    140     |    150     |    160     |    170     |    180     |
| GGCTTCTACA | TTAGTGTAAA | GTATAATCCA | AGCATATCAC | ACTTCAGAAA | ATTCTCAGCT |
|     190    |    200     |    210     |    220     |    230     |    240     |
| GAAGAAGCTC | CCATCAATGG | AAATACTTCT | ATCACTAAAA | AGGTTTTCGG | GCTGAAAAAA |
|     250    |    260     |    270     |    280     |    290     |    300     |
| GACGGAGATA | TAGCACAATC | TGCGAATTTT | AACAGGACAG | ATCCAGCCCT | CGAGTTTCAG |
|     310    |    320     |    330     |    340     |    350     |    360     |
| AATAACCTAA | TATCAGGATT | CTCAGGAAGT | ATTGGTTATG | CTATGGATGG | GCCAAGAATA |
|     370    |    380     |    390     |    400     |    410     |    420     |
| GAACTTGAAG | CTGCATACCA | AAAATTTGAT | GCAAAAAATC | CTGACAACAA | TGACACTAAT |
|     430    |    440     |    450     |    460     |    470     |    480     |
| AGCGGTGACT | ACTATAAATA | CTTTGGACTA | TCTCGTGAAG | ACGCAATAGC | AGATAAGAAA |
|     490    |    500     |    510     |    520     |    530     |    540     |
| TATGTTGTCC | TTAAAAATGA | AGGCATCACT | TTTATGTCAT | TAATGGTTAA | CACTTGCTAT |
|     550    |    560     |    570     |    580     |    590     |    600     |
| GACATTACAG | CTGAAGGAGT | ACCTTTCATA | CCGTATGCAT | GTGCAGGTGT | AGGAGCAGAC |
|     610    |    620     |    630     |    640     |    650     |    660     |
| CTTATAAACG | TATTTAAGGA | TTTTAATTTA | AAATTCTCAT | ACCAAGGGAA | AATAGGTATT |
|     670    |    680     |    690     |    700     |    710     |    720     |
| AGCTATCCAA | TCACACCAGA | AGTTTCCGCT | TTTATTGGAG | GATACTACCA | CGGAGTTATA |
|     730    |    740     |    750     |    760     |    770     |    780     |
| GGAAATAATT | TTAACAAAAT | ACCTGTAATA | ACACCTGTAG | TATTAGAAGG | AGCTCCTCAA |
|     790    |    800     |    810     |    820     |    830     |    840     |
| ACCACATCTG | CGCTAGTAAC | TATTGACACT | GGATACTTTG | GCGGAGAAGT | TGGAGTAAGG |
|     850    |    860     |    870     |    880     |    890     |    900     |
| TTCACCTTCT | AG........ | .......... | .......... | .......... | .......... |

Fig. 4A

|      10    |     20     |     30     |     40     |     50     |     60     |
|------------|------------|------------|------------|------------|------------|
| MNYKKIFVSS | ALISLMSILP | YQSFADPVTS | NDTGINDSRE | GFYISVKYNP | SISHFRKFSA |
|      70    |     80     |     90     |    100     |    110     |    120     |
| EEAPINGNTS | ITKKVFGLKK | DGDIAQSANF | NRTDPALEFQ | NNLISGFSGS | IGYAMDGPRI |
|     130    |    140     |    150     |    160     |    170     |    180     |
| ELEAAYQKFD | AKNPDNNDTN | SGDYYKYFGL | SREDAIADKK | YVVLKNEGIT | FMSLMVNTCY |
|     190    |    200     |    210     |    220     |    230     |    240     |
| DITAEGVPFI | PYACAGVGAD | LINVFKDENL | KFSYQGKIGI | SYPITPEVSA | FIGGYYHGVI |
|     250    |    260     |    270     |    280     |    290     |    300     |
| GNNGNKIPVI | TPVVLEGAPQ | TTSALVTIDT | GYFGGEVGVR | FTF....... | .......... |

Fig. 4B

```
          10         20         30         40         50         60
 ATGAACTGCA AAAAATTTTT TATAACAACT GCATTGGCAT TGCCAATGTC TTTCTTACCT
          70         80         90        100        110        120
 GGAATATTAC TTTCTGAACC AGTACAAGAT GACAGTGTGA GTGGCAATTT CTATATTAGT
         130        140        150        160        170        180
 GGCAAGTACA TGCCAAGTGC TTCTCATTTT GGAGTTTTCT CTGCCAAAGA AGAAAAAAAT
         190        200        210        220        230        240
 CCTACTGTCG CGTTGTATGG TTTGAAACAA GATTGGAACG GTGTTAGTGC TTCAAGTCAT
         250        260        270        280        290        300
 GCTGATGCGG ACTTTAATAA CAAAGGTTAT TCTTTTAAAT ACGAAAACAA TCCATTTCTA
         310        320        330        340        350        360
 GGTTTTGCAG GAGCTATTGG TTATTCAATG GGTGGTCCAA GAATAGAGTT TGAAGTGTCC
         370        380        390        400        410        420
 TATGAAACAT TTGACGTGAA AAATCAAGGT GGTAATTACA AAAATGATGC TCACAGATAC
         430        440        450        460        470        480
 TGTGCCTTAG ATCGTAAAGC AAGCAGCACT AATGCCACAG CTAGTCACTA CGTGCTACTA
         490        500        510        520        530        540
 AAAAATGAAG GACTACTTGA TATATCACTT ATGTTGAATG CATGCTATGA CGTAGTAAGT
         550        560        570        580        590        600
 GAAGGAATAC CTTTCTCTCC TTACATATGT GCAGGTGTTG GTACCGATTT AATATCCATG
         610        620        630        640        650        660
 TTTGAAGCTA TAAACCCTAA AATTTCTTAT CAAGGAAAGT TAGGTTTGAG TTACTCTATA
         670        680        690        700        710        720
 AACCCAGAAG CTTCTGTCTT TGTTGGTGGA CATTTTCATA AAGTTGCAGG TAATGAATTC
         730        740        750        760        770        780
 AGGGACATTT CTACTCTTAA AGCGTTTGCT ACACCATCAT CTGCAGCTAC TCCAGACTTA
         790        800        810        820        830        840
 GCAACAGTAA CACTGAGTGT GTGTCACTTT GGAGTAGAAC TTGGAGGAAG ATTTAACTTC
         850        860        870        880        890        900
 TAA.......  .........  .........  .........  .........  .........
```

Fig. 5A

```
          10         20         30         40         50         60
 MNCKKFFITT ALALPMSFLP GILLSEPVQD DSVSGNFYIS GKYMPSASHF GVFSAKEEKN
          70         80         90        100        110        120
 PTVALYGLKQ DWNGVSASSH ADADFNNKGY SFKYENNPFL GFAGAIGYSM GGPRIEFEVS
         130        140        150        160        170        180
 YETFDVKNQG GNYKNDAHRY CALDRKASST NATASHYVLL KNEGLLDISL MLNACYDVVS
         190        200        210        220        230        240
 EGIPFSPYIC AGVGTDLISM FEAINPKISY QGKLGLSYSI NPEASVFVGG HFHKVAGNEF
         250        260        270        280        290        300
 RDISTLKAFA TPSSAATPDL ATVTLSVCHF GVELGGRFNF ..........  ..........
```

Fig. 5B

```
           10         20         30         40         50         60
    ATGAACTGCG AAAAATTTTT TATAACAACT GCATTAACAT TACTAATGTC CTTCTTACCT
           70         80         90        100        110        120
    GGAATATCAC TTTCTGATCC AGTACAGGAT GACAACATTA GTGGTAATTT CTACATCAGT
          130        140        150        160        170        180
    GGAAAGTATA TGCCAAGCGC TTCGCATTTT GGAGTTTTTT CTGCCAAGGA AGAAAGAAAT
          190        200        210        220        230        240
    ACAACAGTTG GAGTATTTGG AATAGAGCAA GATTGGGATA GATGTGTAAT ATCTAGAACC
          250        260        270        280        290        300
    ACTTTAAGCG ATATATTCAC CGTTCCAAAT TATTCATTTA AGTATGAAAA TAATCTATTT
          310        320        330        340        350        360
    TCAGGATTTG CAGGAGCTAT TGGCTACTCA ATGGATGGCC CAAGAATAGA GCTTGAAGTA
          370        380        390        400        410        420
    TCTTATGAAG CATTCGATGT TAAAAATCAA GGTAACAATT ATAAGAACGA AGCACATAGA
          430        440        450        460        470        480
    TATTATGCTC TGTCCCATCT TCTCGGCACA GAGACACAGA TAGATGGTGC AGGCAGTGCG
          490        500        510        520        530        540
    TCTGTCTTTC TAATAAATGA AGGACTACTT GATAAATCAT TTATGCTGAA CGCATGTTAT
          550        560        570        580        590        600
    GATGTAATAA GTGAAGGCAT ACCTTTTTCT CCTTATATAT GTGCAGGTAT TGGTATTGAT
          610        620        630        640        650        660
    TTAGTATCCA TGTTTGAAGC TATAAATCCT AAAATTTCTT ATCAAGGAAA ATTAGGCTTA
          670        680        690        700        710        720
    AGTTACCCTA TAAGCCCAGA AGCTTCTGTG TTTATTGGTG GACATTTTCA TAAGGTGATA
          730        740        750        760        770        780
    GGAAACGAAT TTAGAGATAT TCCTACTATG ATACCTAGTG AATCAGCGCT TGCAGGAAAA
          790        800        810        820        830        840
    GGAAACTACC CTGCAATAGT AACACTGGAC GTGTTCTACT TTGGCATAGA ACTTGGAGGA
          850        860        870        880        890        900
    AGGTTTAACT TCCAACTTTG A......... .......... .......... ..........
```

Fig. 6A

```
           10         20         30         40         50         60
    MNCEKFFITT ALTLLMSFLP GISLSDPVQD DNISGNFYIS GKYMPSASHF GVFSAKEERN
           70         80         90        100        110        120
    TTVGVFGIEQ DWDRCVISRT TLSDIFTVPN YSFKYENNLF SGFAGAIGYS MDGPRIELEV
          130        140        150        160        170        180
    SYEAFDVKNQ GNNYKNEAHR YYALSHLLGT ETQIDGAGSA SVFLINEGLL DKSFMLNACY
          190        200        210        220        230        240
    DVISEGIPFS PYICAGIGID LVSMFAEINP KISYQGKLGL SYPISPEASV FIGGHFHKVI
          250        260        270        280        290        300
    GNEFRDIPTM IPSESALAGK GNYPAIVTLD VFYFGIELGG RFNFQL.... ..........
```

Fig. 6B

```
        10         20         30         40         50         60
ATGAATTGCA AAAAATTTTT TATAACAACT GCATTAGTAT CACTAATGTC CTTTCTACCT
        70         80         90        100        110        120
GGAATATCAT TTTCTGATCC AGTGCAAGGT GACAATATTA GTGGTAATTT CTATGTTAGT
       130        140        150        160        170        180
GGCAAGTATA TGCCAAGTGC TTCGCATTTT GGCATGTTTT CTGCCAAAGA AGAAAAAAAT
       190        200        210        220        230        240
CCTACTGTTG CATTGTATGG CTTAAAACAA GATTGGGAAG GGATTAGCTC ATCAAGTCAC
       250        260        270        280        290        300
AATGATAATC ATTTCAATAA CAAGGGTTAT TCATTTAAAT ATGAAAATAA CCCATTTTTA
       310        320        330        340        350        360
GGGTTTGCAG GAGCTATTGG TTATTCAATG GGTGGTCCAA GAGTAGAGTT TGAAGTGTCC
       370        380        390        400        410        420
TATGAAACAT TTGACGTTAA AAATCAGGGT AATAACTATA AAAATGATGC TCACAGATAC
       430        440        450        460        470        480
TGTGCTTTAG GTCAACAAGA CAACAGCGGA ATACCTAAAA CTAGTAAATA CGTACTGTTA
       490        500        510        520        530        540
AAAAGCGAAG GATTGCTTGA CATATCATTT ATGCTAAATG CATGCTATGA TATAATAAAC
       550        560        570        580        590        600
GAGAGCATAC CTTTGTCTCC TTACATATGT GCAGGTGTTG GTACTGATTT AATATCCATG
       610        620        630        640        650        660
TTTGAAGCTA CAAATCCTAA AATTTCTTAC CAAGGGAAGT TAGGTCTAAG TTACTCTATA
       670        680        690        700        710        720
AACCCAGAAG CTTCTGTATT TATTGGTGGA CATTTTCATA AGGTGATAGG AAACGAATTT
       730        740        750        760        770        780
AGGGACATTC CTACTCTGAA AGCATTTGTT ACGTCATCAG CTACTCCAGA TCTAGCAATA
       790        800        810        820        830        840
GTAACACTAA GTGTATGTCA TTTTGGAATA GAACTTGGAG GAAGGTTTAA CTTCTAA...
```

Fig. 7A

```
        10         20         30         40         50         60
MNCKKFFITT ALVSLMSFLP GISFSDPVQG DNISGNFYVS GKYMPSASHF GMFSAKEEKN
        70         80         90        100        110        120
PTVALYGLKQ DWEGISSSSH NDNHFNNKGY SFKYENNPFL GFAGAIGYSM GGPRVEFEVS
       130        140        150        160        170        180
YETFDVKNQG NNYKNDAHRY CALGQQDNSG IPKTSKYVLL KSEGLLDISF MLNACYDIIN
       190        200        210        220        230        240
ESIPLSPYIC AGVGTDLISM FEATNPKISY QGKLGLSYSI NPEASVFIGG HFHKVIGNEF
       250        260        270        280        290        300
RDIPTLKAFV TSSATPDLAI VTLSVCHFGI ELGGRFNF.. .......... ..........
```

Fig. 7B

```
          10         20         30         40         50         60
   ATGAATTGCA AAAAATTTTT TATAACAACT ACATTAGTAT CGCTAATGTC CTTCTTACCT
          70         80         90        100        110        120
   GGAATATCAT TTTCTGATGC AGTACAGAAC GACAATGTTG GTGGTAATTT CTATATCAGT
         130        140        150        160        170        180
   GGGAAATATG TACCAAGTGT TCACATTTT  GGCGTATTCT CTGCTAAACA GGAAAGAAAT
         190        200        210        220        230        240
   ACAACAACCG GAGTATTTGG ATTAAAGCAA GATTGGGATG GCAGCACAAT ATCTAAAAAT
         250        260        270        280        290        300
   TCTCCAGAAA ATACATTTAA CGTTCCAAAT TATTCATTTA AATATGAAAA TAATCCATTT
         310        320        330        340        350        360
   CTAGGTTTTG CAGGAGCTGT TGGTTATTTA ATGAATGGTC CAAGAATAGA GTTAGAAATG
         370        380        390        400        410        420
   TCCTATGAAA CATTTGATGT GAAAAACCAG GGTAATAACT ATAAGAACGA TGCTCACAAA
         430        440        450        460        470        480
   TATTATGCTT TAACCCATAA CAGTGGGGGA AAGCTAAGCA ATGCAGGTGA TAAGTTTGTT
         490        500        510        520        530        540
   TTTCTAAAAA ATGAAGGACT ACTTGATATA TCACTTATGT TGAATGCATG CTATGATGTA
         550        560        570        580        590        600
   ATAAGTGAAG GAATACCTTT CTCTCCTTAC ATATGTGCAG GTGTTGGTAC TGATTTAATA
         610        620        630        640        650        660
   TCCATGTTTG AAGCTATAAA CCCTAAAATT TCTTATCAAG GAAAGTTAGG TTTGAGTTAC
         670        680        690        700        710        720
   TCCATAAGCC CAGAAGCTTC TGTTTTTGTT GGTGGACATT TTCATAAGGT GATAGGGAAT
         730        740        750        760        770        780
   GAATTCAGAG ATATTCCTGC TATGATACCC AGTACCTCAA CTCTCACAGG TAATCACTTT
         790        800        810        820        830        840
   ACTATAGTAA CACTAAGTGT ATGCCACTTT GGAGTGGAAC TTGGAGGAAG GTTTAACTTT
         850        860        870        880        890        900
   TAA.......  .......... .......... .......... .......... ..........
```

Fig. 8A

```
          10         20         30         40         50         60
   MNCKKFFITT TLVSLMSFLP GISFSDAVQN DNVGGNFYIS GKYVPSVSHF GVFSAKQERN
          70         80         90        100        110        120
   TTTGVFGLKQ DWDGSTISKN SPENTFNVPN YSFKYENNPF LGFAGAVGYL MNGPRIELEM
         130        140        150        160        170        180
   SYETFDVKNQ GNNYKNDAHK YYALTHNSGG KLSNAGDKFV FLKNEGLLDI SLMLNACYDV
         190        200        210        220        230        240
   ISEGIPFSPY ICAGVGTDLI SMFEAINPKI SYQGKLGLSY SISPEASVFV GGHFHKVIGN
         250        260        270        280        290        300
   EFRDIPAMIP STSTLTGNHF TIVTLSVSHF GVELGGRFNF .......... ..........
```

Fig. 8B

```
         10         20         30         40         50         60
ATGGAAAATC TCATGAATAA GAAAAACAAA TTCTTTACAA TAAGTACAGC AATGGTATGC
         70         80         90        100        110        120
TTATTGTTAT TACCTGGTAT ATCATTTTCA GAAACTATAA ACAACAGTGC TAAAAAACAG
        130        140        150        160        170        180
CCTGGGTTAT ATATCAGTGG GCAGTACAAA CCTAGTGTTT CAGTTTTTAG TAATTTTTCA
        190        200        210        220        230        240
GTAAAAGAAA CTAATGTTCC CACAAAGCAG TTAATAGCAC TTAAAAAAGA CATTAATTCT
        250        260        270        280        290        300
GTTGCAGTTG GTAGTAATGC TACTACAGGT ATTAGCAATC CAGGTAATTT CACAATTCCT
        310        320        330        340        350        360
TATACTGCAG AATTTCAAGA TAATGTTGCC AATTTCAATG GGGCTGTTGG TTACTCTTTT
        370        380        390        400        410        420
CCTGATAGTC TAAGAATTGA AATAGAGGGA TTTCATGAAA AATTTGATGT CAAAAACCCT
        430        440        450        460        470        480
GGAGGTTACA CACAAGTAAA AGATGCGTAC CGTTATTTTG CACTAGCACG TGATTTAAAA
        490        500        510        520        530        540
GATGGCTTCT TTGAACCTAA AGCGGAAGAT ACAGGTGTTT ATCATACTGT TATGAAAAAT
        550        560        570        580        590        600
GATGGATTAT CTATTTTATC TACTATGGTT AACGTCTGTT ACGATTTTTC TGTAGATGAA
        610        620        630        640        650        660
TTACCAGTCT TACCTTATAT ATGTGCAGGT ATGGGTATAA ACGCCATAGA ATTCTTCGAC
        670        680        690        700        710        720
GCTTTACATG TAAAATTTGC TTACCAAGGC AAACTAGGTA TTAGCTATCA ACTATTTACT
        730        740        750        760        770        780
AAAGTAAATT TATTCCTTGA TGGGTATTAC CATCAAGTAA TAGGCAATCA ATTCAAAAAC
        790        800        810        820        830        840
TTAAACGTAA ACCATGTTTA CACACTTAAA GAATCTCCTA AAGTCACATC TGCAGTAGCT
        850        860        870        880        890        900
ACACTTGACA TTGCATACTT TGGTGGCGAA GTTGGAATAA GATTCACATT TTAA......
```

Fig. 9A

```
         10         20         30         40         50         60
MENLMNKKNK FFTISTAMVC LLLLPGISFS ETINNSAKKQ PGLYISGQYK PSVSVFSNFS
         70         80         90        100        110        120
VKETNVPTKQ LIALKKDINS VAVGSNATTG ISNPGNFTIP YTAEFQDNVA NFNGAVGYSF
        130        140        150        160        170        180
PDSLRIEIEG FHEKFDVKNP GGYTQVKDAY RYFALARDLK DGFFEPKAED TGVYHTVMKN
        190        200        210        220        230        240
DGLSILSTMV NVCYDFSVDE LPVLPYICAG MGINAIEFED ALHVKFAYQG KLGISYQLFT
        250        260        270        280        290        300
KVNLFLDGYY HQVIGNQFKN LNVNHVYTLK ESPKVTSAVA TLDIAYFGGE VGIRFTF...
```

Fig. 9B

```
         10         20         30         40         50         60
ATGATATATA AAGAAAAACT TACTAGAGTG GGAGAATATA TCTTAGCATA TTTATCATTT
         70         80         90        100        110        120
ATTCTTTCTA CTTATATCTT TCTAGTGCTG GTAAATATTA TTAGATATAA CAGCCTTGCT
        130        140        150        160        170        180
ATATGTGTTA TCAGTCTACT AAGAACTAAT ATCTTTAACG TTAGCACAAA AAAATTAATA
        190        200        210        220        230        240
AAAGATAAAT GTCGTGATAC TAAGTTTAGT AACATGAATT GTTATTTGTA CGGTAAACCG
        250        260        270        280        290        300
TTAAATTTAC AAATTTTTTA TGGAATATTT TCCTTTATTA GAAACTTTCA AAATAACACA
        310        320        330        340        350        360
CTAATAATTC CTAATGATAG TAAATGCGGC TTCTATACCA CGTTATGGGA TAATCCAGCA
        370        380        390        400        410        420
CTACATTATA CATATACACT TACTGGCAGT GAGTACCGTA ATTTTTTGA CATTCTATAT
        430        440        450        460        470        480
GAAAACATTA TCTGTCAATG TAAATTACTT ATTAACTATA ACCGTTCTGT ATTAAACCAA
        490        500        510        520        530        540
CATAATAAAA ATACTCTCGT AATAATACCA ATACCTAATG CTAGAGAGTT CAGTAATGAA
        550        560        570        580        590        600
ATTCGAGTAA GGAATATATC AATAAATAAG GAAAGTTCTT ATGAGTGCTA A.........
```

Fig. 10A

```
         10         20         30         40         50         60
MIYKEKLTRV GEYILAYLSF ILSTYIFLVL VNIIRYNSLA ICVISLLRTN IFNVSTKKLI
         70         80         90        100        110        120
KDKCRDTKFS NMNCYLYGKP LNLQIFYGIF SFIRNFQNNT LIIPNDSKCG FYTTLWDNPA
        130        140        150        160        170        180
LHYTYTLTGS EYRNFEDILY ENIICQCKLL INYNRSVLNQ HNKNTLVIIP IPNAREFSNE
        190        200        210        220        230        240
IRVRNISINK ESSYEC.... .......... .......... .......... ..........
```

Fig. 10B

```
          10          20          30          40          50          60
ATGAATAAAA  AAAACAAGTT  TATTATAGCT  ACAGCATTGG  TATATTTACT  GTCATTACCT
          70          80          90         100         110         120
AGTGTATCGT  TTTCAGAGGT  TACAAACAGC  AGTATTAAAA  AACACTCTGG  GTTATATATT
         130         140         150         160         170         180
AGTGGACAAT  ACAAACCAAG  TGTTTCTGTT  TTTAGTAGTT  TCTCAATTAA  AGAAACTAAC
         190         200         210         220         230         240
ACTATCACAA  AAAATCTTAT  AGCGTTAAAA  AAAGATATTA  ACTCTCTTGA  AGTTAACGCC
         250         260         270         280         290         300
GATGCTAGTC  AAGGTATTAG  TCATCCAGGA  AATTTTACTA  TACCTTATAT  AGCAGCATTT
         310         320         330         340         350         360
GAAGATAATG  CTTTTAATTT  CAACGGTGCT  ATTGGTTACA  TTACTGAAGG  TCTAAGGATT
         370         380         390         400         410         420
GAAATAGAAG  GTTCCTATGA  AGAATTTGAT  GCTAAAAACC  CTGGAGGTTA  TGGTCTAAAT
         430         440         450         460         470         480
GATGCCTTTC  GGTACTTTGC  TTTAGCACGT  GATATGGAAA  GCAACAAGTT  CCAACCAAAA
         490         500         510         520         530         540
GCACAAAGCT  CACAAAAAGT  ATTTCACACT  GTAATGAAGA  GTGATGGGTT  ATCTATAATA
         550         560         570         580         590         600
TCTATCATGG  TTAACGGCTG  TTATGATTTT  TCTTCGGATA  ATTTATTAGT  ATCACCTTAT
         610         620         630         640         650         660
ATATGTGGAG  GTATAGGTGT  GGATGCAATA  GAATTTTTTG  ACGCATTACA  CATTAAACTT
         670         680         690         700         710         720
GCGTGCCAAA  GCAAATTAGG  CATCACTTAT  CAATTATCTT  ATAATATCAG  CTTATTTGCT
         730         740         750         760         770         780
GATGGATATT  ATCATCAAGT  AATAGGTAAC  CAATTCAGAA  ATTTAAACGT  TCAACATGTA
         790         800         810         820         830         840
GCTGAACTTA  ATGATGCACC  TAAAGTTACA  TCTGCAGTTG  CCACACTTAA  TGTTGGATAT
         850         860         870         880         890         900
TTCGGCGCTG  AAGTTGGAGT  AAGATTTATA  TTTTAA....  ..........  ..........
```

Fig. 11A

```
          10          20          30          40          50          60
MNKKNKFIIA  TALVYLLSLP  SVSFSEVTNS  SIKKHSGLYI  SGQYKPSVSV  FSSFSIKETN
          70          80          90         100         110         120
TITKNLIALK  KDINSLEVNA  DASQGISHPG  NFTIPYIAAF  EDNAFNFNGA  IGYITEGLRI
         130         140         150         160         170         180
EIEGSYEEFD  AKNPGGYGLN  DAFRYFALAR  DMESNKFQPK  AQSSQKVFHT  VMKSDGLSII
         190         200         210         220         230         240
SIMVNGCYDF  SSDNLLVSPY  ICGGIGVDAI  EFFDALHIKL  ACQSKLGITY  QLSYNISLFA
         250         260         270         280         290         300
DGYYHQVIGN  QFRNLNVQHV  AELNDAPKVT  SAVATLNVGY  FGAEVGVRFI  F.........
```

Fig. 11B

```
           10         20         30         40         50         60
    TCTAGAATAC ATGATGAAAA TTATGCTATT ACAACAAATA ATAAATTATC CATCGCATCT
           70         80         90        100        110        120
    ATTATGGTTA ACACCTGCTA TGATATTTCA ATTAATAATA CATCAATAGT ACCGTATTTA
          130        140        150        160        170        180
    TGCACAGGCA TTGGTGAAGA TCTTGTAGGG CTTTTTAATA CAATACATTT TAAACTTGCA
          190        200        210        220        230        240
    TATCAAGGGA AAGTTGGAAT GAGTTATTTG ATAAATAACA ATATCCTATT ATTTTCTGAC
          250        260        270        280        290        300
    ATATATTATC ATAAAGTCAT GGGTAACAGA TTTAAAAATT TGTACATGCA ATATGTAGCT
          310        320        330        340        350        360
    GATCCTAATA TTTCTGAAGA AACTATACCT ATATTAGCAA AACTTGATAT TGGTTATTTT
          370        380        390        400        410        420
    GGAAGTGAAA TTGGAATAAG GTTTATGTTT AACTAA.... .......... ..........
```

Fig. 12A

```
           10         20         30         40         50         60
    SRIHDENYAI TTNNKLSIAS IMVNTCYDIS INNTSIVPYL CTGIGEDLVG LFNTIHFKLA
           70         80         90        100        110        120
    YQGKVGMSYL INNNILLFSD IYYHKVMGNR FKNLYMQYVA DPNISEETIP ILAKLDIGYF
          130        140        150        160        170        180
    GSEIGIRFMF N......... .......... .......... .......... ..........
```

Fig. 12B

```
  10         20         30         40         50         60
ATGACAAAGA AATTTAATTT TGTAAATGTT ATATTAACAT TTTTGTTATT TCTTTTCCCA
  70         80         90        100        110        120
CTTAAGTCAT TTACAACATA TGCAAATAAT AACACAATCA CTCAAAAAGT TGGATTGTAC
 130        140        150        160        170        180
ATAAGTGGTC AATATAAGCC AAGTATTCCT CATTTCAAGA ATTTTCAGT AGAAGAAAAT
 190        200        210        220        230        240
GACAAAGTAG TAGATTTGAT AGGTCTTACA ACTGATGTTA CATATATCAC AGAACATATA
 250        260        270        280        290        300
TTACGAGATA ATACAAAATT CAACACTCAT TATATTGCAA AGTTCAAGAA CAATTTTATA
 310        320        330        340        350        360
AATTTCAGCA GTGCAATTGG TTATTATTCT GGGCAAGGAC CAAGGTTAGA AATAGAAAGC
 370        380        390        400        410        420
TCTTATGGGG ATTTTGATGT TGTAAATTAT AAAAATTATG CAGTACAAGA TGTTAATAGA
 430        440        450        460        470        480
TATTTTGCTT TAGTACGTGA AAAAAATGGT TCAAATTTCT CTCCAAAACC ACATGAAACT
 490        500        510        520        530        540
AGTCAACCCT CTGACAGTAA TCCTAAAAAG TCTTTTTATA CTTTAATGAA GAATAATGGG
 550        560        570        580        590        600
GTATTTGTTG CATCAGTAAT AATCAACGGT TGTTATGATT TTTCTTTTAA TAACACAACA
 610        620        630        640        650        660
ATATCACCTT ACGTATGTAT AGGAGTTGGA GGAGATTTTA TAGAGTTTTT TGAAGTAATG
 670        680        690        700        710        720
CATATCAAGT TTGCTTGCCA AAGTAAGGTT GGTATTAGCT ATCCAATATC TCCCTCTATT
 730        740        750        760        770        780
ACTATTTTTG CTGATGCAVA TTATCACAAG GTCATAAATA ATAAATTTAA CAACCTACAT
 790        800        810        820        830        840
GTTAAGTATT CATATGAACT TAAAAACTCA CCTACCATTA CCTCTGCAAC AGCCAAACTA
 850        860        870        880        890        900
AACATTGAAT ATTTTGGTGG TGAAGTTGGG ATGAGATTTA TATTTTAA..  ..........
```

Fig. 13A

```
  10         20         30         40         50         60
MTKKFNFVNV ILTFLLFLFP LKSFTTYANN NTITQKVGLY ISGQYKPSIP HFKNFSVEEN
  70         80         90        100        110        120
DKVVDLIGLT TDVTYITEHI LRDNTKFNTH YIAKFKNNFI NFSSAIGYYS GQGPRLEIES
 130        140        150        160        170        180
SYGDFDVVNY KNYAVQDVNR YFALVREKNG SNFSPKPHET SQPSDSNPKK SFYTLMKNNG
 190        200        210        220        230        240
VFVASVIING CYDFSFNNTT ISPYVCIGVG GDFIEFFEVM HIKFACQSKV GISYPISPSI
 250        260        270        280        290        300
TIFADAHYHK VINNKFNNLH VKYSYELKNS PTITSATAKL NIEYFGGEVG MRFIF.....
```

Fig. 13B

```
          10         20         30         40         50         60
ATGAGCAAAA AAAAGTTTAT TACAATAGGA ACAGTACTTG CATCTCTATT ATCATTCTTA
          70         80         90        100        110        120
TCTATTGAAT CCTTTTCAGC TATAAATCAT AATCATACAG GAAATAACAC TAGTGGTATA
         130        140        150        160        170        180
TATATTACAG GGCAGTATAG ACCAGGAGTA TCCCATTTTA GCAATTTCTC AGTAAAAGAA
         190        200        210        220        230        240
ACTAATGTTG ATACAATACA ACTAGTAGGA TATAAAAAAA GTGCGTCTTC TATCGATCCT
         250        260        270        280        290        300
AACACTTATT CAAACTTTCA AGGTCCATAT ACTGTTACAT TCAAGATAA TGCTGCTAGT
         310        320        330        340        350        360
TTCAGTGGAG CAATTGGATA TTCTTACCCC GAAAGTCTAA GACTTGAACT TGAAGGTTCT
         370        380        390        400        410        420
TACGAAAAAT TTGATGTCAA AGATCCTAAA GACTACTCAG CAAAAGATGC TTTTAGGTTT
         430        440        450        460        470        480
TTTGCTCTAG CACGTAATAC GTCTACTACT GTTCCTGATG CTCAAAAATA TACAGTTATG
         490        500        510        520        530        540
AAGAATAATG GCTTATCTGT TGCATCAATC ATGATCAATG GTTGTTATGA TCTATCTTTT
         550        560        570        580        590        600
AATAATTTAG TCGTATCACC TTATATATGT GCAGGTATTG GTGAAGATTT CATTGAATTT
         610        620        630        640        650        660
TTTGATACTT TGCACATTAA ACTTGCTTAT CAAGGAAAAC TAGGTATTAG TTATTACTTC
         670        680        690        700        710        720
TTTCCTAAGA TTAATGTATT TGCTGGTGGG TACTATCATA GAGTTATAGG GAATAAATTT
         730        740        750        760        770        780
AAAAATTTAA ATGTTAACCA TGTTGTTACA CTTGATGAAT TCCTAAAGC AACTTCTGCA
         790        800        810        820        830        840
GTAGCTACAC TTAATGTTGC TTATTTTGGT GGTGAAGCTG GAGTAAAGTT TACATTTTAA
         850        860        870        880        890        900
.......... .......... .......... .......... .......... ..........
```

Fig. 14A

```
          10         20         30         40         50         60
MSKKKFITIG TVLASLLSFL SIESFSAINH NHTGNNTSGI YITGQYRPGV SHFSNFSVKE
          70         80         90        100        110        120
TNVDTIQLVG YKKSASSIDP NTYSNFQGPY TVTFQDNAAS FSGAIGYSYP ESLRLELEGS
         130        140        150        160        170        180
YEKFDVKDPK DYSAKDAFRF FALARNTSTT VPDAQKYTVM KNNGLSVASI MINGCYDLSF
         190        200        210        220        230        240
NNLVVSPYIC AGIGEDFIEF FDTLHIKLAY QGKLGISYYF FPKINVFAGG YYHRVIGNKF
         250        260        270        280        290        300
KNLNVNHVVT LDEFPKATSA VATLNVAYFG GEAGVKFTF. .......... ..........
```

Fig. 14B

```
         10         20         30         40         50         60
ATGAGTGCTA AAAAAAAGCT TTTTATAATA GGGTCAGTGT TAGTATGTTT AGTGTCATAC
         70         80         90        100        110        120
TTACCTACTA AATCTTTGTC AAACTTAAAT AATATTAATA ATAACACTAA GTGCACTGGG
        130        140        150        160        170        180
CTATATGTCA GTGGACAATA TAAACCTACT GTTTCTCACT TTAGTAATTT TTCACTTAAA
        190        200        210        220        230        240
GAAACTTATA CTGACACTAA AGAGTTATTA GGACTAGCAA AAGATATTAA GTCTATTACA
        250        260        270        280        290        300
GATATAACAA CAAATAAAAA ATTCAACATT CCTTATAACA CAAAATTTCA AGATAATGCT
        310        320        330        340        350        360
GTTAGCTTCA GTGCAGCTGT TGGATATATT TCCCAAGACA GTCCAAGGGT TGAGGTAGAA
        370        380        390        400        410        420
TGGTCTTATG AAGAATTTGA CGTTAAAAAT CCTGGTAATT ACGTAGTAAG TGAAGCCTTC
        430        440        450        460        470        480
AGGTATATTG CTTTAGCAAG AGGAATTGAT AATCTTCAAA AATATCCTGA AACAAATAAG
        490        500        510        520        530        540
TATGTTGTTA TAAAGAACAA TGGCTTATCT GTCGCATCCA TTATAATCAA TGGCTGTTAT
        550        560        570        580        590        600
GATTTTCTT TAAACAATTT AAAAGTATCA CCTTACATAT GCGTAGGGTT TGGTGGGGAC
        610        620        630        640        650        660
ATTATAGAAT TTTTTAGTGC TGTAAGTTTT AAATTTGCTT ATCAAGGTAA GGTAGGTATC
        670        680        690        700        710        720
AGTTATCCAT TATTCTCTAA TATGATTATA TTTGCTGACG GATATTACCA TAAGGTCATA
        730        740        750        760        770        780
GGAAATAAAT TTAACAATTT AAATGTTCAA CACGTTGTTA GTCTTAACAG TCATCCTAAG
        790        800        810        820        830        840
TCTACTTTTG CAGTAGCTAC TCTTAATGTT GAGTATTTCG GTAGTGAATT TGGGTTAAAA
        850        860        870        880        890        900
TTTATATTTT AA........ .......... .......... .......... ..........
```

Fig. 15A

```
         10         20         30         40         50         60
MSAKKKLFII GSVLVCLVSY LPTKSLSNLN NINNNTKCTG LYVSGQYKPT VSHFSNFSLK
         70         80         90        100        110        120
ETYTDTKELL GLAKDIKSIT DITTNKKFNI PYNTKFQDNA VSFSAAVGYI SQDSPRVEVE
        130        140        150        160        170        180
WSYEEFDVKN PGNYVVSEAF RYIALARGID NLQKYPETNK YVVIKNNGLS VASIINGCY
        190        200        210        220        230        240
DFSLNNLKVS PYICVGFGGD IIEFFSAVSF KFAYQGKVGI SYPLFSNMII FADGYYHKVI
        250        260        270        280        290        300
GNKFNNLNVQ HVVSLNSHPK STFAVATLNV EYFGSEFGLK FIF....... ..........
```

Fig. 15B

```
         10         20         30         40         50         60
ATGAGTAAAA AAAATTTTAT TACAATAGGA GCAACACTTA TTCATATGTT GTTACCTAAC
         70         80         90        100        110        120
ATATCTTTTC CAGAAACTAT TAACAATAAC ACTGATAAAC TTTCTGGGTT ATATATAAGT
        130        140        150        160        170        180
GGGCAATATA AACCAGGGAT TTCTCATTTC AGCAAATTTT CAGTCAAAGA AATCTATAAT
        190        200        210        220        230        240
GATAACATTC AACTAATTGG GTTAAGACAC AACGCAATTT CTACTAGTAC CCTTAATATT
        250        260        270        280        290        300
AATACAGATT TTAATATCCC CTATAAAGTA ACATTTCAAA ATAACATTAC CAGCTTTAGT
        310        320        330        340        350        360
GGAGCTATTG GTTATTCTGA TCCCACAGGG GCAAGATTTG AGCTTGAAGG TTCTTATGAA
        370        380        390        400        410        420
GAATTTGATG TGACAGATCC TGGAGACTGC TTAATAAAAG ATACCTATAG ATATTTCGCT
        430        440        450        460        470        480
TTAGCTAGAA ACCCATCAGG TTCTAGCCCT ACCTCAAACA ACTATACTGT TATGAGAAAT
        490        500        510        520        530        540
GATGGTGTTT CCATTACTTC TGTTATATTT AATGGCTGTT ATGACATCTT TTTAAAGGAT
        550        560        570        580        590        600
TTAGAAGTAT CACCTTATGT ATGTGTTGGT GTAGGTGGAG ATTTTATAGA ATTTTTTGAC
        610        620        630        640        650        660
GCATTACACA TTAAATTAGC ATACCAAGGC AAGTTAGGTA TCAATTATCA CTTATCGACT
        670        680        690        700        710        720
CAAGCAAGCG TATTTATTGA TGGATATTAT CATAAGGTTA TAGGAAATCA ATTCAACAAT
        730        740        750        760        770        780
CTAAATGTTC AACACGTGGC TAGTACAGAT TTTGGACCTG TATACGCAGT AGCCACACTT
        790        800        810        820        830        840
AACATTGGTT ATTTTGGTGG TGAAATCGGA ATTAGACTTA CATTTAA...  ..........
```

Fig. 16A

```
         10         20         30         40         50         60
MSKKNFITIG ATLIHMLLPN ISFPETINNN TDKLSGLYIS GQYKPGISHF SKFSVKEIYN
         70         80         90        100        110        120
DNIQLIGLRH NAISTSTLNI NTDFNIPYKV TFQNNITSFS GAIGYSDPTG ARFELEGSYE
        130        140        150        160        170        180
EFDVTDPGDC LIKDTYRYFA LARNPSGSSP TSNNYTVMRN DGVSITSVIF NGCYDIFLKD
        190        200        210        220        230        240
LEVSPYVCVG VGGDFIEFFD ALHIKLAYQG KLGINYHLST QASVFIDGYY HKVIGNQFNN
        250        260        270        280        290        300
LNVQHVASTD FGPVYAVATL NIGYFGGEIG IRLTF.....  ..........  ..........
```

Fig. 16B

```
         10         20         30         40         50         60
ATGAATAATA GAAAAAGTTT TTTTATAATA GGTGCATCAT TACTAGCAAG CTTATTATTC
         70         80         90        100        110        120
ACATCTGAGG CCTCTTCTAC AGGAAATGTA AGTAACCATA CTTATTTTAA ACCTAGGTTA
        130        140        150        160        170        180
TATATCAGTG GACAATATAG ACCAGGAGTT TCTCATTTTA GCAAATTTTC AGTCAAAGAA
        190        200        210        220        230        240
ACCAACTACA ATACTACTCA ACTAGTTGGG CTTAAAAAGG ACATCAGTGT CATAGGGAAC
        250        260        270        280        290        300
AGTAATATCA CAACCTACAC AAATTTCAAC TTTCCTTACA TTGCAGAATT TCAAGACAAT
        310        320        330        340        350        360
GCCATAAGTT TCAGTGGGGC AATTGGATAC TTGTATTCCG AGAATTTTAG AATTGAAGTA
        370        380        390        400        410        420
GAGGCTTCTT ATGAAGAATT TGATGTTAAA AATCCAGAAG GATCTGCTAC AGACGCATAC
        430        440        450        460        470        480
AGGTATTTTG CACTAGCACG TGCTATGGAT GGCACTAATA AATCTAGTCC TGATGACACA
        490        500        510        520        530        540
AGAAAATTCA CTGTCATGAG AAATGACGGG TTATCAATTT CATCAGTAAT GATAAATGGG
        550        560        570        580        590        600
TGTTACAATT TTACATTAGA TGATATACCA GTAGTACCGT ATGTATGCGC AGGAATAGGA
        610        620        630        640        650        660
GGAGATTTCA TAGAGTTTTT TAATGATTTA CATGTTAAGT TCGTCATCA AGGCAAGGTA
        670        680        690        700        710        720
GGTATTAGTT ATTCTATATC CCCTGAAGTA AGTTTATTTC TTAACGGATA TTACCATAAA
        730        740        750        760        770        780
GTAACAGGTA ACAGATTTAA AAACTTACAC GTTCAACACG TAAGTGATTT AAGTGACGCT
        790        800        810        820        830        840
CCTAAGTTCA CATCTGCAGT TGCTACACTC AATGTTGGGT ACTTTGGTGG CGAAATTGGA
        850        860        870        880        890        900
GTAAGATTTA TATTTTAA..  ........   ........   ........   ........
```

Fig. 17A

```
         10         20         30         40         50         60
MNNRKSFFII GASLLASLLF TSEASSTGNV SNHTYFKPRL YISGQYRPGV SHFSKFSVKE
         70         80         90        100        110        120
TNYNTTQLVG LKKDISVIGN SNITTYTNFN FPYIAEFQDN AISFSGAIGY LYSENFRIEV
        130        140        150        160        170        180
EASYEEFDVK NPEGSATDAY RYFALARAMD GTNKSSPDDT RKFTVMRNDG LSISSVMING
        190        200        210        220        230        240
CYNFTLDDIP VVPYVCAGIG GDFIEFFNDL HVKFAHQGKV GISYSISPEV SLFLNGYYHK
        250        260        270        280        290        300
VTGNRGKNLH VQHVSDLSDA PKFTSAVATL NVGYFGGEIF VRFIF.....  ........
```

Fig. 17B

```
        10          20          30          40          50          60
ATGAAGAAGA  AAAATCAATT  TATCACAATA  AGTACAATAT  TAGTATGTTT  ATTGTCATTA
        70          80          90         100         110         120
TCTAATGCAT  CACTTTCAAA  CACTACAAAT  AGCAGCACTA  AAAAACAGTT  TGGGTTATAT
       130         140         150         160         170         180
GTTAGTGGAC  AATACAAGCC  TAGTGTTTCT  ATTTTTAGCA  ATTTCTCAGT  AAAGGAAACT
       190         200         210         220         230         240
AATTTTCCTA  CAAAGTATCT  AGCAGCTCTT  AAAAAAGACA  TTAATTCTGT  CGAATTTGAC
       250         260         270         280         290         300
GATAGTGTTA  CTGCTGGCAT  TAGTTACCCA  CTTAATTTCA  GTACTCCTTA  TATAGCTGTA
       310         320         330         340         350         360
TTTCAAGATA  ATATTTCTAA  TTTTAATGGC  GCTATTGGGT  ACACTTTTGT  TGAAGGCCCA
       370         380         390         400         410         420
AGAATTGAAA  TAGAAGGTTC  TTATGAAGAA  TTCGATGTCA  AAGACCTGGA  AGATATACAG
       430         440         450         460         470         480
AAATACAAGA  TGCATACCGT  TGACTTTGCT  TTAGCACGTG  ATATAGACTC  TATTCCTACT
       490         500         510         520         530         540
AGCCCAAAAA  ATAGAACTTC  ACATGATGGC  AACAGTTCAT  ATAAGGTATA  CCACACTGTA
       550         560         570         580         590         600
ATGAAAAATG  AAGGACTATC  TATAATATCC  ATTATGGTCA  ATGGCTGCTA  TGATTTTTCT
       610         620         630         640         650         660
TCAGATAATT  TATCAATATT  ACCTTATGTA  TGTGGTGGTA  TAGGTGTAAA  TGCTATAGAG
       670         680         690         700         710         720
TTTTTCGATG  CATTACATGT  TAAATTCGCG  TGTCAGGGTA  AATTAGGTAT  TACTTATCCA
       730         740         750         760         770         780
TTATCTTCCA  ACGTTAGTTT  ATTTGCTGGT  GGATATTATC  ACCAAGTAAT  GGGCAACCAA
       790         800         810         820         830         840
TTTAAAAATC  TAAATGTTCA  ACATGTAGCT  GAACTTAATG  ACGCACCCAA  AGTTACATCT
       850         860         870         880         890         900
GCAGTAGCTA  CACTTGACAT  TGGGTATTTT  GGTGGTGAAA  TTGGAGCAAG  GCTTATATTT
       910         920         930         940         950         960
TAA.......  ..........  ..........  ..........  ..........  ..........
```

Fig. 18A

```
        10          20          30          40          50          60
MKKKNQFITI  STILVCLLSL  SNASLSNTTN  SSTKKQFGLY  VSGQYKPSVS  IFSNFSVKET
        70          80          90         100         110         120
NFPTKYLAAL  KKDINSVEFD  DSVTAGISYP  LNFSTPYIAV  FQDNISNFNG  AIGYTFVEGP
       130         140         150         160         170         180
RIEIEGSYEE  FDVKDLEDIQ  KYKMHTVDFA  LARDIDSIPT  SPKNRTSHDG  NSSYKVYHTV
       190         200         210         220         230         240
MKNEGLSIIS  IMVNGCYDFS  SDNLSILPYV  CGGIGVNAIE  FFDALHVKFA  CQGKLGITYP
       250         260         270         280         290         300
LSSNVSLFAG  GYYHQVMGNQ  FKNLNVQHVA  ELNDAPKVTS  AVATLDIGYF  GGEIGARLIF
       310         320         330         340         350         360
..........  ..........  ..........  ..........  ..........  ..........
```

Fig. 18B

```
         10         20         30         40         50         60
ATGAATTGCA AAAGATTTTT CATAGCAAGT GCATTGATAT CACTAATGTC TTTCTTACCT
         70         80         90        100        110        120
AGCGTATCTT TTTCTGAATC AATACATGAA GATAATATAA ATGGTAACTT TTACATTAGT
        130        140        150        160        170        180
GCAAAGTATA TGCCAAGTGC CTCACACTTT GGCGTATTTT CAGTTAAAGA AGAGAAAAAC
        190        200        210        220        230        240
ACAACAACTG GAGTTTTCGG ATTAAAACAA GATTGGGACG GAGCAACAAT AAAGGATGCA
        250        260        270        280        290        300
AGCAGCAGCC ACACAATAGA CCCAAGTACA ATATTCTCCA TTTCAAATTA TTCATTTAAA
        310        320        330        340        350        360
TATGAAAACA ATCCATTTTT AGGGTTTGCA GGAGCTATTG GCTACTCAAT GGGTGGTCCA
        370        380        390        400        410        420
AGGGTAGAGT TTGAAGTGTC TTACGAAATA TTTGATGTAA AAAACCAAGG TAACAGTTAC
        430        440        450        460        470        480
AAGAACGATG CTCACAAATA TTGCGCTTTA TCAAGACACA CCGGAGGTAT GCCACAAGCC
        490        500        510        520        530        540
GGTCATCAAA ATAAATTTGT CTTCCTAAAA AATGAAGGAT TACTTGACAT ATCACTTATG
        550        560        570        580        590        600
ATAAACGCAT GTTATGATAT AACAATCGAC AGCATGCCAT TTTCTCCATA TATATGTGCA
        610        620        630        640        650        660
GGTATTGGTA GTGACTTAGT TTCGATGTTT GAAACTACAA ATCCTAAAAT TTCTTATCAA
        670        680        690        700        710        720
GGAAAATTAG GTGTAAGTTA CTCCATAAGC CCAGAAGCAT CTGTTTTTGT TGGAGGACAC
        730        740        750        760        770        780
TTTCACAGAG TTATAGGTAA TGAATTTAAA GACATTCCTG CAATAACTCC TGCTGGAGCA
        790        800        810        820        830        840
ACAGAAATTA AAGGCACACA GTTTACAACA GTAACATTAA ACATATGCCA CTTCGGACTA
        850        860        870        880        890        900
GAGCTTGGAG GCAGGTTTAC TTTTTAA...  .........  .........  .........
```

Fig. 19A

```
         10         20         30         40         50         60
MNCKRFFIAS ALISLMSFLP SVSFSESIHE DNINGNFYIS AKYMPSASHF GVFSVKEEKN
         70         80         90        100        110        120
TTTGVFGLKQ DWDGATIKDA SSSHTIDPST IFSISNYSFK YENNPFLGFA GAIGYSMGGP
        130        140        150        160        170        180
RVEFEVSYEI FDVKNQGNSY KNDAHKYCAL SRHTGGMPQA GHQNKFVFLK NEGLLDISLM
        190        200        210        220        230        240
INACYDITID SMPFSPYICA GIGSDLVSMF ETTNPKISYQ GKLGVSYSIS PEASVFVGGH
        250        260        270        280        290        300
FHRVIGNEFK DIPAITPAGA TEIKGTQFTT VTLNICHFGL ELGGRFTF.. .........
```

Fig. 19B

```
         10         20         30         40         50         60
ATGAAATATA AAAAAACTTT TACAGTAACT GCATTAGTAT TATTAACTTC CTTTACACAT
         70         80         90        100        110        120
TTTATACCTT TTATAGTCC AGCACGTGCC AGTACAATTC ACAACTTCTA CATTAGTGGA
        130        140        150        160        170        180
AAATATATGC CAACAGCGTC ACATTTTGGA ATTTTTTCAG CTAAAGAAGA ACAAAGTTTT
        190        200        210        220        230        240
ACTAAGGTAT TAGTTGGGTT AGATCAACGA TTATCACATA ATATTATAAA CAATAATGAT
        250        260        270        280        290        300
ACAGCAAAGA GTCTTAAGGT TCAAAATTAT TCATTTAAAT ACAAAAATAA CCCATTTCTA
        310        320        330        340        350        360
GGATTTGCAG GAGCTATTGG TTATTCAATA GGCAATTCAA GAATAGAACT AGAAGTATCA
        370        380        390        400        410        420
CATGAAATAT TTGATACTAA AAACCCAGGA ACAATTATT TAAATGACTC TCACAAATAT
        430        440        450        460        470        480
TGCGCTTTAT CTCATGGAAG TCACATATGC AGTGATGGAA ATAGCGGAGA TTGGTACACT
        490        500        510        520        530        540
GCAAAAACTG ATAAGTTTGT ACTTCTGAAA AATGAAGGTT TACTTGACGT CTCATTTATG
        550        560        570        580        590        600
TTAAACGCAT GTTATGACAT AACAACTGAA AAAATGCCTT TTTCACCTTA TATATGTGCA
        610        620        630        640        650        660
GGTATTGGTA CTGATCTCAT ATCTATGTTT GAGACAACAC AAAACAAAAT ATCTTATCAA
        670        680        690        700        710        720
GGAAAGTTAG GTTTAAACTA TACTATAAAC TCAAGAGTTT CTGTTTTTGC AGGTGGGCAC
        730        740        750        760        770        780
TTTCATAAAG TAATAGGTAA TGAATTTAAA GGTATTCCTA CTCTATTACC TGATGGATCA
        790        800        810        820        830        840
AACATTAAAG TACAACAGTC TGCAACAGTA ACATTAGATG TGTGCCATTT CGGGTTAGAG
        850        860        870        880        890        900
ATTGGAAGTA GATTTTTCTT TTAA......  .........  .........  .........
```

Fig. 20A

```
         10         20         30         40         50         60
MKYKKTFTVT ALVLLTSFTH FIPFYSPARA STIHNFYISG KYMPTASHFG IFSAKEEQSF
         70         80         90        100        110        120
TKVLVGLDQR LSHNIINNND TAKSLKVQNY SFKYKNNPFL GFAGAIGYSI GNSRIELEVS
        130        140        150        160        170        180
HEIFDTKNPG NNYLNDSHKY CALSHGSHIC SDGNSGDWYT AKTDKFVLLK NEGLLDVSFM
        190        200        210        220        230        240
LNACYDITTE KMPFSPYICA GIGTDLISMF ETTQNKISYQ GKLGLNYTIN SRVSVFAGGH
        250        260        270        280        290        300
FHKVIGNEFK GIPTLLPDGS NIKVQQSATV TLDVCHFGLE IGSRFFF... ..........
```

Fig. 20B

```
         10         20         30         40         50         60
ATGTTTTATA CTAATATATA TATTCTGGCT TGTATTTACT TTGCACTTCC ACTATTGTTA
         70         80         90        100        110        120
ATTTATTTTC ACTATTTTAG GTGTAATATG AATTGCAAAA AAATTCTTAT AACAACTGCA
        130        140        150        160        170        180
TTAATATCAT TAATGTACTC TATTCCAAGC ATATCTTTTT CTGATACTAT ACAAGATGGT
        190        200        210        220        230        240
AACATGGGTG GTAACTTCTA TATTAGTGGA AAGTATGTAC CAAGTGTCTC ACATTTTGGT
        250        260        270        280        290        300
AGCTTCTCAG CTAAAGAAGA AAGCAAATCA ACTGTTGGAG TTTTTGGATT AAAACATGAT
        310        320        330        340        350        360
TGGGATGGAA GTCCAATACT TAAGAATAAA CACGCTGACT TTACTGTTCC AAACTATTCG
        370        380        390        400        410        420
TTCAGATACG AGAACAATCC ATTTCTAGGG TTTGCAGGAG CTATCGGTTA CTCAATGGGT
        430        440        450        460        470        480
GGCCCAAGAA TAGAATTCGA AATATCTTAT GAAGCATTCG ACGTAAAAAG TCCTAATATC
        490        500        510        520        530        540
AATTATCAAA ATGACGCGCA CAGGTACTGC GCTCTATCTC ATCACACATC GGCAGCCATG
        550        560        570        580        590        600
GAAGCTGATA AATTTGTCTT CTTAAAAAAC GAAGGGTTAA TTGACATATC ACTTGCAATA
        610        620        630        640        650        660
AATGCATGTT ATGATATAAT AAATGACAAA GTACCTGTTT CTCCTTATAT ATGCGCAGGT
        670        680        690        700        710        720
ATTGGTACTG ATTTGATTTC TATGTTTGAA GCTACAAGTC CTAAAATTTC CTACCAAGGA
        730        740        750        760        770        780
AAACTGGGCA TTAGTTACTC TATTAATCCG GAAACCTCTG TTTTCATCGG TGGGCATTTC
        790        800        810        820        830        840
CACAGGATCA TAGGTAATGA GTTTAGAGAT ATTCCTGCAA TAGTACCTAG TAACTCAACT
        850        860        870        880        890        900
ACAATAAGTG GACCACAATT TGCAACAGTA ACACTAAATG TGTGTCACTT TGGTTTAGAA
        910        920        930        940        950        960
CTTGGAGGAA GATTTAACTT CTAA...... .......... .......... ..........
```

Fig. 21A

```
         10         20         30         40         50         60
MFYTNIYILA CIYFALPLLL IYFHYFRCNM NCKKILITTA LISLMYSIPS ISFSDTIQDG
         70         80         90        100        110        120
NMGGNFYISG KYVPSVSHFG SFSAKEESKS TVGVFGLKHD WDGSPILKNK HADFTVPNYS
        130        140        150        160        170        180
FRYENNPFLG FAGAIGYSMG GPRIEFEISY EAFDVKSPNI NYQNDAHRYC ALSHHTSAAM
        190        200        210        220        230        240
EADKFVFLKN EGLIDISLAI NACYDIINDK VPVSPYICAG IGTDLISMFE ATSPKISYQG
        250        260        270        280        290        300
KLGISYSINP ETSVFIGGHF HRIIGNEFRD IPAIVPSNST TISGPQFATV TLNVCHFGLE
        310        320        330        340        350        360
LGGRFNF... .......... .......... .......... .......... ..........
```

Fig. 21B

```
         10         20         30         40         50         60
 ATGAATTGCA AAAAAATTCT TATAACAACT GCATTAATGT CATTAATGTA CTATGCTCCA
         70         80         90        100        110        120
 AGCATATCTT TTTCTGATAC TATACAAGAC GATAACACTG GTAGCTTCTA CATCAGTGGA
        130        140        150        160        170        180
 AAATATGTAC CAAGTGTTTC ACATTTGGT GTTTTCTCAG CTAAAGAAGA AAGAAACTCA
        190        200        210        220        230        240
 ACTGTTGGAG TTTTTGGATT AAAACATGAT TGGAATGGAG GTACAATATC TAACTCTTCT
        250        260        270        280        290        300
 CCAGAAAATA TATTCACAGT TCAAAATTAT TCGTTTAAAT ACGAAAACAA CCCATTCTTA
        310        320        330        340        350        360
 GGGTTTGCAG GAGCTATTGG TTATTCAATG GGTGGCCCAA GAATAGAACT TGAAGTTCTG
        370        380        390        400        410        420
 TACGAGACAT TCGATGTGAA AAATCAGAAC AATAATTATA AGAACGGCGC ACACAGATAC
        430        440        450        460        470        480
 TGTGCTTTAT CTCATCATAG TTCAGCAACA AACATGTCCT CCGCAAGTAA CAAATTTGTT
        490        500        510        520        530        540
 TTCTTAAAAA ATGAAGGGTT AATTGACTTA TCATTTATGA TAAATGCATG CTATGACATA
        550        560        570        580        590        600
 ATAATTGAAG GAATGCCTTT TTCACCTTAT ATTTGTGCAG GTGTTGGTAC TGATGTTGTT
        610        620        630        640        650        660
 TCCATGTTTG AAGCTATAAA TCCTAAAATT TCTTACCAAG GAAAACTAGG ATTAGGTTAT
        670        680        690        700        710        720
 AGTATAAGTT CAGAAGCCTC TGTTTTTATC GGTGGACACT TTCACAGAGT CATAGGTAAT
        730        740        750        760        770        780
 GAATTTAGAG ACATCCCTGC TATGGTTCCT AGTGGATCAA ATCTTCCAGA AAACCAATTT
        790        800        810        820        830        840
 GCAATAGTAA CACTAAATGT GTGTCACTTT GGTTTAGAAC TTGGAGGAAG ATTTAACTTC
        850        860        870        880        890        900
 TGA.......  .......... .......... .......... .......... ..........
```

Fig. 22A

```
         10         20         30         40         50         60
 MNCKKILITT ALMSLMYYAP SISFSDTIQD DNTGSFYISG KYVPSVSHFG VFSAKEERNS
         70         80         90        100        110        120
 TVGVFGLKHD WNGGTISNSS PENIFTVQNY SFKYENNPFL GFAGAIGYSM GGPRIELEVL
        130        140        150        160        170        180
 YETFDVKQN NNYKNGAHRY CALSHHSSAT NMSSASNKFV FLKNEGLIDL SFMINACYDI
        190        200        210        220        230        240
 IIEGMPFSPY ICAGVGTDVV SMFEAINPKI SYQGKLGLGY SISSEASVFI GGHFHRVIGN
        250        260        270        280        290        300
 EFRDIPAMVP SGSNLPENQF AIVTLNVCHF GLELGGRFNF .......... ..........
```

Fig. 22B

```
         10         20         30         40         50         60
ATGAATTGTA AAAAAGTTTT CACAATAAGT GCATTGATAT CATCCATATA CTTCCTACCT
         70         80         90        100        110        120
AATGTCTCAT ACTCTAACCC AGTATATGGT AACAGTATGT ATGGTAATTT TTACATATCA
        130        140        150        160        170        180
GGAAAGTACA TGCCAAGTGT TCCTCATTTT GGAATTTTTT CAGCTGAAGA AGAGAAAAAA
        190        200        210        220        230        240
AAGACAACTG TAGTATATGG CTTAAAAGGA AAACTGGCAG GAGATGCAAT ATCTAGTCAA
        250        260        270        280        290        300
AGTCCAGATG ATAATTTTAC CATTCGAAAT TACTCATTCA AGTATGCAAG CAACAAGTTT
        310        320        330        340        350        360
TTAGGGTTTG CAGTAGCTAT TGGTTACTCG ATAGGCAGTC CAAGAATAGA AGTTGAGATG
        370        380        390        400        410        420
TCTTATGAAG CATTTGATGT GAAAAATCCA GGTGATAATT ACAAAAACGG TGCTTACAGG
        430        440        450        460        470        480
TATTGTGCTT TATCTCATCA AGATGATGCG GATGATGACA TGACTAGTGC AACTGACAAA
        490        500        510        520        530        540
TTTGTATATT TAATTAATGA AGGATTACTT AACATATCAT TTATGACAAA CATATGTTAT
        550        560        570        580        590        600
GAAACAGCAA GCAAAAATAT ACCTCTCTCT CCTTACATAT GTGCAGGTAT TGGTACTGAT
        610        620        630        640        650        660
TTAATTCACA TGTTTGAAAC TACACATCCT AAAATTTCTT ATCAAGGAAA GCTAGGGTTG
        670        680        690        700        710        720
GCCTACTTCG TAAGTGCAGA GTCTTCGGTT TCTTTTGGTA TATATTTTCA TAAAATTATA
        730        740        750        760        770        780
AATAATAAGT TTAAAAATGT TCCAGCCATG GTACCTATTA ACTCAGACGA GATAGTAGGA
        790        800        810        820        830        840
CCACAGTTTG CAACAGTAAC ATTAAATGTA TGCTACTTTG GATTAGAACT TGGATGTAGG
        850        860        870        880        890        900
TTCAACTTCT AA........ .......... .......... .......... ..........
```

Fig. 23A

```
         10         20         30         40         50         60
MNCKKVFTIS ALISSIYFLP NVSYSNPVYG NSMYGNFYIS GKYMPSVPHF GIFSAEEEKK
         70         80         90        100        110        120
KTTVVYGLKG KLAGDAISSQ SPDDNFTIRN YSFKYASNKF LGFAVAIGYS IGSPRIEVEM
        130        140        150        160        170        180
SYEAFDVKNP GDNYKNGAYR YCALSHQDDA DDDMTSATDK FVYLINEGLL NISFMTNICY
        190        200        210        220        230        240
ETASKNIPLS PYICAGIGTD LIHMFETTHP KISYQGKLGL AYFVSAESSV SFGIYFHKII
        250        260        270        280        290        300
NNKFKNVPAM VPINSDEIVG PQFATVPLKV CYFGLELGCR FNF....... ..........
```

Fig. 23B

```
          10         20         30         40         50         60
ATGAACTGTA AAAAAATTCT TATAACAACT ACATTGGTAT CACTAACAAT TCTTTTACCT
          70         80         90        100        110        120
GGCATATCTT TCTCCAAACC AATACATGAA AACAATACTA CAGGAAACTT TTACATTATT
         130        140        150        160        170        180
GGAAAATATG TACCAAGTAT TTCACATTTT GGGACTTTT  CAGCTAAAGA AGAAAAAAAC
         190        200        210        220        230        240
ACAACAACTG GAATTTTTGG ATTAAAAGAA TCATGGACTG GTGGTATCAT CCTTGATAAA
         250        260        270        280        290        300
GAACATGCAG CTTTTAATAT CCCAAATTAT TCATTTAAAT ATGAAAATAA TCCATTTTTA
         310        320        330        340        350        360
GGATTTGCAG GGGTAATTGG CTATTCAATA GGTAGTCCAA GAATAGAATT TGAAGTATCA
         370        380        390        400        410        420
TACGAGACAT TCGATGTACA AAATCCAGGA GATAAGTTTA ACAATGATGC ACATAAGTAT
         430        440        450        460        470        480
TGTGCTTTAT CCAATGATTC CAGTAAAACA ATGAAAGTG  GTAAATTCGT TTTTCTCAAA
         490        500        510        520        530        540
AATGAAGGAT TAAGTGACAT ATCACTCATG TTAAATGTAT GTTATGATAT AATAAACAAA
         550        560        570        580        590        600
AGAATGCCTT TTTCACCTTA CATATGTGCA GGCATTGGTA CTGACTTAAT ATTCATGTTT
         610        620        630        640        650        660
GACGCTATAA ACCATAAAGC TGCTTATCAA GGAAAATTAG GTTTTAATTA TCCAATAAGC
         670        680        690        700        710        720
CCAGAAGCTA ACATTTCTAT GGGTGTGCAC TTTCACAAAG TAACAAACAA CGAGTTTAGA
         730        740        750        760        770        780
GTTCCTGTTC TATTAACTGC TGGAGGACTC GCTCCAGATA ATCTATTTGC AATAGTAAAG
         790        800        810        820        830        840
TTGAGTATAT GTCATTTTGG GTTAGAATTT GGGTACAGGG TCAGTTTTTA A.........
```

Fig. 24A

```
          10         20         30         40         50         60
MNCKKILITT TLVSLTILLP GISFSKPIHE NNTTGNFYII GKYVPSISHF GNFSAKEEKN
          70         80         90        100        110        120
TTTGIFGLKE SWTGGIILDK EHAAFNIPNY SFKYENNPFL GFAGVIGYSI GSPRIEFEVS
         130        140        150        160        170        180
YETFDVQNPG DKFNNDAHKY CALSNDSSKT MKSGKFVFLK NEGLSDISLM LNVCYDIINK
         190        200        210        220        230        240
RMPFSPYICA GIGTDLIFMF DAINHKAAYQ GKLGFNYPIS PEANISMGVH FHKVTNNEFR
         250        260        270        280        290        300
VPVLLTAGGL APDNLFAIVK LSICHFGLEF GYRVSF.... .......... ..........
```

Fig. 24B

```
         10         20         30         40         50         60
ATGAATAATA AACTCAAATT TACTATAACA AACACAGTAT TAGTATGCTT ATTGTCATTA
         70         80         90        100        110        120
CCTAATATAT CTTCCTCAAA GGCCATAAAC AATAACGCTA AAAAGTACTA CGGATTATAT
        130        140        150        160        170        180
ATCAGTGGAC AATATAAACC CAGTGTTTCT GTTTTCAGTA ATTTTTCAGT TAAAGAAACC
        190        200        210        220        230        240
AATGTCATAA CTAAAAACCT TATAGCTTTA AAAAAGATG TTGACTCTAT TGAAACCAAG
        250        260        270        280        290        300
ACTGATGCCA GTGTAGGTAT TAGTAACCCA TCAAATTTTA CTATCCCCTA TACAGCTGTA
        310        320        330        340        350        360
TTTCAAGATA ATTCTGTCAA TTTCAATGGA ACTATTGGTT ACACCTTTGC TGAAGGTACA
        370        380        390        400        410        420
AGAGTTGAAA TAGAAGGTTC TTATGAGGAA TTTGATGTTA AAAACCCTGG AGGCTATACA
        430        440        450        460        470        480
CTAAGTGATG CCTATCGCTA TTTTGCATTA GCACGTGAAA TGAAAGGTAA TAGTTTTACA
        490        500        510        520        530        540
CCTAAAGAAA AAGTTTCTAA TAGTATTTTT CACACTGTAA TGAGAAATGA TGGATTATCT
        550        560        570        580        590        600
ATAATATCTG TTATAGTAAA TGTTTGCTAC GATTTCTCTT TGAACAATTT GTCAATATCG
        610        620        630        640        650        660
CCTTACATAT GTGGAGGAGC AGGGGTAGAT GCTATAGAAT TCTTCGATGT ATTACACATT
        670        680        690        700        710        720
AAGTTTGCAT ATCAAAGCAA GCTAGGTATT GCTTATTCTC TACCATCTAA CATTAGTCTC
        730        740        750        760        770        780
TTTGCTAGTT TATATTACCA TAAAGTAATG GGCAATCAAT TTAAAAATTT AAATGTCCAA
        790        800        810        820        830        840
CATGTTGCTG AACTTGCAAG TATACCTAAA ATTACATCCG CAGTTGCTAC ACTTAATATT
        850        860        870        880        890        900
GGTTATTTTG GAGGTGAAAT TGGTGCAAGA TTGACATTTT AA........ ..........
```

Fig. 25A

```
         10         20         30         40         50         60
MNNKLKFTII NTVLVCLLSL PNISSSKAIN NNAKKYYGLY ISGQYKPSVS VFSNFSVKET
         70         80         90        100        110        120
NVITKNLIAL KKDVDSIETK TDASVGISNP SNFTIPYTAV FQDNSVNFNG TIGYTFAEGT
        130        140        150        160        170        180
RVEIEGSYEE FDVKNPGGYT LSDAYRYFAL AREMKGNSFT PKEKVSNSIF HTVMRNDGLS
        190        200        210        220        230        240
IISVIVNVCY DFSLNNLSIS PYICGGAGVD AIEFFDVLHI KFAYQSKLGI AYSLPSNISL
        250        260        270        280        290        300
FASLYYHKVM GNQFKNLNVQ HVAELASIPK ITSAVATLNI GYFGGEIGAR LTF.......
```

Fig. 25B

```
          10         20         30         40         50         60
ATGGCAAATT TTATGTACAA AAAATACAAA CTAATGACAG CAGGTGTAGT ATTATTTCAC
          70         80         90        100        110        120
ATGTTATTTC TACCTCATGT TTCTTTCGCA AAAAATACAA ACAGCAATAA ACTTGGATTA
         130        140        150        160        170        180
TACATCAGTG ACAGTATAA CCCTAGTGTT TCTGTTTTA GCAATTTTTC AGCAAAAGAA
         190        200        210        220        230        240
ACCAATGTTC ATACAGTACA ACTCATGGCG CTTAAAAAG ACATTGATTC TATTGAAGTT
         250        260        270        280        290        300
GATACTGGAA ATAGCGCAGG TATTAGCAAA CCACAAAATT TCACAGTTCT TTATACTCCA
         310        320        330        340        350        360
AAATTTCAAG ATAATGTTGC TGGTCTTAGC GGTGCACTTG GATTCTTTTA TTCTAAAGGA
         370        380        390        400        410        420
TTAAGGATTG AAATGGGGTT TTCTTATGAA AAATTTGATG CTAAAGACCT TGGTGAGTAC
         430        440        450        460        470        480
ACCAAAATAA AAGATGCTTA TAGATATTTT GCTCTAGTAC GTGAAATGCA TGTTAGTCTC
         490        500        510        520        530        540
ATTTATCCAA AAGATAATAA CACAGGAACA CATTATACTG TTATGAGAAA TGATGGTATA
         550        560        570        580        590        600
TCTATTTCTT CTGCTACAGT AAATGGCTGC TATGATTCTT TTTTCCAGTT TATCTTTGTC
         610        620        630        640        650        660
ACCTATATGT GTATAGGCAT CGGTATAGAT GCTATAGAAT TCTTAATGC ATACATATTA
         670        680        690        700        710        720
AGTTTGCTTG CCAAGGTAGT TAAGTGTTTA ACTPATTCTG TATCTCCCAA TGTTAATTTA
         730        740        750        760        770        780
TTTGCAGATG GATATTATCA TAAAGTGATG GGCAATAAAT TTAAAAATTT ACCTGTTCAA
         790        800        810        820        830        840
TACGTTAATA CTTTAGAAGA GTATCCAAGA GTTACATCTG CAATTGCTAC ACTTGATATT
         850        860        870        880        890        900
GGCTACCTCG GTGGTGAAAT TGGCATAAGA TTTATATTTT AA........ ..........
```

Fig. 26A

```
          10         20         30         40         50         60
MANFMYKKYK LMTAGVVLFH MLFLPHVSFA KNTDSNKLGL YISGQYNPSV SVFSNFSAKE
          70         80         90        100        110        120
TNVHTVQLMA LKKDIDSIEV DTGNSAGISK PQNETVLYTP KFQDNVAGLS GALGFFYSKG
         130        140        150        160        170        180
LRIEMGFSYE KFDAKDLGEY TKIKDAYRYF ALVREMHVSL IYPKDNNTGT HYTVMRNDGI
         190        200        210        220        230        240
SISSATVNGC YDSFFQFIFV TYMCIGIGID AIEFLNAYIL SLLAKVVKVL TYSVSPNVNL
         250        260        270        280        290        300
FADGYYHKVM GNKFKNLPVQ YVNTIEEYPR VTSAIATLDI GYLGGEIGIR FIF.......
```

Fig. 26B

```
         10         20         30         40         50         60
ATGGGAAATT CTATGAATAA TAAAAGTCAA TTCTTAATAA GATTTATATT TTTAACATGC
         70         80         90        100        110        120
ATGCTGTCAT TACCTAATAT ATCTCCTTCA AAAGTAAATA ACGAAAAACA TTCTGGTTTG
        130        140        150        160        170        180
TATATTAGCG GGCAATACAA ACCCAGTGTT TCTGTTTTCA GTAATTTTTC AGTTAAAGAA
        190        200        210        220        230        240
ACCAACTTTC ATACAAAACA TCTCATAGCT CTTAAACAAG ATGTTGATTC TGTTGAAATT
        250        260        270        280        290        300
GATACTGGTA GTAATACAGC AGGTATTAGT AACCCATCTA ACTTTACAAT CCCTTATACT
        310        320        330        340        350        360
GCAGAATTTC AAGACAACCA TACTAACTGC AATGGCTCTA TTGGTTATGC TTTTGCTGAA
        370        380        390        400        410        420
GGTCCAAGAA TTGAAATAGA ATTATCATAT GAAAAATTTG ATGTTAAAAA TCCCACAGGG
        430        440        450        460        470        480
TATACTACAG TAAAAGATGC TTATAGATAC TTTGCTTTAG CACGTGAAAT AAATATTTCT
        490        500        510        520        530        540
CTATTCCAAC CAAAACAAAA AGAAGGTAGT GGAATTTACC ATGTCGTAAT GAAAAACGAT
        550        560        570        580        590        600
GGGTTATCTA TCTTATCCAA TATAGTTAAT ATTTGCTACG ATTTTCTTT AAATAATTTA
        610        620        630        640        650        660
CCTATATCAC CTTATTTATG CGGAGGAATG GGTATAAATG CCATAGAATT CTTTGACGCT
        670        680        690        700        710        720
TTACATGTGA AATTTGCTTA TCAAAGCAAG GCAGGAATTA GTTATCAACT ATTACGTAAA
        730        740        750        760        770        780
ATCAACTTAT TTATTGATGT ATATTACTAC GAAGTAATAA GTAATAAATT TAAAAACCTG
        790        800        810        820        830        840
AAAGTCCAAC ATGTACATGA ACTTAAAGAT AATCCAAAAG TCACATCTGC AGTTGCTACA
        850        860        870        880        890        900
CTTGATATAG CATATTTTGG TAGTGAAGCT GGCATAAGAA TTATATTTA A.........
```

Fig. 27A

```
         10         20         30         40         50         60
MGNSMNNKSQ FLIRFIFLTC MLSLPNISLS KVNNEKHSGL YISGQYKPSV SVFSNFSVKE
         70         80         90        100        110        120
TNFHTKHLIA LKQDVDSVEI DTGSNTAGIS NPSNFTIPYT AEFQDNHTNC NGSIGYAFAE
        130        140        150        160        170        180
GPRIEIELSY EKFDVKNPTG YTTVKDAYRY FALAREINIS LFQPKQKEGS GIYHVVMKND
        190        200        210        220        230        240
GLSILSNIVN ICYDFSLNNL PISPYLCGGM GINAIEFFDA LHVKFAYQSK AGISYQLLRK
        250        260        270        280        290        300
INLFIDVYYY EVISNKFKNL KVQHVHELKD NPKVTSAVAT LDIAYFGSEA GIRIIF....
```

Fig. 27B

```
         10          20          30          40          50          60
ATGAATAGCA  AGAGTAAGTT  CTTTACAATA  TGTACATCGT  TAATATGCTT  ATTATCATCA
         70          80          90         100         110         120
CCTAACACAT  CTCTCTCAAA  CTTCATAGGC  AATAGTACAA  AACATTCTGG  ATTATATGTT
        130         140         150         160         170         180
AGCGGACAAT  ATAAGCCCAG  CGTTTCCATT  TTTAGCAAAT  TTTCAGTAAA  AGAAACAAAT
        190         200         210         220         230         240
ACACATACAG  TACAGTTAGT  AGCTCTTAAA  AAAGATGTTA  ATTCTATTTC  TATGAACATC
        250         260         270         280         290         300
AGTAATGGTG  CTACAGGCAT  TAGCAAAGCA  ACAAATTTTA  ATCTTCCTTA  TGTTGCAGAA
        310         320         330         340         350         360
TTTCAAGACA  ATGCCTTCAA  CTTCAGTGGA  GCTATTGGTT  ATTCACTTTT  TGAACAACTA
        370         380         390         400         410         420
AACATTGAAG  TTGAAGGTTC  TTATGAAGAA  TTCGATGCCA  AAAATCCTGG  TGGTTATATT
        430         440         450         460         470         480
TTAAATGATG  CATTCCGCTA  TTTTGCATTG  GCACGTGAAA  TGGGACAAGA  AAAAAATGAT
        490         500         510         520         530         540
AATAAGCATC  TTAGTCCTAA  GGAGGAGCAT  GATATAAGTA  AACATATTA   CACAGTCATG
        550         560         570         580         590         600
AGAAATAATG  GGTTATCTAT  ATTATCTATT  ATGATAAATG  GCTGCTATAA  TCTACCTCTC
        610         620         630         640         650         660
AATGATTTAT  CAATATCACC  TTATTTTGT   ACAGGAATAG  GTGTAGATGC  TATAGAATTT
        670         680         690         700         710         720
TTTGATGCAC  TGCATCTTAA  ACTTGCTTTG  CAAAGTAAAA  TAGGAGCTAC  TTACCAATTA
        730         740         750         760         770         780
TCAGACAACA  TTAGTTTATT  TACAAATGGA  TATTACCATC  AAGTAATAGG  TGATCAATTT
        790         800         810         820         830         840
AAAAACTTAA  AAGTCCAATA  TATAGGTGAA  CTTAAAGAGA  ACCCGAAAAT  TACATCTGCA
        850         860         870         880         890         900
GTTGCTACTC  TCAATGTTGG  ATACTTTGGA  GGTGAAATTG  GAGTAAGACT  CACACTTTAA
        910         920         930         940         950         960
..........  ..........  ..........  ..........  ..........  ..........
```

Fig. 28A

```
         10          20          30          40          50          60
MNSKSKFFTI  CTSLICLLSS  PNTSLSNFIG  NSTKHSGLYV  SGQYKPSVSI  FSKFSVKETN
         70          80          90         100         110         120
THTVQLVALK  KDVNSISMNI  SNGATGISKA  TNENLPYVAE  FQDNAFNFSG  AIGYSLFEQL
        130         140         150         160         170         180
NIEVEGSYEE  FDAKNPGGYI  LNDAFRYFAL  AREMGQEKND  NKHLSPKEEH  DISKTYYTVM
        190         200         210         220         230         240
RNNGLSILSI  MINGCYNLPL  NDLSISPYFC  TGIGVDAIEF  FDALHLKLAL  QSKIGATYQL
        250         260         270         280         290         300
SDNISLFTNG  YYHQVIGDQF  KNLKVQYIGE  LKENPKITSA  VATLNVGYFG  GEIGVRLTL.
```

Fig. 28B

```
         10         20         30         40         50         60
ATGAATAATA AAAGAAATTT TTTTTTAATA GGTATGTCTC TATTGATAAA TCTACTATTG
         70         80         90,       100        110        120
CCAATTGATG CCTCTTCTAT GGAAGTACAT AATTATACAC ATTTTACACC TAGGCTGTAT
        130        140        150        160        170        180
ATTAGTGGGC AATACAGGCC AGGAGTTTCC CACTTTAGCA AATTTTCAGT CAAAGAAACA
        190        200        210        220        230        240
CATTGTAATA CTGTGCAATT AGTTGGGCTA ACAAAAGATA TAAAAGTAAC TAATAACAGT
        250        260        270        280        290        300
AGTATCAACA CAAATACTAG TTTTAACTTT CCTTATGTTG CAGAATTTCA AGATAACGCA
        310        320        330        340        350        360
ATGAGCTTTA GTGGAGCAAT AGGATGCTTT TATTCAGAAC ACTTCAGAAT TGAAGTAGAA
        370        380        390        400        410        420
GCTTCTTATG AAGAATTTGA CGTTAAAAAT CCTGAAGGAT CTACTACAGA CTCCTATAGA
        430        440        450        460        470        480
TATTTCGCGT TAGCACGTGG CATGGATGGT AATAATATTC CTACAAGTCA AAAATTTACT
        490        500        510        520        530        540
GTAATGAGAA ACGACGGGTT ATTAATCTCA TCTGTTATGA TAAATGGCTG TTACAATGTC
        550        560        570        580        590        600
ATACTAAATG ATATACAAGC AGAACCTTAC ATATGTGCAG GACTAGGAGG AGATTTTATA
        610        620        630        640        650        660
GAATTCTTCA ATGGCTTTCA TGTTAAGCTA GCTTATCAAG GTAAAGTAGG CATTAGTTAT
        670        680        690        700        710        720
CAAATATTCC CTGAAGTAAG ATTATTTATT GATGGATACT ACCATAAAGT AAAAGGCAAC
        730        740        750        760        770        780
AAGTTTAAAA ATTTACACGT TCAACATGTA GGTGCACTTG CAGCACTCCC TAAAGTTACA
        790        800        810        820        830        840
TCTGCAGTTG CAACACTTAA TATTGGATAC TTTGGTTGTG AAGCTGGAGT AAGATTCATA
        850        860        870        880        890        900
TTTTAA....  ........   ........   ........   ........   ........
```

Fig. 29A

```
         10         20         30         40         50         60
MNNKRNFFLI GMSLLINLLL PIDASSMEVH NYTHFTPRLY ISGQYRPGVS HFSKFSVKET
         70         80         90        100        110        120
HCNTVQLVGL TKDIKVTNNS SINTNTSFNF PYVAEFQDNA MSFSGAIGCF YSEHFRIEVE
        130        140        150        160        170        180
ASYEEFDVKN PEGSTTDSYR YFALARGMDG NNIPTSQKFT VMRNDGLLIS SVMINGCYNV
        190        200        210        220        230        240
ILNDIQAEPY ICAGLGGDFI EFFNGFHVKL AYQGKVGISY QIFPEVRLFI DGYYHKVKGN
        250        260        270        280        290        300
KFKNLHVQHV GALAALPKVT SAVATLNIGY FGCEAGVRFI F........  ..........
```

Fig. 29B

```
          10         20         30         40         50         60
ATGAATTATA AGAAAATTCT AGTAAGAAGC GCGTTAATCT CATTAATGTC AATCTTACCA
          70         80         90        100        110        120
TATCAGTCTT TTGCAGATCC TGTAGGTTCA AGAACTAATG ATAACAAAGA AGGCTTCTAC
         130        140        150        160        170        180
ATTAGTGCAA AGTACAATCC AAGTATATCA CACTTTAGAA AATTCTCTGC TGAAGAAACT
         190        200        210        220        230        240
CCTATTAATG GAACAAATTC TCTCACTAAA AAAGTTTTCG GACTAAAGAA AGATGGTGAT
         250        260        270        280        290        300
ATAACAAAAA AAGACGATTT TACAAGAGTA GCTCCAGGCA TTGATTTTCA AAATAACTTA
         310        320        330        340        350        360
ATATCAGGAT TTTCAGGAAG TATTGGTTAC TCTATGGACG GACCAAGAAT AGAACTTGAA
         370        380        390        400        410        420
GCTGCATATC AACAATTTAA TCCAAAAAAC ACCGATAACA ATGATACTGA TAATGGTGAA
         430        440        450        460        470        480
TACTATAAAC ATTTTGCATT ATCTCGTAAA GATGCAATGG AAGATCAGCA ATATGTAGTA
         490        500        510        520        530        540
CTTAAAAATG ACGGCATAAC TTTTATGTCA TTGATGGTTA ATACTTGCTA TGACATTACA
         550        560        570        580        590        600
GCTGAAGGAG TATCTTTCGT ACCATATGCA TGTGCAGGTA TAGGAGCAGA TCTTATCACT
         610        620        630        640        650        660
ATTTTTAAAG ACCTCAATCT AAAATTTGCT TACCAAGGAA AAATAGGTAT TAGTTACCCT
         670        680        690        700        710        720
ATCACACCAG AAGTCTCTGC ATTTATTGGT GGATACTACC ATGGCGTTAT TGGTAATAAA
         730        740        750        760        770        780
TTTGAGAAGA TACCTGTAAT AACTCCTGTA GTATTAAATG ATGCTCCTCA AACCACATCT
         790        800        810        820        830        840
GCTTCAGTAA CTCTTGACGT TGGATACTTT GGCGGAGAAA TTGGAATGAG GTTCACCTTC
         850        860        870        880        890        900
TAA....... .......... .......... .......... .......... ..........
```

Fig. 30A

```
          10         20         30         40         50         60
MNYKKILVRS ALISLMSILP YQSFADPVGS RTNDNKEGFY ISAKYNPSIS HFRKFSAEET
          70         80         90        100        110        120
PINGTNSLTK KVFGLKKDGD ITKKDDFTRV APGIDFQNNL ISGFSGSIGY SMDGPRIELE
         130        140         50        160        170        180
AAYQQFNPKN TDNNDTDNGE YYKHFALSRK DAMEDQQYVV LKNDGITFMS LMVNTCYDIT
         190        200        210        220        230        240
AEGVSFVPYA CAGIGADLIT IFKDLNIKFA YQGKIGISYP ITPEVSAFIG GYYHGVIGNK
         250        260        270        280        290        300
FEKIPVITPV VLNDAPQTTS ASVTLDVGYF GGEIGMRFTF .......... ..........
```

Fig. 30B

```
          10         20         30         40         50         60
ATGAACAAAA AGAAAATTAT TACAGTAGGA ACAACATTAG CTTATTTATT ATTATCACCT
          70         80         90        100        110        120
AACATATCTT TTTCAGAAGT AATCAACAAT GATACTGATA AATATTCTAG ACTATATATA
         130        140        150        160        170        180
AGTGGTCAAT ATAAACCAGG ATTTTCTTAT TTTAATAAGT TCTCAGTTAG AGAAACTGAT
         190        200        210        220        230        240
CATTTCACTA AAGCATTAAT AGGATTAAGA CATGACGCAA TATCTACTAA AAATTTAACA
         250        260        270        280        290        300
ACTAATACAG ATTTCAATAC TCTTTATAAA GTAACATTTC AAAACAACAT CATTAGCTTT
         310        320        330        340        350        360
AGCGGTGCTA TTGGTTATTC TGATAGCACA GGTGTAAGGT TTGAGCTAGA AGGCTCTTAT
         370        380        390        400        410        420
GAAGAGTTCG ATGTTACAGA CCCTGGAGAT TGTATAATAA AGATACTTA CAGGTACTTT
         430        440        450        460        470        480
GCATTAGCTA GAAAAACAAG TGGTAATCAT CCCAACGATA ATGGGGAATA TACTGTCATG
         490        500        510        520        530        540
AGAAATGATG GAGTATCCAT TACCTCCGTT ATATTCAATG GTTGTTATGA TCTCTCTTTA
         550        560        570        580        590        600
AAAGAGCTAG AAATATCACC ATATGTTTGC ATTGGTATCG GAGGAGACTT TATAGAATTT
         610        620        630        640        650        660
TTTGATGCTT TACACATTAA ATTAGCATAT CAAGGTAAAC TAGGTATTAG CTATTCTTTT
         670        680        690        700        710        720
TCCACTAGAA CAAATTTATT TATCGATTGT TATTACCATA GAGTTATAGG TAATCAATTT
         730        740        750        760        770        780
AATAATTTAA ATGTTCAACA TGTAGTTGAG CTTACAGAAG CACCTAAAGC TACATCTGCA
         790        800        810        820        830        840
ATTGCTACAC TTAATGTTAG TTACTTCGGT GGAGAAGTTG GAATTAGACT TATGTTTTAA
         850        860        870        880        890        900
.......... .......... .......... .......... .......... ..........
```

Fig. 31A

```
          10         20         30         40         50         60
MNKKKIITVG TTLAYLLLSP NISFSEVINN DTDKYSRLYI SGQYKPGFSY FNKFSVRETD
          70         80         90        100        110        120
HFTKALIGLR HDAISTKNLT TNTDFNTLYK VTFQNNIISF SGAIGYSDST GVRFELEGSY
         130        140        150        160        170        180
EEFDVTDPGD CIIKDTYRYF ALARKTSGNH PNDNGEYTVM RNDGVSITSV IFNGCYDLSL
         190        200        210        220        230        240
KELEISPYVC IGIGGDFIEF FDALHIKLAY QGKLGISYSF STRTNLFIDC YYHRVIGNQF
         250        260        270        280        290        300
NNLNVQHVVE LTEAPKATSA IATLNVSYFG GEVGIRLMF. .......... ..........
```

Fig. 31B

```
         10         20         30         40         50         60
CCCGTCGTTT CTCATTACAG TGACTTTTCA ATTAAAGAAA CTTATACTAA CACTGAGGCA
         70         80         90        100        110        120
TTGTTTGGGC TAAAACAAGA TATTAGTTCT ATTTTACGTA ATAAAGAGAC CACACAATAT
        130        140        150        160        170        180
AATAACAATT TTAACGTTCC CTATACTGCA AAATTTCAAG ACGACTTTGC GAGTTTCAGC
        190        200        210        220        230        240
ATAGCTGTTG GATATATTGC TAACAATGGT CCAAGAATTG AAATAGAAGG ATCTTACGAA
        250        260        270        280        290        300
GAATTTGATG TTAAAAACCC AGGAAATTAT ACAACAATAG ATGCTCATAG GTACATTGCT
        310        320        330        340        350        360
TTAGCTAGAG AAAAAACTTC TTACTATCTA AGTTCTCCTA AAGAAAACAA ATATGTAATT
        370        380        390        400        410        420
ATAAAGAATA ACGGCATATC TATTGTATCT ATTATAATTA ATGGTTGTTA TGATATTTCT
        430        440        450        460        470        480
TTAAATGATT CTAAGGTGTC ACCTTACATA TGCACAGGGT TTGGTGGAGA TTTTATAGAG
        490        500        510        520        530        540
TTTTTTAGTG CTATACGTTT TAACTTTGCT TATCAAGGTA AAATAGGTAT CAGTTATTCA
        550        560        570        580        590        600
TTATCTTCTA ACATAATTTT ATTTACTGAT GGATATTACC ACAAGGTAAT AAATTCCCAA
        610        620        630        640        650        660
TTTAAAAATT TAAATGTTGA ACATGTTGTT AATGAGTTAA CTACAGATCC TAAAGTGACT
        670        680        690        700        710        720
TCTGCAACAG CATTTCTTAA TATTGAGTAT TTTGGTGGTG AATTTGGATT AAAATTTATA
        730        740        750        760        770        780
TTTTAA.... .......... .......... .......... .......... ..........
```

Fig. 32A

```
         10         20         30         40         50         60
PVVSHYSDFS IKETYTNTEA LFGLKQDISS ILRNKETTQY NNNFNVPYTA KFQDDFASFS
         70         80         90        100        110        120
IAVGYIANNG PRIEIEGSYE EFDVKNPGNY TTIDAHRYIA LAREKTSYYL SSPKENKYVI
        130        140        150        160        170        180
IKNNGISIVS IIINGCYDIS LNDSKVSPYI CTGFGGDFIE FFSAIRFKFA YQGKIGISYS
        190        200        210        220        230        240
LSSNIILFTD GYYHKVINSQ FKNLNVEHVV NELTTDPKVT SATAFLNIEY FGGEFGLKFI
        250        260        270        280        290        300
F......... .......... .......... .......... .......... ..........
```

Fig. 32B

```
          10         20         30         40         50         60
ATGAATCACA AAAGTATGCT CTTTACAATA GGTACAGCTT TGATATCCTT ATTGTCATTA
          70         80         90        100        110        120
CCTAATGTAT CATTCTCAGG AATCATAAAT AACAATGCTA ACAATTTAGG TATATACATT
         130        140        150        160        170        180
AGTGGGCAAT ATAAACCCAG TGTTTCTGTT TTTAGCAATT CTCAGTAAAA GAAACTAAC
         190        200        210        220        230        240
TTCACTACAC AACAGTTAGT AGCACTTAAA AAAGATATTG ATTCTGTTGA CATTAGTACC
         250        260        270        280        290        300
AATGCTGATA GCGGTATTAA TAATCCGCAG AATTTCACTA TCCCTTATAT ACCAAAATTT
         310        320        330        340        350        360
CAAGACAATG CTGCTAGTTT TAGTGGAGCA CTTGGATTCT TCTACGCTAG AGGTTTAAGA
         370        380        390        400        410        420
CTTGAAATGG AAGGTTCCTA TGAAGAATTT GATGTTAAAA ACCCTGGAGG ATATACAAAA
         430        440        450        460        470        480
GTAAAAGATG CATATCGTTA CTTTGCCCTG GCACGTGAGA TGCAATCTGG TCAAACTTGC
         490        500        510        520        530        540
CCTAAACACA AAGAAACATC AGGTATTCAA CCTCACGGTA TTTATCACAC TGTTATGAGG
         550        560        570        580        590        600
AATGATGGGG TATCTATTTC ATCTGTCATA ATCAATGGTT GTTATAACTT TACTTTAAGT
         610        620        630        640        650        660
AATCTACCAA TATCACCTTA CATGTGTGTA GGTATGGGAA TAGATGCTAT ACAATTTTTT
         670        680        690        700        710        720
GATTCACTAC ATATTAAGTT TGCACATCAA AGTAAGTTAG GTATTACTTA CCCACTATCT
         730        740        750        760        770        780
TCAAATGTTC ATTTATTTGC TGATAGCTAT TATCATAAAG TAATAGGTAA TAAATTTAAA
         790        800        810        820        830        840
AATCTAAGGG TTCAACACGT TTATGAATTA CAACAGGTAC CTAAAGTTAC ATCTGCTGTT
         850        860        870        880        890        900
GCTACACTTG ATATTGGGTA TTTTGGTGGT GAAGTTGGAG TAAGGTTTAT ACTTTAA...
```

Fig. 33A

```
          10         20         30         40         50         60
MNHKSMLFTI GTALISLLSL PNVSFSGIIN NNANNLGIYI SGQYKPSVSV FSNFSVKETN
          70         80         90        100        110        120
FTTQQLVALK KDIDSVDIST NADSGINNPQ NFTIPYIPKF QDNAASFSGA LGFFYARGLR
         130        140        150        160        170        180
LEMEGSYEEF DVKNPGGYTK VKDAYRYFAL AREMQSGQTC PKHKETSGIQ PHGIYHTVMR
         190        200        210        220        230        240
NDGVSISSVI INGCYNFTLS NLPISPYMCV GMGIDAIQFF DSLHIKFAHQ SKLGITYPLS
         250        260        270        280        290        300
SNVHLFADSY YHKVIGNKFK NLRVQHVYEL QQVPKVTSAV ATLDIGYFGG EVGVRFIL..
```

Fig. 33B

```
                                                      SV
                                                 ▼━━━━━━━━━
OMP-1F   MNCKKFFITT TLVSLMSFLP GISFSDAVQN DNVG-GN--- -FYISGKYVP
OMP-1E   .......... A......... ......P..G ..IS-..--- -...V....M.
OMP-1D   ...E...... A.TL...... ...L..P..D ..IS-..--- -........M.
OMP-1C   .......... A.ALP..... ..LL.EP..D .S.S-..--- -........M.
OMP-1B   ..Y..I.VSS A.I....I.. YQ..A.P.TS NDT.INDSRE G....V...N.
P28      ---------- ---------- ------PA-G SGIN-..--- -........M.
MAP-1    .....I...S T.I..V.... .V....VI.E E.NPV.S--- -V...A..M.
                                                           HV1
                                                      ━━━━━━━━━
OMP-1F   SVSHFGVFSA KQ-----ERN TTTGVFGLKQ DWDGSTISKN SPENTFNVPN
OMP-1E   .A....M... .E-----.K. P.VALY.... ..E.-IS.SS HND.H..NKG
OMP-1D   .A........ .E-----... ..V....IE. ...RCV..RT TLSDI.T...
OMP-1C   .A........ .E-----.K. P.VALY.... ..N.-VSASS HADAD..NKG
OMP-1B   .I...RK... EEAPINGNTS I.KK.....K .------GDI AQSAN..RTD
P28      .A........ .E-----... ..V....... N....A..NS ..NDV.T.S.
MAP-1    TA....KM.I .E-----DSR D.KA.....K ....VKTPSG NTNSI.TEKD

OMP-1F   YSFKYENNPF LGFAGAVGYL MNGPRIELEM SYETFDVKNQ GNNYKNDAH-
OMP-1E   .......... ......I..S .G...V.F.V .......... ..........-
OMP-1D   .......L.. S.....I..S .D.......V ...A...... ........E..-
OMP-1C   .......... ......I..S .G.....F.V .......... .G.........-
OMP-1B   PALEFQ..LI S..S.SI..A .D.......A AYQK..A..P D..DT.SGDY
P28      .......... ......I..S .D.......V .......... ........E..-
MAP-1    .......... ..........S .......F.V .......R.P .G.........-
              HV2
         ━━━━━━━━━
OMP-1F   -KYYALTH-- NSGGKLSNAG DKFVFLKNEG LLDISLMLNA CYDVISEGIP
OMP-1E   -R.C..CQ-- -QDNSGIPKT S.Y.L..S.. .....F.... ...I.N.S..
OMP-1D   -R....S.LL GTETQIDG.. SAS...I... ...K.F.... ..........
OMP-1C   -R.C..DR-- -KASSTNATA SHY.L..... .......... ....V.....
OMP-1B   Y..FG.SR-- ----EDAI.D K.Y.V..... ITFM...V.T ...ITA..V.
P28      -R.C..SH-- ..AADM.S.S NN........ .....F.... ....VG....
MAP-1    -M.C.----L DTASSSTAGA TTS.MV...N .T........ ...IMLD.M.
```

Fig. 34A

```
OMP-1F  FSPYICAGVG  TDLISMFEAI  NPKISYQGKL  GLSYSISPEA  SVFVGGHFHK
OMP-1E  L.........  ........T.  ..........  ......N...  ...I......
OMP-1D  ........I.  I..V......  ..........  ....P.....  ...I......
OMP-1C  ..........  ..........  ..........  ......N...  ..........
OMP-1B  .I..A.....  A...NV.KDF  .L.F.....I  .I..P.T..V  .A.I..YY.G
P28     ........I.  ...V.M...T  ..........  ..........  ...I......
MAP-1   V...V...I.  ...V.VIN.T  ...L......  .I....N...  .I.I.....R
                                    HV3
                                ─────────────
OMP-1F  VIGNEFRDIP  AMIPSTSTLT  GN-HF----T  IVTLSVCHFG  VELGGRFNF
OMP-1E  ..........  TLKAFVTSS-  -ATPDL---A  ..........  I........
OMP-1D  ..........  T....E.A.A  .KGNYP---A  ....D.FY..  I.......QL
OMP-1C  .A.......S  TLKAFATPSS  AATPDL---A, T.........  .........
OMP-1B  ....N.NK..  VIT.VVLEGA  PQTTS----A  L..IDTGY..  G.V.V..T.
P28     ..........  TI..TG...A  .KGNYP---A  ..I.D.....  I......A.
MAP-1   ......K..A  TSKVF..SGN  ASSAVSPGFA  SAI.D.....  I.I....V.
```

OUTER MEMBRANE PROTEIN OF *EHRLICHIA CANIS* AND *EHRLICHIA CHAFFEENSIS*

CROSS-REFERENCE TO RELATED APPLICATIONS

This application is a divisional of the commonly assigned U.S. patent application Ser. No.: 09/314,701, filed on May 19,1999, now U.S. Pat. No. 6,544,517 which claims priority from U.S. Provisional Application No. 60/100,853 filed on Sep. 18, 1998.

This work was supported by grant RO1 AI33123 and RO1 AI40934 from National Institutes of Health. The government has certain rights in this invention.

BACKGROUND OF THE INVENTION

The ehrlichiae are obligate intracellular bacteria that infect circulating leucocytes. *Ehrlichia chaffeensis* infects the monocytes and macrophages in humans and causes human monocytic ehrlichiosis. The clinical manifestations of ehrlichiosis in humans are nonspecific and similar to Rocky Mountain spotted fever. The clinical manifestations include fever, chills, headache, myalgia or vomiting, and weight loss. Most patients have a history of tick exposure.

*Ehrlichia canis* infects and causes ehrlichiosis in animals belonging to the family Canidae. Canine ehrlichiosis consists of an acute and a chronic phase. The acute phase is characterized by fever, serous nasal and ocular discharges, anorexia, depression, and loss of weight. The chronic phase is characterized by severe pancytopenia, epistaxis, hematuria, blood in feces in addition to more severe clinical signs of the acute disease. If treated early during the course of the disease, dogs respond well to doxycycline. However, chronically infected dogs do not, respond well to the antibiotic. Therefore, early diagnosis is very important for treating canine ehrlichiosis.

The primary diagnostic test for diagnosing canine ehrlichiosis and human ehrlichiosis is the indirect fluorescent antibody (IFA) test. This test uses the etiologic agent *Ehrlichia canis* to diagnose canine ehrlichiosis. The IFA test uses *Ehrlichia chaffeensis* as antigen for diagnosing human ehrlichiosis. The IFA test has, however, serious limitations. The IFA test is subject to false positives because the antigens are made of whole infected cells which comprise many nonspecific proteins which will cross-react with sera from some patients. The IFA test is also subject to false negatives because IFA antigens are unstable and may become inactivated during storage. In addition the IFA test requires a special equipment to perform the test. For example, the IFA test requires a tissue culture system for growing the bacterium that are used to prepare the antigen slides, a fluorescent microscope, and trained persons to evaluate the serum reactivity to the bacterial antigen on the slide.

Tools which permit simpler, more rapid, and objective serodiagnosis of canine ehrlichiosis or human ehrlichiosis are desirable.

SUMMARY OF THE INVENTION

The present invention relates to improved diagnostic tools for veterinary and human use which are used for serodiagnosing ehrlichiosis in mammals, particularly in members of the Canidae family and in humans. The diagnostic tools are a group of outer membrane proteins of *E. chaffeensis* and variants thereof, referred to hereinafter as the "OMP proteins", a group of outer membrane proteins of *E. canis* and variants thereof referred to hereinafter as the "P30F proteins", and antibodies to the OMP proteins and the P30F proteins.

The OMP proteins of *E. chaffeensis* encompass OMP-1, OMP-1A, OMP1-B, OMP-1C, OMP1-D, OMP1-E, OMP1-F, OMP1-H, OMP-1R, OMP-1S, OMP-1T, OMP-1U, OMP-1V, OMP-1W, OMP-1X, OMP-1Y and OMP-1Z. The mature OMP-1 protein of *E. chaffeensis* has a molecular weight of about 27.7 kDa and comprises amino acid 26 through amino acid 281 of the sequence shown in FIG. 3B, SEQ ID NO: 2. The mature OMP-1B protein of *E. chaffeensis* has a molecular weight of about 28.2 kDa and comprises amino acid 26 through amino acid 283 of the sequence shown in FIG. 4B, SEQ ID NO: 4. The mature OMP-1C protein of *E. chaffeensis* has a molecular weight of about 27.6 kDa and comprises amino acid 26 through amino acid 280 of the sequence shown in FIG. 5B, SEQ ID NO: 6. The mature OMP-1D protein of *E. chaffeensis* has a molecular weight of about 28.7 and comprises amino acid 26 through amino acid 286 of the sequence shown in FIG. 6B, SEQ ID NO: 8. The mature OMP-1E protein of *E. chaffeensis* has a molecular weight of about 27.8 kDa and comprises amino acid 26 through amino acid 278 of the sequence shown in FIG. 7B, SEQ ID NO: 10. The mature OMP-1F protein of *E. chaffeensis* has a molecular weight of about 27.9 kDa and comprises amino acid 26 through amino acid 280 of the sequence shown in FIG. 8B, SEQ ID NO: 12. The mature OMP-1A protein of *E. chaffeensis* has a molecular weight of about 29.6 kDa and comprises amino acid 31 through amino acid 297 of the sequence shown in FIG. 9B, SEQ ID NO: 14. The mature OMP-1R protein of *E. chaffeensis* has a molecular weight of about 19.7 kDa and comprises amino acid 29 through amino acid 196 of the sequence shown in FIG. 10B, SEQ ID NO: 16. The mature OMP-1S protein of *E. chaffeensis* has a molecular weight of about 29.2 kDa and comprises amino acid 26 through amino acid 291 of the sequence shown in FIG. 11B, SEQ ID NO: 18. The OMP-1T protein of *E. chaffeensis* comprises the amino acid sequence shown in FIG. 12B, SEQ ID NO: 20. The mature OMP-1U protein of *E. chaffeensis* has a molecular weight of about 30.6 kDa and comprises amino acid 26 through amino acid 295 of the sequence shown in FIG. 13B, SEQ ID NO: 22. The mature OMP-1V protein of *E. chaffeensis* has a molecular weight of about 28.0 kD and comprises amino acid 27 through amino acid 279 shown in FIG. 14B, SEQ ID NO: 24. The mature OMP-1W protein of *E. chaffeensis* has a molecular weight of about 28.8 kDa and comprises amino acid 30 through amino acid 283 of the sequence shown in FIG. 15B, SEQ ID NO: 26. The mature OMP-1X protein of *E. chaffeensis* has a molecular weight of about 27.8 kDa and comprises amino acid 25 through amino acid 275 of the sequence shown in FIG. 16B, SEQ ID NO: 28. The mature OMP-1Y protein of *E. chaffeensis* has a molecular weight about 28.8 kDa and comprises amino acid 28 through amino acid 285 of the sequence shown in FIG. 17B, SEQ ID NO: 30. The mature OMP-1Z protein of *E. chaffeensis* has a molecular weight of about 30.2 kDa and comprises amino acid 27 through amino acid 300 of the sequence shown in FIG. 18B, SEQ ID NO: 50. The mature OMP-1H protein has a molecular weight of about 30.2 kDa and comprises the amino acid 27 through amino acid 298 of sequence shown in FIG. 33B, SEQ ID NO: 52.

The outer membrane proteins from *E. chaffeensis*, particularly a recombinant form of OMP-1, are immunogenic and, thus are useful for preparing antibodies. Such antibodies are useful for immunolabeling isolates of *E. chaffeensis* and for detecting the presence of *E. chaffeensis* in body fluids, tissues, and particularly in monocytes and macrophages. The OMP proteins, particularly OMP-1, are also useful for detecting antibodies to *E. chaffeensis* in the blood of patients with clinical signs of ehrlichiosis. The OMP protein, particularly OMP-1, are also useful immunogens for raising antibodies that are capable of reducing the level of infection in an immunized mammal that has been infected with *E. chaffeensis*. The proteins are also useful in a vaccine for protecting against infection with *E. chaffeensis*.

The P30F proteins of *E. canis* encompass P30, P30a, P30-1, P30-2, P30-3, P30-4, P30-5, P30-6, P30-7, P30-8, P30-9, P30-10, P30-11, and P30-12. The mature P30 protein of *E. canis* has a molecular weight of about 28.8 kDa and comprises amino acid 26 through amino acid 288 of the sequence shown in FIG. 19B, SEQ ID NO: 32. The mature P30a protein of *E. canis* has a molecular weight of about 29.0 kDa and comprises amino acid 26 through amino acid 287 of the sequence shown in FIG. 20B, SEQ ID NO: 34. The mature P30-1 protein of *E. canis* has a molecular weight of about 27.7 kDa and comprises amino acid 55 through amino acid 307 of the sequence shown in FIG. 21B, SEQ ID NO: 36. The mature P30-2 protein of *E. canis* has a molecular weight of about 28.0 kDa and comprises amino acid 26 through amino acid 280 of the sequence shown in FIG. 22B, SEQ ID NO: 38. The mature P30-3 protein of *E. canis* has a molecular weight of about 28.7 kDa and comprises amino acid 26 through amino acid 283 of the sequence shown in FIG. 23B, SEQ ID NO: 40. The mature P30-4 protein of *E. canis* has a molecular weight of about 28.0 kDa and comprises amino acid 26 through amino acid 276 of the sequence shown in FIG. 24B, SEQ ID NO: 42. The mature P30-5 protein of *E. canis* has a molecular weight of about 29.4 kDa and comprises amino acid 27 through amino acid 293 of the sequence shown in FIG. 25B, SEQ ID NO: 44. The mature P30-6 protein of *E. canis* has a molecular weight of about 29.4 kDa and comprises amino acid 31 through amino acid 293 of the sequence shown in FIG. 26B, SEQ ID NO: 54. The mature P30-7 protein of *E. canis* has a molecular weight of about 29.9 kDa and comprises amino acid 31 through amino acid 296 of the sequence shown in FIG. 27B, SEQ ID NO: 56. The mature P30-8 protein of *E. canis* has a molecular weight of about 30.3 kDa and comprises amino acid 27 through amino acid 299 of the sequence shown in FIG. 28B, SEQ ID NO: 46. The mature P30-9 protein of *E. canis* has a molecular weight of about 28.6 kDa and comprises amino acid 27 through amino acid 281 of the sequence shown in FIG. 29B, SEQ ID NO: 58. The mature P30-10 protein of *E. canis* has a molecular weight of about 28.1 kDa and comprises amino acid 26 through amino acid 280 of the sequence shown in FIG. 30B, SEQ ID NO: 48. The mature P30-11 protein of *E. canis* has a molecular weight of about 28.6 kDa and comprises the amino acid 26 through amino acid 279 of sequence shown in FIG. 31B, SEQ ID NO: 60. The P30-12 protein of *E. canis* has a molecular weight of at least 27.3 kDa and comprises the amino acid sequence shown in FIG. 32B, SEQ ID NO: 62.

The P30F proteins, particularly P30, are immunogenic and are, thus, useful for preparing antibodies that are useful for immunolabeling isolates of *E. canis*. The P30 protein is also useful for diagnosing canine ehrlichiosis in mammals, particularly in members of the family Canidae, most particularly in dogs and for diagnosing infections with *E. chaffeensis* in humans. The P30F proteins are also useful immunogens for raising antibodies that reduce the level of infection in an immunized mammal that has been infected with *E. canis*. The P30F protein are also useful in a vaccine for protecting animals against infection with *E. canis*.

The present invention also provides isolated polynucleotides that encode the *E. chaffeensis* OMP proteins and isolated polynucleotides that encode the *E. canis* P30F proteins. The present invention also relates to antibodies which are immunospecific for and bind to the OMP proteins and the P30F proteins. Such antibodies are useful for immunolabeling isolates of *E. chaffeensis* and *E. canis*. The present invention also relates to kits containing reagents for diagnosing human ehrlichiosis and canine ehrlichiosis and to immunogenic compositions containing one or more OMP proteins or P30F proteins.

BRIEF DESCRIPTION OF THE FIGURES

FIG. 1. shows the DNA sequence (SEQ ID NO: 1) and the amino acid sequence (SEQ ID NO: 2) encoded by the *E. chaffeensis* (p28) gene cloned in pCRIIp28. The N-terminal amino acid sequence of native OMP-1 protein (P28) determined chemically is underlined. Five amino acid residues at the N terminus of P28 which were not included in the p28 gene, are indicated by boldface. Arrows indicate annealing positions of the primer pair designed for PCR.

FIG. 3B shows one embodiment of the OMP-1 protein (SEQ ID NO: 2); FIG. 3A shows one embodiment of the OMP-1 polynucleotide (SEQ ID NO: 1).

FIG. 4B shows one embodiment of the OMP-1B protein (SEQ ID NO: 4); FIG. 4A shows one embodiment of the OMP-1B polynucleotide (SEQ ID NO: 1).

FIG. 5A shows one embodiment of the OMP-1C polynucleotide (SEQ ID NO: 5); FIG. 5B shows one embodiment of the OMP-1C protein (SEQ ID NO: 6).

FIG. 6B shows one embodiment of the OMP-1D protein (SEQ ID NO: 8); FIG. 6A shows one embodiment of the OMP-1D polynucleotide (SEQ ID NO: 7).

FIG. 7B shows one embodiment of the OMP-1E protein (SEQ ID NO: 10); FIG. 7A shows one embodiment of the OMP-1E polynucleotide (SEQ ID NO: 9).

FIG. 8B shows one embodiment of the OMP-1F protein (SEQ ID NO: 12); FIG. 8A shows one embodiment of the OMP-1F polynucleotide (SEQ ID NO: 11).

FIG. 9B shows one embodiment of the OMP-1A protein (SEQ ID NO: 14):; FIG. 9A shows one embodiment of the OMP-1A polynucleotide (SEQ ID NO: 13).

FIG. 10B shows one embodiment of a portion of the OMP-1R protein (SEQ ID NO: 16); FIG. 10A shows one embodiment of an OMP-1R polynucleotide (SEQ ID NO: 15) encoding such polypeptide.

FIG. 11B shows one embodiment of a portion of the OMP-1S protein (SEQ ID NO: 18); FIG. 11A shows one embodiment of the OMP-1S polynucleotide (SEQ ID NO: 17) encoding such polypeptide.

FIG. 12B shows one embodiment of a portion of the OMP-1T protein (SEQ ID NO: 20); FIG. 12A shows one embodiment of the OMP-1T polynucleotide encoding such polypeptide (SEQ ID NO: 19).

FIG. 13B shows one embodiment of the OMP-1U protein (SEQ ID NO: 22); FIG. 13A shows one embodiment of the OMP-1U polynucleotide (SEQ ID NO: 21).

FIG. 14B shows one embodiment of the OMP-1V protein (SEQ ID NO: 24); FIG. 14A shows one embodiment of the OMP-1V polynucleotide (SEQ ID NO: 23).

FIG. 15B shows one embodiment of the OMP-1W protein (SEQ ID NO: 26); FIG. 15A shows one embodiment of the OMP-1W polynucleotide (SEQ ID NO: 25).

FIG. 16B shows one embodiment of the OMP-1X protein (SEQ ID NO: 28); FIG. 16A shows one embodiment of the OMP-1X polynucleotide (SEQ ID NO: 27).

FIG. 17B shows one embodiment of the OMP-1Y protein (SEQ ID NO: 30); FIG. 17A shows one embodiment of the OMP-1Y polynucleotide (SEQ ID NO: 29).

FIG. 18B shows one embodiment of the OMP-1Z protein (SEQ ID NO: 50); FIG. 18A shows one embodiment of the OMP-1Z polynucleotide (SEQ ID NO: 49).

FIG. 19B shows one embodiment of the P30 protein (SEQ ID NO: 32); FIG. 19A shows one embodiment of the P30 polynucleotide (SEQ ID NO: 31).

FIG. 20B shows one embodiment of the P30a protein (SEQ ID NO: 34); FIG. 20A shows one embodiment of the p30a polynucleotide (SEQ ID NO: 33).

FIG. 21B shows one embodiment of the P30-1 protein (SEQ ID NO: 36); FIG. 21A shows one embodiment of the p30-1 polynucleotide (SEQ ID NO: 35).

FIG. 22B shows one embodiment of the P30-2 protein (SEQ ID NO: 38); FIG. 22A shows one embodiment of the p30-2 polynucleotide (SEQ ID NO: 37).

FIG. 23B shows one embodiment of the P30-3 protein (SEQ ID NO: 40); FIG. 23A shows one embodiment of the p30-3 polynucleotide (SEQ ID NO: 39).

FIG. 24B shows one embodiment of the P30-4 protein (SEQ ID NO: 42); FIG. 22A shows one embodiment of the p30-4 polynucleotide (SEQ ID NO: 41).

FIG. 25B shows one embodiment of the P30-5 protein (SEQ ID NO: 44); FIG. 22A shows one embodiment of the p30-5 polynucleotide (SEQ ID NO: 43).

FIG. 26B shows one embodiment of the P30-6 protein (SEQ ID NO: 54); FIG. 26A shows one embodiment of the p30-6 polynucleotide (SEQ ID NO: 53).

FIG. 27B shows one embodiment of the P30-7 protein (SEQ ID NO: 56); FIG. 27A shows one embodiment of the p30-7 polynucleotide (SEQ ID NO: 55).

FIG. 28B shows one embodiment of the P30-8 protein (SEQ ID NO: 46); FIG. 28A shows one embodiment of the p30-8 polynucleotide (SEQ ID NO: 45).

FIG. 29B shows one embodiment of a portion of the P30-9 protein (SEQ ID NO: 58); FIG. 29A shows one embodiment of the p30-9 polynucleotide (SEQ ID NO: 57).

FIG. 30B shows one embodiment of a portion of the P30-10 protein (SEQ ID NO: 48); FIG. 30A shows one embodiment of the p30-10 polynucleotide (SEQ ID NO: 47) encoding such protein.

FIG. 31B shows one embodiment of a portion of the P30-11 protein (SEQ ID NO: 60); FIG. 31A shows one embodiment of the p30-11 polynucleotide (SEQ ID NO: 59).

FIG. 32B shows one embodiment of a portion of the P30-12 protein (SEQ ID NO: 62); FIG. 32A shows one embodiment of the p30-12 polynucleotide (SEQ ID NO: 61).

FIG. 33B shows one embodiment of a portion of the OMP-1H protein (SEQ ID NO: 52); FIG. 33A shows one embodiment of the OMP-1H polynucleotide (SEQ ID NO: 51).

FIG. 34 depicts the amino acid sequences alignment of six *E. chaffeensis* OMP-1s and *Cowdria ruminantium* MAP-1. Aligned positions of identical amino acids with OMP-1F are shown with dots. The sequence of *C. ruminantium* MAP-1 is from the report of Van Vliet et al (1994) Molecular cloning, sequence analysis, and expression of the gene encoding the immunodominant 32-kilodalton protein of *Cowdria ruminantium*. Infect. Immun. 62:1451–1456. Gaps indicated by dashes were introduced for optimal alignment of all proteins. Bars indicate semivariable region (SV) and three hypervariable regions (HV1, HV2, and HV3).

DETAILED DESCRIPTION OF THE INVENTION

Figure 2:
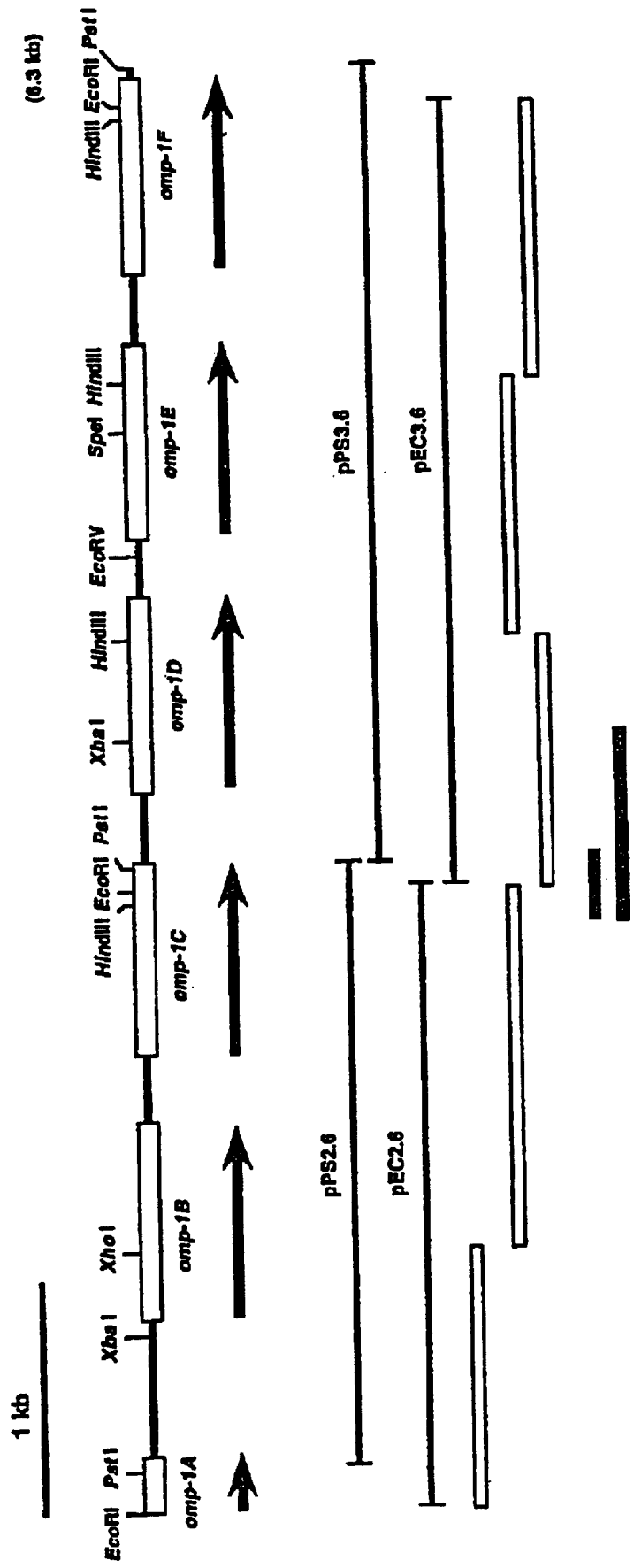
FIG. 2. shows the restriction map of 6.3-kb genomic DNA including the omp-1 gene copies in *E. chaffeensis*. The four DNA fragments were cloned from the genomic DNA (pPS2.6, pPS3.6, pEC2.6, and pEC3.6). A recombinant plasmid pPS2.6 has an overlapping sequence with that of pEC3.6. The closed boxes at the bottom show PCR-amplified fragments from the genomic DNA for confirmation of the overlapping area. Open boxes at the top indicate open reading frames (ORF) of omp-1 gene copies with direction by arrows. Open boxes at the bottom show DNA fragments subcloned for DNA sequencing.

The present invention provides a group of outer membrane proteins of *E. chaffeensis*, OMP proteins, and a group of outer membrane proteins of E. canis, the P30F proteins. The mature OMP-1 protein of *E. chaffeensis* has a molecular weight of about 27.7 kDa and comprises amino acid 26 through amino acid 281 of the sequence shown in FIG. 3B, SEQ ID NO: 2. The mature OMP-1B protein of *E. chaffeensis* has a molecular weight of about 28.2 kDa and comprises amino acid 26 through amino acid 283 of the sequence shown in FIG. 4B, SEQ ID NO: 4. The mature OMP-1C protein of *E. chaffeensis* has a molecular weight of about 27.6 kDa and comprises amino acid 26 through amino acid 280 of the sequence shown in FIG. 5B, SEQ ID NO: 6. The mature OMP-1D protein of *E. chaffeensis* has a molecular weight of about 28.7 and comprises amino acid 26 through amino acid 286 of the sequence shown in FIG. 6B, SEQ ID NO: 8. The mature OMP-1E protein of *E. chaffeensis* has a molecular weight of about 27.8 kDa and comprises amino acid 26 through amino acid 278 of the sequence shown in FIG. 7B, SEQ ID NO: 10. The mature OMP-1F protein of *E. chaffeensis* has a molecular weight of about 27.9 kDa and comprises amino acid 26 through amino acid 280 of the sequence shown in FIG. 8B, SEQ ID NO: 12. The mature OMP-1A protein of *E. chaffeensis* has a molecular weight of about 29.6 kDa and comprises amino acid 31 through amino acid 279 of the sequence shown in FIG. 9B, SEQ ID NO: 14. The mature OMP-1R protein of *E. chaffeensis* has a molecular weight of about 19.7 kDa and comprises the amino acid 29 through amino acid 196 of the sequence shown in FIG. 10B, SEQ ID NO: 16. The mature OMP-1S protein of *E. chaffeensis* has a molecular weight of about 29.2 kDa and comprises amino acid 26 through amino acid 291 of the sequence shown in FIG. 11B, SEQ ID NO: 18. The OMP-1T protein of *E. chaffeensis* comprises the amino acid sequence shown in FIG. 12B, SEQ ID NO: 20. The mature OMP-1U protein of *E. chaffeensis* has a molecular weight of about 30.6 kDa and comprises amino acid 26 through amino acid 295 of the sequence shown in FIG. 13B, SEQ ID NO: 22. The mature OMP-1V protein of *E. chaffeensis* has a molecular weight of about 28.0 kD and comprises amino acid 27 through amino acid 279 shown in FIG. 14B, SEQ ID NO: 24. The mature OMP-1W protein of *E. chaffeensis* has a molecular weight of about 28.8 kDa and comprises amino acid 30 through amino acid 283 of the sequence shown in FIG. 15B, SEQ ID NO: 26. The mature OMP-1X protein of *E. chaffeensis* has a molecular weight of about 27.8 kDa and comprises amino acid 25 through amino acid 275 of the sequence shown in FIG. 16B, SEQ ID NO: 28. The mature OMP-1Y protein of *E. chaffeensis* has a molecular weight about 28.8 kDa and comprises amino acid 28 through amino acid 285 of the sequence shown in FIG. 17B, SEQ ID NO: 30. The mature OMP-1Z protein of *E. chaffeensis* has a molecular weight of about 30.2 kDa and comprises amino acid 27 through amino acid 300 of the sequence shown in FIG. 18B, SEQ ID NO: 50. The mature OMP-1H protein has a molecular weight of about 30.2 kDa and comprises the amino acid 27 through amino acid 298 of sequence shown in FIG. 33B, SEQ ID NO: 52.

The mature P30 protein of E. canis has a molecular weight of about 28.8 kDa and comprises amino acid 26 through amino acid 288 of the sequence shown in FIG. 19B, SEQ ID NO: 32. The mature P30a protein of E. canis has a molecular weight of about 29.0 kDa and comprises amino acid 26 through amino acid 287 of the sequence shown in FIG. 20B, SEQ ID NO: 34. The mature P30-1 protein of E. canis has a molecular weight of about 27.7 kDa and comprises amino acid 55 through amino acid 307 of the sequence shown in FIG. 21B, SEQ ID NO: 36. The mature P30-2 protein of E. canis has a molecular weight of about 28.0 kDa and comprises amino acid 26 through amino acid 280 of the sequence shown in FIG. 22B, SEQ ID NO: 38. The mature P30-3 protein of E. canis has a molecular weight of about 28.7 kDa and comprises amino acid 26 through amino acid 283 of the sequence shown in FIG. 23B, SEQ ID NO: 40. The mature P30-4 protein of E. canis has a molecular weight of about 28.0 kDa and comprises amino acid 26 through amino acid 276 of the sequence shown in FIG. 24B, SEQ ID NO: 42. The mature P30-5 protein of E. canis has a molecular weight of about 29.4 kDa and comprises amino acid 27 through amino acid 293 of the sequence shown in FIG. 25B, SEQ ID NO: 44. The mature P30-6 protein of E. canis has a molecular weight of about 29.4 kDa and comprises amino acid 31 through amino acid 293 of the sequence shown in FIG. 26B, SEQ ID NO: 54. The mature P30-7 protein of E. canis has a molecular weight of about 29.9 kDa and comprises amino acid 31 through amino acid 296 of the sequence shown in FIG. 27B, SEQ ID NO: 56. The mature P30-8 protein of E. canis has a molecular weight of about 30.3 kDa and comprises amino acid 27 through amino acid 299 of the sequence shown in FIG. 28B, SEQ ID NO: 46. The mature P30-9 protein of E. canis has a molecular weight of about 28.6 kDa and comprises amino acid 27 through amino acid 281 of the sequence shown in FIG. 29B, SEQ ID NO: 58. The mature P30-10 protein of E. canis has a molecular weight of about 28.1 kDa and comprises amino acid 26 through amino acid 280 of the sequence shown in FIG. 30B, SEQ ID NO: 48. The mature P30-11 protein of E. canis has a molecular weight of about 28.6 kDa and comprises the amino acid 26 through amino acid 279 of sequence shown in FIG. 31B, SEQ ID NO: 60. The P30-12 protein of E. canis has a molecular weight of at least 27.3 kDa and comprises the amino acid sequence shown in FIG. 32B, SEQ ID NO: 62.

The present invention also encompasses variants of the OMP proteins shown in FIGS. 3–18 and 33 and variants of the P30F proteins shown in FIGS. 19–32. A "variant" as used herein, refers to a protein whose amino acid sequence is similar to one the amino acid sequences shown in FIGS. 3–33, hereinafter referred to as the reference amino acid sequence, but does not have 100% identity with the respective reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 95% identical to the reference sequence, preferably, at least 97% identical, more preferably at least 98% identical, most preferably at least 99% identical to the reference sequence. Variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) J. Mol. Biol. 215, 403–410. Identities are calculated by the Align program (DNAstar, Inc.) In all cases, internal gaps and amino acid insertions in the candidate sequence as aligned are not ignored when making the identity calculation.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The alterations are designed not to abolish the immunoreactivity of the variant protein with antibodies that bind to the reference protein. Guidance in determining which amino acid residues may be substituted, inserted or deleted without abolishing such immunoreactivity of the variant protein are found using computer programs well known in the art, for example, DNASTAR software. A variant of the OMP-1 protein is set forth in SEQ ID NO: 67 where the alanine at position 280 is replaced with a valine.

The present invention also encompasses fusion proteins in which a tag or one or more amino acids, preferably from about 2 to 65 amino acids, more preferably from about 34 to about 62 amino acids are added to the amino or carboxy terminus of the amino acid sequence of an OMP protein, a P30F protein, or a variant of such protein. Typically, such additions are made to stabilize the resulting fusion protein or to simplify purification of an expressed recombinant form of the corresponding OMP protein, P30F protein or variant of such protein. Such tags are known in the art. Representative examples of such tags include sequences which encode a series of histidine residues, the Herpes simplex glycoprotein D, or glutathione S-transferase.

The present invention also encompasses OMP proteins and P30F proteins in which one or more amino acids, preferably no more than 10 amino acids, in the respective OMP protein or P30F are altered by posttranslation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking gamma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

The OMP proteins, particularly a recombinant form of OMP-1, are immunogenic and, thus are useful for preparing antibodies. Such antibodies are useful for immunolabeling isolates of *E. chaffeensis* and for detecting the presence of *E. chaffeensis* in body fluids, tissues, and particularly in monocytes and macrophages. The OMP proteins, particularly OMP-1, are also useful for detecting antibodies to *E. chaffeensis* in the blood of patients with clinical signs of ehrlichiosis. The OMP proteins, particularly OMP-1, are also useful immunogens for raising antibodies that are capable of reducing the level of infection in an immunized mammal that has been infected with *E. chaffeensis*. The OMP proteins are also useful in a vaccine for protecting against infection with *E. chaffeensis*.

The P30F proteins, particularly recombinant forms of P30, are immunogenic and are, thus, useful for preparing antibodies that are useful for immunolabeling isolates of *E. canis*. The P30 protein is also useful for diagnosing canine ehrlichiosis in mammals, particularly in members of the family Canidae, most particularly in dogs and for diagnosing infections with *E. chaffeensis* in humans. The P30F proteins are also useful immunogens for raising antibodies that reduce the level of infection in an immunized mammal that has been infected with *E. canis*. The P30F proteins are also useful in a vaccine for protecting animals against infection with *E. canis*.

In another aspect, the present invention provides a polypeptide which comprises a fragment of the OMP1 protein, hereinafter referred to as "rOMP-1". The rOMP-1 polypeptide weighs approximately 31 kDa and comprises all but of the first 5 amino acids of mature OMP-1 protein. The rOMP-1 polypeptide comprises the amino acid sequence extending from amino acid 6 through amino acid 251 of the amino acid sequence shown in FIG. 1, SEQ ID NO. 2. The present invention also embraces polypeptides where one or more of the amino acids in the sequence extending from amino acid 1 or 6 through amino acid 251 FIG. 1 are replaced by conservative amino acid residues. The present invention also relates to variant of rOMP-1 that have an amino acid sequence identity of at least 95%, more preferably at least 97%, and most preferably of at least 99% with the amino acid sequence extending from amino acid 6 through amino acid 251 of the OMP-1 protein and which derivative binds to antibodies in sera from humans infected with *E. chaffeensis*.

Polynucleotides

The present invention also provides isolated polynucleotides which encode the OMP proteins and the P30F proteins. The OMP-1 polynucleotide encodes the OMP-1 protein of *E. chaffeensis*, FIG. 3A shows one embodiment of the OMP-1 polynucleotide, SEQ ID NO: 1. The OMP-1B polynucleotide encodes the OMP-1B protein of *E. chaffeensis*; FIG. 4A shows one embodiment of the OMP-1B polynucleotide, SEQ ID NO: 3. The OMP-1C polynucleotide encodes the OMP-1C protein of *E. chaffeensis*, FIG. 5A shows one embodiment of the OMP-1C polynucleotide; SEQ ID NO: 5. The OMP-1D polynucleotide encodes the OMP-1D protein of *E. chaffeensis*; FIG. 6A shows one embodiment of the OMP-1D polynucleotide, SEQ ID NO: 7. The OMP-1E polynucleotide encodes the OMP-1E protein of *E. chaffeensis*; FIG. 7A shows one embodiment of the OMP-1E polynucleotide, SEQ ID NO: 9. The OMP-1F polynucleotide encodes the OMP-1F protein of *E. chaffeensis*; FIG. 8A shows one embodiment of the OMP-1F polynucleotide, SEQ ID NO: 11. The OMP-1A polynucleotide encodes the OMP-1A protein of *E. chaffeensis*; FIG. 9A shows one embodiment of the OMP-1A polynucleotide, SEQ ID NO: 13. The OMP-1R polynucleotide encodes the OMP-1R protein, FIG. 10A shows one embodiment of a portion of the OMP-1R polynucleotide, SEQ ID NO: 15. The OMP-1S polynucleotide encodes the OMP-1S protein of *E. chaffeensis*; FIG. 11A shows one embodiment of a portion of the OMP-1S polynucleotide, SEQ ID NO: 17. The OMP-1T polynucleotide encodes the OMP-1T protein of *E. chaffeensis*; FIG. 12A shows one embodiment of a portion of the OMP-1T polynucleotide, SEQ ID NO: 19. The OMP-1U polynucleotide encodes the OMP-1U protein of *E. chaffeensis*; FIG. 13A shows one embodiment of the OMP-1U polynucleotide, SEQ ID NO: 21. The OMP-1V polynucleotide encodes the OMP-1V protein of *E. chaffeensis*; FIG. 14A shows one embodiment of the OMP-1V polynucleotide, SEQ ID NO: 23. The OMP-1W polynucleotide encodes the OMP-1W protein of *E. chaffeensis*; FIG. 15A shows one embodiment of the OMP-1W polynucleotide, SEQ ID NO: 25. The OMP-1X polynucleotide encodes an OMP-1X protein of *E. chaffeensis*; FIG. 16A shows one embodiment of the OMP-1X polynucleotide, SEQ ID NO 27. The OMP-1Y polynucleotide encodes the OMP-1Y protein of *E. chaffeensis*; FIG. 17A shows one embodiment of the OMP-1Y polynucleotide, SEQ ID NO 29. The OMP-1Z polynucleotide encodes the OMP-1Z protein of *E. chaffeensis*; FIG. 18A shows one embodiment of an OMP-1Z polynucleotide encoding such polypeptide, SEQ ID NO: 49. The OMP-1H polynucleotide encodes the OMP-1H protein of *E. chaffeensis*; FIG. 33A shows one embodiment of a portion of the OMP-1H polynucleotide, SEQ ID NO: 51.

The p30 polynucleotide encodes the P30 protein of *E. canis*, FIG. 19A shows one embodiment of the p30 polynucleotide, SEQ ID NO: 31. The p30a polynucleotide encodes the P30a protein of *E. canis*, FIG. 20A shows one embodiment of the p30a polynucleotide, SEQ ID NO: 33. The p30-1 polynucleotide encodes the P30-1 protein of *E. canis*; FIG. 21A shows one embodiment of the p30-1 polynucleotide, SEQ ID NO: 35. The p30-2 polynucleotide encodes the P30-2 protein of *E. canis*; FIG. 22A shows one embodiment of the p30-2 polynucleotide, SEQ ID NO: 37. The p30-3 polynucleotide encodes the P30-3 protein of E.canis; FIG. 23A shows one embodiment of the p30-3 polynucleotide, SEQ ID NO: 39. The p30-4 polynucleotide encodes the P30-4 protein of *E. canis*, FIG. 24A shows one embodiment of the p30-4 polynucleotide, SEQ ID NO: 41. The p30-5 polynucleotide encodes the P30-5 protein of *E. canis*, FIG. 25A shows one embodiment of the p30-5 polynucleotide, SEQ ID NO: 43. The p30-6 polynucleotide encodes the P30-6 protein, FIG. 26A shows one embodiment of the p30-6 polynucleotide, SEQ ID NO: 53. The p30-7 polynucleotide encodes the P30-7 protein of *E. canis*; FIG. 27A shows one embodiment of the p30-7 polynucleotide, SEQ ID NO: 55. The p30-8 polynucleotide encodes the P30-8 protein of *E. canis*; FIG. 28A shows one embodiment of the p30-8 polynucleotide, SEQ ID NO: 45. The p30-9 polynucleotide encodes the P30-9 protein of *E. canis*; FIG. 29A shows one embodiment of a portion of the p30-9 polynucleotide, SEQ ID NO: 57. The p30-10 polynucleotide encodes the P30-10 protein of *E. canis*, FIG. 30A shows one embodiment of a portion of the p30-10 polynucleotide, SEQ ID NO: 47. The p30-11 polynucleotide encodes the P30-11 protein of *E. canis*; FIG. 31A shows one embodiment of a portion of the p30-11 polynucleotide, SEQ ID NO: 59. The p30-12 polynucleotide encodes the P30-12 protein of *E. canis*; FIG. 32A shows one embodiment of a portion of the p30-12 polynucleotide, SEQ ID NO: 61.

The polynucleotides are useful for producing the outer membrane proteins of *E. chaffeensis* and *E. canis*. For example, an RNA molecule encoding the outer membrane protein OMP-1 is used in a cell-free translation systems to prepare OMP-1. Alternatively, a DNA molecule encoding the outer membrane protein is introduced into an expression vector and used to transform cells. Suitable expression vectors include for example chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, and pseudorabies. The DNA sequence is introduced into the expression vector by conventional procedures.

Accordingly, the present invention also relates to recombinant constructs comprising one or more of the polynucleotide sequences. Suitable constructs include, for example, vectors, such as a plasmid, phagemid, or viral vector, into which a sequence that encodes the outer membrane protein has been inserted. In the expression vector, the DNA sequence which encodes the outer membrane protein is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The promoter may also be the natural promoter of the outer membrane protein coding sequence. The expression vector also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e. cells that are expressing the heterologous DNA sequences. The polynucleotide sequence encoding the outer membrane protein is incorporated into the vector in frame with translation initiation and termination sequences. Optionally, the sequence encodes a fusion outer membrane protein which includes an N-terminal or C-terminal peptide or tag that stabilizes or simplifies purification of the expressed recombinant product. Representative examples of such tags include sequences which encode a series of histidine residues, the Herpes simplex glycoprotein D, or glutathione S-transferase.

Polynucleotides encoding the OMP proteins and the P30F proteins are also useful for designing hybridization probes for isolating and identifying cDNA clones and genomic clones encoding the OMP proteins, the P30F proteins or allelic forms thereof. Such hybridization techniques are known to those of skill in the art. The sequences that encode the OMP proteins and the P30F proteins are also useful for designing primers for polymerase chain reaction (PCR), a technique useful for obtaining large quantities of cDNA molecules that encode the OMP proteins and the P30F proteins.

Also encompassed by the present invention, are single stranded polynucleotides, hereinafter referred to as antisense polynucleotides, having sequences which are complementary to the DNA and RNA sequences which encode the OMP proteins and the P30F proteins. The term complementary as used herein refers to the natural binding of the polynucleotides under permissive salt and temperature conditions by base pairing, The present invention also encompasses oligonucleotides that are used as primers in polymerase chain reaction (PCR) technologies to amplify transcripts of the genes which encode the OMP proteins, the P30F proteins or portions of such transcripts. Preferably, the primers comprise 18–30 nucleotides, more preferably 19–25 nucleotides. Preferably, the primers have a G+C content of 40% or greater. Such oligonucleotides are at least 98% complementary with a portion of the DNA strand, i.e., the sense strand, which encodes the OMP protein or the P30F protein, or a portion of its corresponding antisense strand. Preferably, the primer has at least 99% complementarity, more preferably 100% complementarity, with such sense strand or its corresponding antisense strand. Primers which are which have 100% complementarity with the antisense strand of a double-stranded DNA molecule which encodes an OMP protein or a P30F protein have a sequence which is identical to a sequence contained within the sense strand. The identity of primers which are 15 nucleotides in length and have full complementarity with a portion of the antisense strand of a double-stranded DNA molecule which encodes the OMP-1 protein is determined using the nucleotide sequence, SEQ ID NO: 1, shown in FIG. 3A and described by the general formula a–b, where a is any integer between 1 to 843, where b is equal to a+14, and where both a and b correspond to the positions of nucleotide residues shown in SEQ ID NO: 1.

The present invention also encompasses oligonucleotides that are useful as hybridization probes for detecting transcripts of the genes which encode the OMP proteins and P30F proteins or for mapping of the genes which encode the OMP proteins and P30F proteins. Preferably, such oligonucleotides comprise at least 210 nucleotides, more preferably at least 230, most preferably from about 210 to 280 nucleotides. Such hybridization probes have a sequence which is at least 90% complementary with a sequence contained within the sense strand of a DNA molecule which encodes each of OMP proteins and P30F proteins or with a sequence contained within its corresponding antisense strand. Such hybridization probes bind to the sense strand under stringent conditions. The term "stringent conditions" as used herein is the binding which occurs within a range from about Tm 5° C. (5° C. below the melting temperature Tm of the probe) to about 20° C. to 25° C. below Tm. The probes are used in Northern assays to detect transcripts of OMP and P30F homologous genes and in Southern assays to detect OMP and P30F homologous genes. The identity of probes which are 200 nucleotides in length and have full complementarity with a portion of the antisense strand of a double-stranded DNA molecule which encodes the OMP-1 protein is determined using the nucleotide sequence, SEQ ID NO: 1, shown in FIG. 3A and described by the general formula a–b, where a is any integer between 1 to 843, b is equal to a+200, and where both a and b correspond to the positions of nucleotide residues shown in SEQ ID NO: 1.

The present invention also encompasses isolated polynucleotides which are alleles of the genes which encode the OMP proteins and the P30F proteins. As used herein, an allele or allelic sequence is an alternative form of the gene which may result from one or more mutations in the sequences which encode the OMP proteins and P30F proteins. Such mutations typically arise from natural addition, deletion or substitution of nucleotides in the open reading frame sequences. Any gene may have none, one, or several allelic forms. Such alleles are identified using conventional techniques, such as for example screening libraries with probes having sequences identical to or complementary with one or more OMP or P30F polynucleotides.

The present invention also encompasses altered polynucleotides which encode OMP proteins and P30F proteins.

Such alterations include deletions, additions, or substitutions. Such alterations may produce a silent change and result in an OMP protein or P30F protein having the same amino acid sequence as the OMP protein or P30F protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 3–33 to increase the rate of expression of the proteins encoded by such sequences. Such alterations may also introduce new restriction sites into the sequence or result in the production of an OMP protein variant or P30F protein variant. Typically, such alterations are accomplished using site-directed mutagenesis.

Antibodies

In another aspect, the present invention relates to antibodies which are specific for and bind to at least one OMP protein or P30F protein. Such antibodies are useful research tools for identifying cells, particularly monocytes or macrophages, infected with *E. chaffeensis* or *E. canis* and for purifying the major outer membrane protein of *E. chaffeensis* or *E. canis* from partially purified preparations by affinity chromatography. Such antibodies are also useful for identifying bacterial colonies, particularly colonies of genetically-engineered bacteria, that are expressing the major outer membrane protein of *E. chaffeensis* or *E. canis*.

Kits

The present invention also relates to kits containing reagents for diagnosing *E. chaffeensis* and *E. canis*. The kit comprises one or more OMP proteins, or one or more *E. canis* proteins, or antigenic fragments thereof. For ease of detection, it is preferred that the OMP protein or P30F proteins be attached to a substrate such as a column, plastic dish, matrix, or membrane, preferably nitrocellulose. The kit may further comprise a biomolecule, preferably a secondary antibody, for detecting interactions between the isolated OMP protein or P30F protein and antibodies in a patient sample. Preferably, the biomolecule is coupled to a detectable tag such as an enzyme, chromophore, fluorophore, or radio-isotope. The kit is used by contacting a patient sample with the OMP protein or P30F protein under conditions that permit formation of antigen-antibody complexes. Then the biomolecule is added and the presence or absence of any resulting antigen-antibody complexes is detected by assaying for a change in the sample, for example, by observing the formation of a precipitate in the sample, the presence of radioactivity on the substrate, or a color change in the sample or on the substrate.

Diagnostic Method

The present invention also provides a method for detecting antibodies to the *E. chaffeensis* or *E. canis* in a sample of a bodily fluid from a patient. The method comprises providing an isolated outer membrane protein of *E. chaffeensis* or *E. canis*, particularly a recombinant form of the isolated protein, contacting the outer membrane protein or polypeptide with a sample taken from the patient; and assaying for the formation of a complex between the outer membrane protein or polypeptide and antibodies in the sample. For ease of detection, it is preferred that the isolated protein or polypeptide be attached to a substrate such as a column, plastic dish, matrix, or membrane, preferably nitrocellulose. The sample may be a tissue or a biological fluid, including urine, whole blood, or exudate, preferably serum. The sample may be untreated, subjected to precipitation, fractionation, separation, or purification before combining with the isolated protein or peptide. Interactions between antibodies in the sample and the isolated protein or peptide are detected by radiometric, colorimetric, or fluorometric means, size-separation, or precipitation. Preferably, detection of the antibody-outer membrane protein complex is by addition of a secondary antibody that is coupled to a detectable tag, such as for example, an enzyme, fluorophore, or chromophore. Formation of the complex is indicative of the presence of anti-*E chaffeensis* or anti-*E canis* antibodies, either IgM or IgG, in the patient. Thus, the method is used to determine whether a patient is infected with *E. chaffeensis* or *E. canis*.

Preferably, the method employs an enzyme-linked immunosorbent assay (ELISA) or a Western immunoblot procedure. Such methods are relatively simple to perform and do not require special equipment as long as membrane strips are coated with a high quality antigen. Accordingly, it is more advantageous to use a recombinant form of the outer membrane protein of *E. chaffeensis* or *E. canis* since such proteins, typically, are more pure and consistent in quality than a purified form of such protein.

Immunogenic Composition

The present invention also relates to immunogenic compositions comprising one or more OMP protein of *E. chaffeensis* and a pharmaceutically acceptable adjuvant and to immunogenic compositions comprising one or more P30F proteins of *E. canis* and a pharmaceutically acceptable adjuvant, which, preferably, enhances the immunogenic activity of the outer membrane protein in the host animal.

Preparing the OMP Proteins and the P30F Proteins

The OMP proteins and P30F proteins may be produced by conventional peptide synthesizers. The OMP proteins and P30F proteins may also be produced using cell-free translation systems and RNA molecules derived from DNA constructs that encode the OMP proteins and P30F proteins. Alternatively, OMP proteins and P30F proteins are made by transfecting host cells with expression vectors that comprise a DNA sequence that encodes the respective OMP protein or P30F protein and then inducing expression of the protein in the host cells. For recombinant production, recombinant constructs comprising one or more of the sequences which encode the OMP protein or P30F protein are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The OMP proteins or P30F proteins may be expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the OMP protein or P30F protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate recombinant OMP protein or P30F protein Preparation of Antibodies The OMP proteins, P30F proteins, and variants thereof are used as immunogens to produce antibodies immunospecific for one or more OMP protein or one or more P30F protein. The term "immunospecific" means the antibodies have substantially greater affinity for one or more OMP protein or P30F protein than for other proteins. Such antibodies may include, but are not limited to, polyclonal, monoclonal, chimeric, single chain, and Fab fragments.

Polyclonal antibodies are generated using conventional techniques by administering the OMP protein or P30F protein, or a chimeric molecule to a host animal. Depending on the host species, various adjuvants may be used to increase immunological response. Among adjuvants used in humans, BCG (bacilli Calmette-Guerin, and Corynebacterium parvum are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols which involve competitive binding or immunoradiometric assays and typically involve the measurement of complex formation between the respective OMP protein or P30F protein and the antibody.

Polynucleotides that Encode OMP Proteins and P30F Proteins

Polynucleotides comprising sequences encoding an OMP protein or P30F protein may be synthesized in whole or in part using chemical methods. Polynucleotides which encode an OMP protein or P30F protein, particularly alleles of the genes which encode an OMP protein or P30F protein, may be obtained by screening a genomic library of an *E. chaffeensis* or *E. canis* isolate with a probe comprising sequences identical or complementary to the sequences shown in FIGS. 3–33 or with antibodies immunospecific for a OMP protein or P30F protein to identify clones containing such polynucleotide.

Polynucleotides which Encode OMP-1 Protein and P30 Protein

A. Isolation of the Outer Membrane Proteins

*E. chaffeensis* Arkansas strain and *E. canis* Oklahoma strain were cultivated in the DH82 dog macrophage cell line and purified by Percoll density gradient centrifugation. Purified ehrlichiae (100 μg) were suspended with 10 mM sodium phosphate buffer, pH 7.4, containing 0.1% Sodium N-lauroyl sarcosine (Sarkosyl) [Sigma, St. Louis, Mo.], 50 $\mu$g/ml each DNase I (Sigma) and RNase A (Sigma), and 2.5 mM $MgCl_2$. After incubation at 37° for 30 min, the sample was separated by centrifugation at 10,000×g for 1 h into the soluble supernatant and the insoluble precipitate. The insoluble pellet was resuspended 2 to 3 times with 0.1% Sarkosyl and centrifuged. The final pellet was analyzed by sodium dodecyl sulfate (SDS)-polyacrylamide gel electrophoresis (PAGE) and by electron microscopy.

Transmission electron microscopy revealed that the purified ehrlichial fraction consists of a mixture of electron dense and light forms of *E. chaffeensis* with slight disintegration of inner membrane. Ehrlichiae were not surrounded with the host inclusion membrane. Various sizes of membrane vesicles (<1 $\mu$m) without significant ribosomes or nuclear materials were observed in the Sarkosyl-insoluble fraction from the organism. Succinic debydrogenase (inner membrane marker enzyme of gram negative bacteria) activities were at less than the detection limit (1 n moles/min/mg of protein) in the Sarkosyl-insoluble fraction compared to approximately 10 n moles/min/mg of protein in the Percoll-purified organisms, suggesting that the insoluble fraction primarily consisted of the outer membrane of *E. chaffeensis.*

Analysis of the Sarkosyl-soluble, and insoluble fraction of *E. chaffeensis* by SDS-PAGE suggested that proteins of 30-kDa range in the insoluble fraction represent the major outer membrane proteins of this organism. Analysis of the Sarkosyl-soluble, and insoluble fraction of *E. canis* by SDS-PAGE suggested that proteins of 30-kDa range in the insoluble fraction represent the major outer membrane proteins of this organism also. *E. canis* was antigenically cross reactive with *E. chaffeensis*. These findings indicate that the 30-kDa range proteins represent the major outer membrane proteins of these two Ehrlichia spp.

To improve resolution of the outer membrane proteins, proteins in the Sarkosyl-insoluble pellet prepared from 400 $\mu$g of purified *E. chaffeensis* were separated by a reversed-discontinuous (Rd) SDS-PAGE (2.5-cm-long 17% gel on top of 11-cm-long 12% gel). At least five proteins of 30-kDa range in *E. chaffeensis* (P23, P25, P27, P28, and P29) were resolved from the Sarkosyl-insoluble proteins.

B. Cloning and Sequencing of the omp-1 Gene

The portion of the membrane containing bound proteins was excised and analyzed with an Applied Biosystems protein sequencer (Model 470). The N-terminal amino acid sequence of OMP-1 protein was determined as D P A G S G I N G N F Y I S G K Y M P, SEQ ID NO: 63. Based on 6th to 12th amino acids of this sequence, a forward primer, FECH1, having the sequence: 5'-CGGGATCCGAATTCGG (A/T/G/C)AT(A/T/C)AA(T/C)GG(A/T/G/C)AA(T/C)TT (T/C)TA-3'. SEQ ID NO: 64 was designed. Amino acids at the 1 to 5 positions of the N terminus of OMP-1 were not included in this primer design. For insertion into an expression vector, a 14-bp sequence (underlined) was added at the 5' end of primer to create an EcoRI and a BamHI site. The reverse primer, RECH2, which includes a NotI site at the 5' end for ligation into an expression vector had the sequence: 5'-AGCGGCCGCTTA(A/G)AA(T/C)A(C/G) (A/G)AA (C/T)CT T(C/G)C TCC-3'. SEQ ID NO: 65.

Genomic DNA of *E. chaffeensis* was isolated from purified organisms. PCR amplification with FECH1 and RECH2 primers was performed using a Perkin-Elmer Cetus DNA Thermal Cycler (model 480). A 0.8-kb amplified product was cloned in the pCRII vector of a TA closing kit, as described by the manufacturer (Invitrogen Co., San Diego, Calif.). The clone obtained was designated pCRIIp28. Both strands of the inserted DNA were sequenced by a dideoxy-termination method with an Applied Biosystems 373A DNA sequencer.

The 0.8-kb DNA fragment containing a partial OMP-1 gene, cloned in pCRIIp28, had an open reading frame (ORF) of 756 bp encoding a 251-amino acid recombinant protein (including both PCR primer regions) with a molecular mass of 27.2 kDa. The nucleotide sequence of the open reading frame, and the amino acid sequence of the polypeptide of the partial OMP-1 protein, are shown in FIG. 1.

A DNA fragment comprising the partial p30 gene was prepared in a similar manner, i.e., by PCR amplification of genomic DNA of *E. canis* using the forward primer, FECH1, which is described above, and a reverse primer, REC1, which is complimentary to the DNA sequence corresponding to amino acid positions 185 to 191 of the mature OMP-1 of *E. chaffeensis*. The sequence of REC1 is 5'-ACCTAACTTTCCTTGGTAAG-3', SEQ ID NO: 66.

Genomic DNA of *E. canis* was isolated from the purified organism. PCR amplification was performed by using a Perkin-Elmer Cetus DNA Thermal Cycler (model 480). The 0.6-kb products were amplified with the FECH1-REC1 primer pair and were cloned into the pCRII vector of a TA cloning kit (Invitrogen Co., San Diego, Calif.). The clone obtained by the primer pair was designated pCRIIp30. Both strands of the insert DNA were sequenced by a dideoxy termination method with an Applied Biosystems 373 DNA sequencer.

The 0.6-kb DNA fragment containing a partial p30 gene cloned had an open reading frame (ORF) of 579 bp encoding a 193-amino-acid protein with a molecular mass of 21,175 Da. The partial P30 protein of E. canis was encoded by nucleotide 97 through nucleotide 672 of the sequence shown in FIG. 19A and comprised amino acid 33 through amino acid 224 of the sequence shown in FIG. 19B.

Polynucleotides which Encode OMP 1A, OMP-1B, OMP-1C, OMP-1D, OMP-1F. and OMP1-E

A. Southern Blot Analysis.

Genomic DNA extracted from the purified E. chaffeensis (200 ng each) was digested with restriction endonucleases, electrophoresed, and transferred to Hybond-N+ nylon membrane (Amersham, Arlington Heights, Ill.), by a standard method. The 0.8-kb p28 gene fragment from the clone pCRIIp28 was labeled with [$\alpha$-$^{32}$P]dATP by the random primer method using a kit (Boehringer Mannheim, Indianapolis, Ind.) and the labeled fragment was used as a DNA probe. Hybridization was performed at 60° C. in rapid hybridization buffer (Amersham) for 20 h. The nylon sheet was washed in 0.1×SSC (1×SSC containing 0.15M sodium chloride and 0.015M sodium citrate) with 1% SDS at 55° C. and the hybridized probes were exposed to Hyperfilm (Amersham) at −80° C.

Genomic Southern blot analysis with several restriction enzymes resulted in one or more DNA fragment(s) of E. chaffeensis which hybridized to $^{32}$P-labeled omp-1 gene probe. The restriction enzymes used did not cut within the p28 gene portion of the pCRIIp28 insert. Xba I, BgI II, and Kpn I produced two bands, Spe I generated three bands, and EcoR V and Pst I produced multiple bands with different densities. EcoR I generated a broad band of 2.5 to 4 kb. These homologous genes are designated as omp-1 (outer membrane protein-1) family.

B. Cloning and sequencing of genomic copies of E. chaffeensis omp-1 gene.

The EcoR I and Pst I fragments of DNA, detected by genomic Southern blot analysis as described above, were inserted into pBluescript 11 KS (+) vectors, and the recombinant plasmids were introduced into E. coli DH5α. Using the colony hybridization method with the $^{32}$P-labeled omp-1gene probe, four positive clones were isolated from the transformnant. The positive clones were designated pEC2.6; pEC3.6, pPS2.6, and pPS3.6. These contained the ehrlichial DNA fragments of 2.6-kb (EcoR I), 3.6 kb (EcoR I), 2.6 kb (Pst I), and 3.6 kb (Pst I), respectively. The inserts of the clones pEC3.6 and pPS2.6 overlapped as shown in FIG. 2. The overlapping area was further confirmed by PCR of E. chaffeensis genomic DNA with two pairs of primer sets interposing the junctions of the four clones. The 1.1- to 1.6-kb DNA fragments of HindIII-HindIII, HindIII-EcoRI, or XhoI-EcoRI in the pEC2.6 and pEC3.6 were subcloned for sequencing. DNA sequencing was performed with suitable synthetic primers by dideoxy-termination method as described above.

Four DNA fragments from 2.6 to 3.6 kb were cloned from the EcoRI-digested and the PstI-digested genomic DNA of E. chaffeensis by colony hybridization with radiolabeled omp-1 gene probe. The inserted DNA of the two recombinant clones, pEC3.6 and pPS2.6, were overlapped. Sequencing revealed one 5'-truncated ORF of 243 bp (designated omp-1A) and five complete ORF of 836–861 bp (designated omp-1B to omp-1F), which are tandemly-arrayed and are homologous to the p28 gene (but are not identical), in the ehrlichial genomic DNA of 6,292 bp. The intergenic spaces were 581 bp between omp-1A and omp-1B and 260–308 bp among others. Putative promoter regions and ribosome-binding sites were identified in the noncoding regions.

C. Sequence Analysis and GenBank Accession Number.

Nucleotide sequences were analyzed with the DNASIS program (Hitachi Software Engineering Co., Ltd., Yokohama, Japan). A homology search was carried out with databases of the GenBank, Swiss Plot, PDB and PIR by using the software basic local alignment search tool in the BLAST network service (the National Center for Biotechnology Information, Bethesda, Md.). Phylogenetic analysis was performed by using the PHYLIP software package (version 3.5). An evolutional distance matrix, generated by using the Kimura formula in the PROTDIST, was used for construction of a phylogenetic tree by using the unweighted pair-group method analysis (UPGMA) (Felsenstein, J. 1989. PHYLIP-phylogeny inference package (version 3.3). Cladistics 5:164–166). The data were also examined using parsimony analysis (PROTPARS in PHYLIP). A bootstrap analysis was carried out to investigate the stability of randomly generated trees by using SEQBOOT and CONSENSE in the same package. The nucleotide sequence of the p28 gene and its gene copies has been assigned GenBank accession numbers U72291 and AF021338, respectively.

Proteins Encoded by the omp-1 Genes.

Five complete omp-1 gene copies (omp-1B to omp-1F) encode 279 to 287-amino acid proteins with molecular masses of 30,320–31,508 Da. The 25-amino acid sequence at the N-terminus of OMP-1B to OMP-1F (encoded in omp-1B to omp-1F) is predicted to be a signal peptide because three carboxyl-terminal amino acids of the signal peptides (Ser-X-Ala in OMP-1B, Leu-X-Ser for OMP-C, and Ser-X-Ser for OMP-1D and OMP-1F) are included in the preferred amino acid sequence of signal peptidase at the processing sites proposed by Oliver. The calculated molecular masses of the mature OMP-1B to OMP-1F from the predicted amino acid sequences are 28,181 Da for OMP-1B, 27,581 Da for OMP-1C, 28,747 Da for OMP-1D, 27,776 Da for OMP-1E, and 27,933 Da for OMP-1F. The estimated isoelectric points are 4.76–5.76 in the mature OMP-1B to OMP-1F. An amino acid sequence in omp-1F gene (the 80th to 94th amino acids) was identical to the N-terminal amino acid sequences of E. chaffeensis native P23 protein as determined chemically, which indicates that P23 is derived from the omp-1F gene.

Alignment of predicted amino acid sequences of the E. chaffeensis OMP-1 family and Cowdria ruminantium, revealed substitutions or deletions of one or several contiguous amino acid residues throughout the molecules. The significant differences in sequences among the aligned proteins are seen in the regions indicated SV (semivariable region) and HV (hypervariable region) 1 to 3 in FIG. 34. Computer analysis for hydropathy revealed that protein molecules predicted from all omp-1 gene copies contain alternative hydrophilic and hydrophobic motifs which are characteristic of transmembrane proteins. The HV1 and HV2 were found to locate in the hydrophilic regions.

The amino acid sequences of 5 mature proteins without signal peptides (OMP-1, and OMP-1C to OMP-1F) were similar to one another (71–83%) but the sequence of OMP-1B was dissimilar to those of the 5 proteins (45–48%). The amino acid sequences of the 5 proteins showed an intermediate degree of similarity with that of *C. ruminantium* MAP-1 (59–63%), but the similarity between that of the OMP-1B and the *C. ruminantium* MAP-1 was low (45%). These relations are shown in a phylogenetic tree which was obtained based on the amino acid sequence alignment by UPGMA method in the PHYLIP software package. Three proteins (OMP-1, OMP-1D, and OMP-1F) and two proteins (OMP-1C and OMP-1E) formed two separate clusters. The OMP-1B was located distantly from these two clusters. The *C. ruminantium* MAP-1 was positioned between the OMP-1B and other members in the OMP-1 family.

Preparation of a Recombinant Form of OMP-1 and P30

The 0.8-kb p28 gene from *E. chaffeensis* was excised from the clone pCRIIp28 by EcoRI-NotI double-digestion, ligated into EcoRI-NotI sites of a pET 29a expression vector, and amplified in *Escherichia coli* BL21 (DE3)pLysS (Novagen, Inc., Madison, Wis.). The clone (designated pET29p28) produced a fusion protein with a 35-amino acid sequence carried from the vector at the N terminus. The amino acid sequence of the OMP-1 portion of the fusion protein, referred to hereinafter as rOMP-1, is depicted in FIG. 1.

An expression vector comprising the p30 gene was used to prepare the recombinant form of P30. To prepare the expression vector, an 0.6-kb fragment was excised from the clone pCRIIp30 by EcoRI digestion, ligated into EcoRI site of a pET29a expression vector, and amplifed in *E. coli* BL21(DE3)pLys (Novagen, Inc., Madison, Wis.). The clone (designated pET29p30) produced a fusion protein with a 35-amino-acid sequence and a 21-amino-acid sequence carried from the vector at the N and C termini, respectively. The fusion protein had an amino acid sequence consisting of 249-amino acid residues with a molecular mass of 27,316 Da. The amino acid sequence of the P30 portion of the fusion protein, referred to hereinafter as rP30, is amino acid 33 through amino acid 224 of the sequence shown in FIG. 19B.

Preparation of Anti-rOMP1 Antibody

An rOMP-1antigen was prepared by excising the gel band corresponding to the rOMP-1 protein in SDS-PAGE, mincing the band in phosphate-buffered saline (PBS), pH 7.4, and mixing with an equal volume of Freund's incomplete adjuvant (Sigma). The rOMP-i mixture (1 mg of protein each time) was subcutaneously injected into a rabbit every 2 weeks four times. A serum sample was collected from the rabbit to provide the anti-rOMP-1 antibody The anti-rOMP-1 antibody was examined by western immunoblot analysis. The results indicated that the rabbit anti-rOMP-1 antibody recognized not only rOMP-1 (31 kDa) and OMP-1 protein, but also P29 and P25 of *E. chaffeensis* and P30 of *E. canis*. These results indicate that OMP-1 shares antigenic epitopes with P25 and P29 in *E. chaffeensis* and P30 of *E. canis*.

The following examples are for purposes of illustration only and are not intended to limit the scope of the claims which are appended hereto.

EXAMPLE 1

Assaying for the Presence of Anti-OMP-1 Antibody in a Patient

Convalescent-phase serum from a patient with clinical signs of human ehrlichiosis was used. Western blot analyses using the rP28 protein as antigen was performed with 1:1,000 dilutions of this serum. Alkaline phosphatase-conjugated affinity-purified anti-human immunoglobulin G (Kirkegaard & Perry Laboratories, Inc., Gaithersburg, Md.) was used at a 1:1,000 or 1:2,000 dilution as secondary antibodies. Results indicated that serum from a patient with clinical signs of human ehrlichiosis reacted strongly to rOMP-1 protein (31 kDa).

EXAMPLE 2

Assaying for the Presence of Anti-OMP-1 Antibody in a Patient

Convalescent-phase serum from a patient with clinical signs of human ehrlichiosis was reacted with the rP30 protein of *E. canis* as described in Example 1. The serum reacted strongly to rP30. These results indicate the rP30 is useful for diagnosing an infection with *E. chaffeensis* in human patients.

EXAMPLE 3

Identifying *E. chaffeensis*-Infected Cells using Anti-rOMP-1 Antibody

*E. chaffeensis*-infected DH82 cells were sonicated and centrifuged at 400×g for 10 min. The supernatant was then centrifuged at 10,000×g for 10 min to obtain ehrlichia-enriched pellet. The pellet was resuspended and incubated with rabbit anti-rOMP-1 antibody or normal rabbit serum (1:100 dilution) at 37° C. for 1 h in PBS containing 1% bovine serum albumin (BSA-PBS). After washing, the ehrlichiae was incubated with gold-conjugated protein G (20 nm), Sigma) at 1:30 dilution for 1 h at room temperature in BSA-PBS. After washing again, the specimen was fixed with 1.25% formaldehyde, 2.5% glutaraldehyde, and 0.03% trinitrophenol in 0.1 M cacodylate buffer (pH 7.4) for 24 h and postfixed in 1% osmium-1.5% potassium ferricyanide for 1 h (34). The section was then embedded in PolyBed 812 (Polysciences, Warraington, Pa). The specimen was ultrathin sectioned at 60 nm, stained with uranyl acetate and lead citrate, and observed with a Philips 300 transmission electron microscope at 60 kV.

Transmission immunoelectron microscopy with colloidal gold-conjugated protein G and rabbit anti-rP28 antibody revealed gold particles bound to *E. chaffeensis* surface. The distribution of the particles was random, close to the surface, and appeared as if almost embedded in the membrane, suggesting that the antigenic epitope protrudes very little from the lipid bilayer. Nonetheless, the antigenic epitope was surface-exposed, and thus, could be recognized by rabbit anti-rOMP-1 antibody. No gold particles were observed on host cytoplasmic membrane or *E. chaffeensis* incubated with normal rabbit serum.

EXAMPLE 4

Immunization of Mice and *E. chaffeensis* Challenge

The rOMP-1band in SDS- PAGE was excised, minced, and mixed with an equal volume of Freund's incomplete or complete adjuvant. Nine BALB/c male mice (6 weeks old) were divided into two groups. Five mice were intraperitoneally immunized a total of four times at 10-day intervals; twice with a mixture of the minced gel with the rOMP-1 (30 to 40 µg of protein per mouse each time) and incomplete adjuvant, and twice with a mixture of the recombinant protein (the same amount as before) and complete adjuvant. Four mice were intraperitoneally injected with a mixture of the minced gel without protein and the respective adjuvants. For ehrlichia-challenge, approximately $1 \times 10^7$ DH82 cells heavily-infected with *E. chaffeensis* were disrupted by sonication in serum-free DMEM (GIBCO-BRL) and centrifuged at 200×g for 5 min. The supernatant was diluted to a final volume of 5 ml, and 0.3 ml was inoculated intraperitoneally into each mouse 10 days after the last immunization. Before challenge, all 5-immunized mice had a titer of 1:160 against E. chaffeensis antigen by IFA and all 4-nonimmunized mice were negative.

At day 5 post-challenge, approximately 1 ml of blood was collected in an EDTA tube from each mouse and protection was assessed by PCR detection of E. chaffeensis 16S rDNA in the buffy coat of the collected blood. E. chaffeensis could not be reisolated in cell culture at day 10 postinfection. Day 5 post challenge is the optimum time at which establishment of ehrlichial infection can be examined by PCR without the influence of residual DNA from the ehrlichiae used as the challenge before the spontaneous clearance of organisms take place. The E. chaffeensis-specific DNA fragment was observed in all nonirnmunized mice but not in any immunized mice, indicating that immunization of rOMP-1 apparently protects mice from ehrlichial infection and indicating that the OMP-1 is a potential protective antigen.

EXAMPLE 5

Assaying for the Presence of Anti-P30 Antibody in Dogs

The rP30 protein was used as an antigen in a Western immunoblot analysis and dot blot analysis to detect the presence of antibody to E. canis in serum from E. canis infected dogs. The results of the Western immunoblot analysis indicated that reactivity of the sera with rP30 was stronger than the reactivity that was observed when purified E. canis was used as antigen. The results of the dot blot assay indicated that rP30 is a useful and sensitive tool for serodiagnosis of canine ehrlichiosis.

What is claimed is:

1. A method for diagnosing an infection with *E. canis* in a Canidae patient comprising the steps of:
   (a) providing a serum sample from the patient;
   (b) providing an isolated or purified P30-10 protein of *E. canis*;
   (c) contacting the serum sample with the P30-10 protein; and
   (d) assaying for the formation of a complex between antibodies in the serum sample and the P30-10 protein, wherein formation of said complex is indicative of infection with *E. canis*.

2. The method of claim 1 wherein the *E. canis* P30-10 protein comprises amino acid 26 through amino acid 280 of the sequence set forth in SEQ ID NO. 48.

* * * * *

SEQUENCE LISTING

<160> NUMBER OF SEQ ID NOS: 66

<210> SEQ ID NO 1
<211> LENGTH: 846
<212> TYPE: DNA
<213> ORGANISM: Ehrlichia chaffeensis
<220> FEATURE:
<221> NAME/KEY: CDS
<222> LOCATION: (1)..(846)

<400> SEQUENCE: 1

```
atg aat tac aaa aaa gtt ttc ata aca agt gca ttg ata tca tta ata      48
Met Asn Tyr Lys Lys Val Phe Ile Thr Ser Ala Leu Ile Ser Leu Ile
 1               5                  10                  15 tct tct cta cct gga gta tca ttt tcc gac cca gca ggt agt ggt att      96
Ser Ser Leu Pro Gly Val Ser Phe Ser Asp Pro Ala Gly Ser Gly Ile
             20                  25                  30 aac ggt aat ttc tac atc agt gga aaa tac atg cca agt gct tcg cat     144
Asn Gly Asn Phe Tyr Ile Ser Gly Lys Tyr Met Pro Ser Ala Ser His
         35                  40                  45 ttt gga gta ttc tct gct aag gaa gaa aga aat aca aca gtt gga gtg     192
Phe Gly Val Phe Ser Ala Lys Glu Glu Arg Asn Thr Thr Val Gly Val
     50                  55                  60 ttt gga ctg aag caa aat tgg gac gga agc gca ata tcc aac tcc tcc     240
Phe Gly Leu Lys Gln Asn Trp Asp Gly Ser Ala Ile Ser Asn Ser Ser
 65                  70                  75                  80 cca aac gat gta ttc act gtc tca aat tat tca ttt aaa tat gaa aac     288
Pro Asn Asp Val Phe Thr Val Ser Asn Tyr Ser Phe Lys Tyr Glu Asn
                 85                  90                  95 aac ccg ttt tta ggt ttt gca gga gct att ggt tac tca atg gat ggt     336
Asn Pro Phe Leu Gly Phe Ala Gly Ala Ile Gly Tyr Ser Met Asp Gly
            100                 105                 110 cca aga ata gag ctt gaa gta tct tat gaa aca ttt gat gta aaa aat     384
Pro Arg Ile Glu Leu Glu Val Ser Tyr Glu Thr Phe Asp Val Lys Asn
        115                 120                 125 caa ggt aac aat tat aag aat gaa gca cat aga tat tgt gct cta tcc     432
Gln Gly Asn Asn Tyr Lys Asn Glu Ala His Arg Tyr Cys Ala Leu Ser
    130                 135                 140 cat aac tca gca gca gac atg agt agt gca agt aat aat ttt gtc ttt     480
His Asn Ser Ala Ala Asp Met Ser Ser Ala Ser Asn Asn Phe Val Phe
145                 150                 155                 160
```

```
cta aaa aat gaa gga tta ctt gac ata tca ttt atg ctg aac gca tgc    528
Leu Lys Asn Glu Gly Leu Leu Asp Ile Ser Phe Met Leu Asn Ala Cys
            165                 170                 175 tat gac gta gta ggc gaa ggc ata cct ttt tct cct tat ata tgc gca    576
Tyr Asp Val Val Gly Glu Gly Ile Pro Phe Ser Pro Tyr Ile Cys Ala
        180                 185                 190 ggt atc ggt act gat tta gta tcc atg ttt gaa gct aca aat cct aaa    624
Gly Ile Gly Thr Asp Leu Val Ser Met Phe Glu Ala Thr Asn Pro Lys
    195                 200                 205 att tct tac caa gga aag tta ggt tta agc tac tct ata agc cca gaa    672
Ile Ser Tyr Gln Gly Lys Leu Gly Leu Ser Tyr Ser Ile Ser Pro Glu
210                 215                 220 gct tct gtg ttt att ggt ggg cac ttt cat aag gta tta ggg aac gaa    720
Ala Ser Val Phe Ile Gly Gly His Phe His Lys Val Leu Gly Asn Glu
225                 230                 235                 240 ttt aga gat att cct act ata ata cct act gga tca aca ctt gca gga    768
Phe Arg Asp Ile Pro Thr Ile Ile Pro Thr Gly Ser Thr Leu Ala Gly
                245                 250                 255 aaa gga aac tac cct gca ata gta ata ctg gat gta tgc cac ttt gga    816
Lys Gly Asn Tyr Pro Ala Ile Val Ile Leu Asp Val Cys His Phe Gly
            260                 265                 270 ata gaa ctt gga gga agg ttt gct ttc taa                            846
Ile Glu Leu Gly Gly Arg Phe Ala Phe
        275                 280

<210> SEQ ID NO 2
<211> LENGTH: 281
<212> TYPE: PRT
<213> ORGANISM: Ehrlichia chaffeensis

<400

```
Ile Ser Tyr Gln Gly Lys Leu Gly Leu Ser Tyr Ser Ile Ser Pro Glu
        210                 215                 220

Ala Ser Val Phe Ile Gly Gly His Phe His Lys Val Leu Gly Asn Glu
225                 230                 235                 240

Phe Arg Asp Ile Pro Thr Ile Ile Pro Thr Gly Ser Thr Leu Ala Gly
                245                 250                 255

Lys Gly Asn Tyr Pro Ala Ile Val Ile Leu Asp Val Cys His Phe Gly
                260                 265                 270

Ile Glu Leu Gly Gly Arg Phe Ala Phe
        275                 280
```

<210> SEQ ID NO 3
<211> LENGTH: 852
<212> TYPE: DNA
<213> ORGANISM: Ehrlichia chaffeensis
<220> FEATURE:
<221> NAME/KEY: CDS
<222> LOCATION: (1)..(852)

<400> SEQUENCE: 3

```
atg aat tac aag aaa att ttt gta agc agt gca tta att tca tta atg      48
Met Asn Tyr Lys Lys Ile Phe Val Ser Ser Ala Leu Ile Ser Leu Met
  1               5                  10                  15 tca atc tta cct tac caa tct ttt gca gat cct gta act tca aat gat      96
Ser Ile Leu Pro Tyr Gln Ser Phe Ala Asp Pro Val Thr Ser Asn Asp
             20                  25                  30 aca gga atc aac gac agc aga gaa ggc ttc tac att agt gta aag tat     144
Thr Gly Ile Asn Asp Ser Arg Glu Gly Phe Tyr Ile Ser Val Lys Tyr
         35                  40                  45 aat cca agc ata tca cac ttc aga aaa ttc tca gct gaa gaa gct ccc     192
Asn Pro Ser Ile Ser His Phe Arg Lys Phe Ser Ala Glu Glu Ala Pro
     50                  55                  60 atc aat gga aat act tct atc act aaa aag gtt ttc ggg ctg aaa aaa     240
Ile Asn Gly Asn Thr Ser Ile Thr Lys Lys Val Phe Gly Leu Lys Lys
 65                  70                  75                  80 gac gga gat ata gca caa tct gcg aat ttt aac agg aca gat cca gcc     288
Asp Gly Asp Ile Ala Gln Ser Ala Asn Phe Asn Arg Thr Asp Pro Ala
                 85                  90                  95 ctc gag ttt cag aat aac cta ata tca gga ttc tca gga agt att ggt     336
Leu Glu Phe Gln Asn Asn Leu Ile Ser Gly Phe Ser Gly Ser Ile Gly
            100                 105                 110 tat gct atg gat ggg cca aga ata gaa ctt gaa gct gca tac caa aaa     384
Tyr Ala Met Asp Gly Pro Arg Ile Glu Leu Glu Ala Ala Tyr Gln Lys
        115                 120                 125 ttt gat gca aaa aat cct gac aac aat gac act aat agc ggt gac tac     432
Phe Asp Ala Lys Asn Pro Asp Asn Asn Asp Thr Asn Ser Gly Asp Tyr
    130                 135                 140 tat aaa tac ttt gga cta tct cgt gaa gac gca ata gca gat aag aaa     480
Tyr Lys Tyr Phe Gly Leu Ser Arg Glu Asp Ala Ile Ala Asp Lys Lys
145                 150                 155                 160 tat gtt gtc ctt aaa aat gaa ggc atc act ttt atg tca tta atg gtt     528
Tyr Val Val Leu Lys Asn Glu Gly Ile Thr Phe Met Ser Leu Met Val
                165                 170                 175 aac act tgc tat gac att aca gct gaa gga gta cct ttc ata ccg tat     576
Asn Thr Cys Tyr Asp Ile Thr Ala Glu Gly Val Pro Phe Ile Pro Tyr
            180                 185                 190 gca tgt gca ggt gta gga gca gac ctt ata aac gta ttt aag gat ttt     624
Ala Cys Ala Gly Val Gly Ala Asp Leu Ile Asn Val Phe Lys Asp Phe
        195                 200                 205 aat tta aaa ttc tca tac caa ggg aaa ata ggt att agc tat cca atc     672
```

```
Asn Leu Lys Phe Ser Tyr Gln Gly Lys Ile Gly Ile Ser Tyr Pro Ile
    210                 215                 220 aca cca gaa gtt tcc gct ttt att gga gga tac tac cac gga gtt ata      720
Thr Pro Glu Val Ser Ala Phe Ile Gly Gly Tyr Tyr His Gly Val Ile
225                 230                 235                 240 gga aat aat ttt aac aaa ata cct gta ata aca cct gta gta tta gaa      768
Gly Asn Asn Phe Asn Lys Ile Pro Val Ile Thr Pro Val Val Leu Glu
                245                 250                 255 gga gct cct caa aca aca tct gcg cta gta act att gac act gga tac      816
Gly Ala Pro Gln Thr Thr Ser Ala Leu Val Thr Ile Asp Thr Gly Tyr
            260                 265                 270 ttt ggc gga gaa gtt gga gta agg ttc acc ttc tag                      852
Phe Gly Gly Glu Val Gly Val Arg Phe Thr Phe
        275                 280

<210> SEQ ID NO 4
<211> LENGTH: 283
<212> TYPE: PRT
<213> ORGANISM: Ehrlichia chaffeensis

<400> SEQUENCE: 4

Met Asn Tyr Lys Lys Ile Phe Val Ser Ser Ala Leu Ile Ser Leu Met
  1               5                  10                  15

Ser Ile Leu Pro Tyr Gln Ser Phe Ala Asp Pro Val Thr Ser Asn Asp
             20                  25                  30

Thr Gly Ile Asn Asp Ser Arg Glu Gly Phe Tyr Ile Ser Val Lys Tyr
         35                  40                  45

Asn Pro Ser Ile Ser His Phe Arg Lys Phe Ser Ala Glu Glu Ala Pro
     50                  55                  60

Ile Asn Gly Asn Thr Ser Ile Thr Lys Lys Val Phe Gly Leu Lys Lys
 65                  70                  75                  80

Asp Gly Asp Ile Ala Gln Ser Ala Asn Phe Asn Arg Thr Asp Pro Ala
                 85                  90                  95

Leu Glu Phe Gln Asn Asn Leu Ile Ser Gly Phe Ser Gly Ser Ile Gly
            100                 105                 110

Tyr Ala Met Asp Gly Pro Arg Ile Glu Leu Glu Ala Ala Tyr Gln Lys
        115                 120                 125

Phe Asp Ala Lys Asn Pro Asp Asn Asn Asp Thr Asn Ser Gly Asp Tyr
    130                 135                 140

Tyr Lys Tyr Phe Gly Leu Ser Arg Glu Asp Ala Ile Ala Asp Lys Lys
145                 150                 155                 160

Tyr Val Val Leu Lys Asn Glu Gly Ile Thr Phe Met Ser Leu Met Val
                165                 170                 175

Asn Thr Cys Tyr Asp Ile Thr Ala Glu Gly Val Pro Phe Ile Pro Tyr
            180                 185                 190

Ala Cys Ala Gly Val Gly Ala Asp Leu Ile Asn Val Phe Lys Asp Phe
        195                 200                 205

Asn Leu Lys Phe Ser Tyr Gln Gly Lys Ile Gly Ile Ser Tyr Pro Ile
    210                 215                 220

Thr Pro Glu Val Ser Ala Phe Ile Gly Gly Tyr Tyr His Gly Val Ile
225                 230                 235                 240

Gly Asn Asn Phe Asn Lys Ile Pro Val Ile Thr Pro Val Val Leu Glu
                245                 250                 255

Gly Ala Pro Gln Thr Thr Ser Ala Leu Val Thr Ile Asp Thr Gly Tyr
            260                 265                 270

Phe Gly Gly Glu Val Gly Val Arg Phe Thr Phe
```

<210> SEQ ID NO 5
<211> LENGTH: 843
<212> TYPE: DNA
<213> ORGANISM: Ehrlichia chaffeensis
<220

```
                        260              265              270
gaa ctt gga gga aga ttt aac ttc taa                                      843
Glu Leu Gly Gly Arg Phe Asn Phe
                275              280

<210> SEQ ID NO 6
<211> LENGTH: 280
<212> TYPE: PRT
<213> ORGANISM: Ehrlichia chaffeensis

<400> SEQUENCE: 6

Met Asn Cys Lys Lys Phe Phe Ile Thr Thr Ala Leu Ala Leu Pro Met
  1               5                  10                  15

Ser Phe Leu Pro Gly Ile Leu Leu Ser Glu Pro Val Gln Asp Asp Ser
             20                  25                  30

Val Ser Gly Asn Phe Tyr Ile Ser Gly Lys Tyr Met Pro Ser Ala Ser
         35                  40                  45

His Phe Gly Val Phe Ser Lys Glu Glu Lys Asn Pro Thr Val Ala
     50                  55                  60

Leu Tyr Gly Leu Lys Gln Asp Trp Asn Gly Val Ser Ala Ser His
 65                  70                  75                  80

Ala Asp Ala Asp Phe Asn Asn Lys Gly Tyr Ser Phe Lys Tyr Glu Asn
                 85                  90                  95

Asn Pro Phe Leu Gly Phe Ala Gly Ala Ile Gly Tyr Ser Met Gly Gly
            100                 105                 110

Pro Arg Ile Glu Phe Glu Val Ser Tyr Glu Thr Phe Asp Val Lys Asn
        115                 120                 125

Gln Gly Gly Asn Tyr Lys Asn Asp Ala His Arg Tyr Cys Ala Leu Asp
    130                 135                 140

Arg Lys Ala Ser Ser Thr Asn Ala Thr Ala Ser His Tyr Val Leu Leu
145                 150                 155                 160

Lys Asn Glu Gly Leu Leu Asp Ile Ser Leu Met Leu Asn Ala Cys Tyr
                165                 170                 175

Asp Val Val Ser Glu Gly Ile Pro Phe Ser Pro Tyr Ile Cys Ala Gly
            180                 185                 190

Val Gly Thr Asp Leu Ile Ser Met Phe Glu Ala Ile Asn Pro Lys Ile
        195                 200                 205

Ser Tyr Gln Gly Lys Leu Gly Leu Ser Tyr Ser Ile Asn Pro Glu Ala
    210                 215                 220

Ser Val Phe Val Gly Gly His Phe His Lys Val Ala Gly Asn Glu Phe
225                 230                 235                 240

Arg Asp Ile Ser Thr Leu Lys Ala Phe Ala Thr Pro Ser Ser Ala Ala
                245                 250                 255

Thr Pro Asp Leu Ala Thr Val Thr Leu Ser Val Cys His Phe Gly Val
            260                 265                 270

Glu Leu Gly Gly Arg Phe Asn Phe
        275                 280

<210> SEQ ID NO 7
<211> LENGTH: 861
<212> TYPE: DNA
<213> ORGANISM: Ehrlichia chaffeensis
<220> FEATURE:
<221> NAME/KEY: CDS
<222> LOCATION: (1)..(861)

<400> SEQUENCE: 7
```

-continued

| | | |
|---|---|---|
| atg aac tgc gaa aaa ttt ttt ata aca act gca tta aca tta cta atg<br>Met Asn Cys Glu Lys Phe Phe Ile Thr Thr Ala Leu Thr Leu Leu Met<br>1               5                  10                  15 | | 48 |
| tcc ttc tta cct gga ata tca ctt tct gat cca gta cag gat gac aac<br>Ser Phe Leu Pro Gly Ile Ser Leu Ser Asp Pro Val Gln Asp Asp Asn<br>            20                  25                  30 | | 96 |
| att agt ggt aat ttc tac atc agt gga aag tat atg cca agc gct tcg<br>Ile Ser Gly Asn Phe Tyr Ile Ser Gly Lys Tyr Met Pro Ser Ala Ser<br>        35                  40                  45 | | 144 |
| cat ttt gga gtt ttt tct gcc aag gaa gaa aga aat aca aca gtt gga<br>His Phe Gly Val Phe Ser Ala Lys Glu Glu Arg Asn Thr Thr Val Gly<br>    50                  55                  60 | | 192 |
| gta ttt gga ata gag caa gat tgg gat aga tgt gta ata tct aga acc<br>Val Phe Gly Ile Glu Gln Asp Trp Asp Arg Cys Val Ile Ser Arg Thr<br>65                  70                  75                  80 | | 240 |
| act tta agc gat ata ttc acc gtt cca aat tat tca ttt aag tat gaa<br>Thr Leu Ser Asp Ile Phe Thr Val Pro Asn Tyr Ser Phe Lys Tyr Glu<br>                85                  90                  95 | | 288 |
| aat aat cta ttt tca gga ttt gca gga gct att ggc tac tca atg gat<br>Asn Asn Leu Phe Ser Gly Phe Ala Gly Ala Ile Gly Tyr Ser Met Asp<br>            100                 105                 110 | | 336 |
| ggc cca aga ata gag ctt gaa gta tct tat gaa gca ttc gat gtt aaa<br>Gly Pro Arg Ile Glu Leu Glu Val Ser Tyr Glu Ala Phe Asp Val Lys<br>        115                 120                 125 | | 384 |
| aat caa ggt aac aat tat aag aac gaa gca cat aga tat tat gct ctg<br>Asn Gln Gly Asn Asn Tyr Lys Asn Glu Ala His Arg Tyr Tyr Ala Leu<br>    130                 135                 140 | | 432 |
| tcc cat ctt ctc ggc aca gag aca cag ata gat ggt gca ggc agt gcg<br>Ser His Leu Leu Gly Thr Glu Thr Gln Ile Asp Gly Ala Gly Ser Ala<br>145                 150                 155                 160 | | 480 |
| tct gtc ttt cta ata aat gaa gga cta ctt gat aaa tca ttt atg ctg<br>Ser Val Phe Leu Ile Asn Glu Gly Leu Leu Asp Lys Ser Phe Met Leu<br>                165                 170                 175 | | 528 |
| aac gca tgt tat gat gta ata agt gaa ggc ata cct ttt tct cct tat<br>Asn Ala Cys Tyr Asp Val Ile Ser Glu Gly Ile Pro Phe Ser Pro Tyr<br>            180                 185                 190 | | 576 |
| ata tgt gca ggt att ggt att gat tta gta tcc atg ttt gaa gct ata<br>Ile Cys Ala Gly Ile Gly Ile Asp Leu Val Ser Met Phe Glu Ala Ile<br>        195                 200                 205 | | 624 |
| aat cct aaa att tct tat caa gga aaa tta ggc tta agt tac cct ata<br>Asn Pro Lys Ile Ser Tyr Gln Gly Lys Leu Gly Leu Ser Tyr Pro Ile<br>    210                 215                 220 | | 672 |
| agc cca gaa gct tct gtg ttt att ggt gga cat ttt cat aag gtg ata<br>Ser Pro Glu Ala Ser Val Phe Ile Gly Gly His Phe His Lys Val Ile<br>225                 230                 235                 240 | | 720 |
| gga aac gaa ttt aga gat att cct act atg ata cct agt gaa tca gcg<br>Gly Asn Glu Phe Arg Asp Ile Pro Thr Met Ile Pro Ser Glu Ser Ala<br>                245                 250                 255 | | 768 |
| ctt gca gga aaa gga aac tac cct gca ata gta aca ctg gac gtg ttc<br>Leu Ala Gly Lys Gly Asn Tyr Pro Ala Ile Val Thr Leu Asp Val Phe<br>            260                 265                 270 | | 816 |
| tac ttt ggc ata gaa ctt gga gga agg ttt aac ttc caa ctt tga<br>Tyr Phe Gly Ile Glu Leu Gly Gly Arg Phe Asn Phe Gln Leu<br>        275                 280                 285 | | 861 |

<210> SEQ ID NO 8
<211> LENGTH: 286
<212> TYPE: PRT
<213> ORGANISM: Ehrlichia chaffeensis

<400> SEQUENCE: 8

-continued

```
Met Asn Cys Glu Lys Phe Phe Ile Thr Thr Ala Leu Thr Leu Leu Met
  1               5                  10                  15

Ser Phe Leu Pro Gly Ile Ser Leu Ser Asp Pro Val Gln Asp Asp Asn
             20                  25                  30

Ile Ser Gly Asn Phe Tyr Ile Ser Gly Lys Tyr Met Pro Ser Ala Ser
             35                  40                  45

His Phe Gly Val Phe Ser Ala Lys Glu Glu Arg Asn Thr Thr Val Gly
         50                  55                  60

Val Phe Gly Ile Glu Gln Asp Trp Asp Arg Cys Val Ile Ser Arg Thr
 65                  70                  75                  80

Thr Leu Ser Asp Ile Phe Thr Val Pro Asn Tyr Ser Phe Lys Tyr Glu
                 85                  90                  95

Asn Asn Leu Phe Ser Gly Phe Ala Ala Ile Gly Tyr Ser Met Asp
            100                 105                 110

Gly Pro Arg Ile Glu Leu Glu Val Ser Tyr Glu Ala Phe Asp Val Lys
            115                 120                 125

Asn Gln Gly Asn Asn Tyr Lys Asn Glu Ala His Arg Tyr Tyr Ala Leu
    130                 135                 140

Ser His Leu Leu Gly Thr Glu Thr Gln Ile Asp Gly Ala Gly Ser Ala
145                 150                 155                 160

Ser Val Phe Leu Ile Asn Glu Gly Leu Leu Asp Lys Ser Phe Met Leu
                165                 170                 175

Asn Ala Cys Tyr Asp Val Ile Ser Glu Gly Ile Pro Phe Ser Pro Tyr
            180                 185                 190

Ile Cys Ala Gly Ile Gly Ile Asp Leu Val Ser Met Phe Glu Ala Ile
        195                 200                 205

Asn Pro Lys Ile Ser Tyr Gln Gly Lys Leu Gly Leu Ser Tyr Pro Ile
    210                 215                 220

Ser Pro Glu Ala Ser Val Phe Ile Gly His Phe His Lys Val Ile
225                 230                 235                 240

Gly Asn Glu Phe Arg Asp Ile Pro Thr Met Ile Pro Ser Glu Ser Ala
                245                 250                 255

Leu Ala Gly Lys Gly Asn Tyr Pro Ala Ile Val Thr Leu Asp Val Phe
            260                 265                 270

Tyr Phe Gly Ile Glu Leu Gly Gly Arg Phe Asn Phe Gln Leu
        275                 280                 285
```

<210> SEQ ID NO 9
<211> LENGTH: 837
<212> TYPE: DNA
<213> ORGANISM: Ehrlichia chaffeensis
<220> FEATURE -continued

| | | |
|---|---|---|
| His Phe Gly Met Phe Ser Ala Lys Glu Glu Lys Asn Pro Thr Val Ala<br>    50                  55                  60 | | |
| ttg tat ggc tta aaa caa gat tgg gaa ggg att agc tca tca agt cac<br>Leu Tyr Gly Leu Lys Gln Asp Trp Glu Gly Ile Ser Ser Ser Ser His<br> 65                  70                  75                  80 | 240 | |
| aat gat aat cat ttc aat aac aag ggt tat tca ttt aaa tat gaa aat<br>Asn Asp Asn His Phe Asn Asn Lys Gly Tyr Ser Phe Lys Tyr Glu Asn<br>                 85                  90                  95 | 288 | |
| aac cca ttt tta ggg ttt gca gga gct att ggt tat tca atg ggt ggt<br>Asn Pro Phe Leu Gly Phe Ala Gly Ala Ile Gly Tyr Ser Met Gly Gly<br>            100                 105                 110 | 336 | |
| cca aga gta gag ttt gaa gtg tcc tat gaa aca ttt gac gtt aaa aat<br>Pro Arg Val Glu Phe Glu Val Ser Tyr Glu Thr Phe Asp Val Lys Asn<br>        115                 120                 125 | 384 | |
| cag ggt aat aac tat aaa aat gat gct cac aga tac tgt gct tta ggt<br>Gln Gly Asn Asn Tyr Lys Asn Asp Ala His Arg Tyr Cys Ala Leu Gly<br>    130                 135                 140 | 432 | |
| caa caa gac aac agc gga ata cct aaa act agt aaa tac gta ctg tta<br>Gln Gln Asp Asn Ser Gly Ile Pro Lys Thr Ser Lys Tyr Val Leu Leu<br>145                 150                 155                 160 | 480 | |
| aaa agc gaa gga ttg ctt gac ata tca ttt atg cta aat gca tgc tat<br>Lys Ser Glu Gly Leu Leu Asp Ile Ser Phe Met Leu Asn Ala Cys Tyr<br>                165                 170                 175 | 528 | |
| gat ata ata aac gag agc ata cct ttg tct cct tac ata tgt gca ggt<br>Asp Ile Ile Asn Glu Ser Ile Pro Leu Ser Pro Tyr Ile Cys Ala Gly<br>            180                 185                 190 | 576 | |
| gtt ggt act gat tta ata tcc atg ttt gaa gct aca aat cct aaa att<br>Val Gly Thr Asp Leu Ile Ser Met Phe Glu Ala Thr Asn Pro Lys Ile<br>        195                 200                 205 | 624 | |
| tct tac caa ggg aag tta ggt cta agt tac tct ata aac cca gaa gct<br>Ser Tyr Gln Gly Lys Leu Gly Leu Ser Tyr Ser Ile Asn Pro Glu Ala<br>    210                 215                 220 | 672 | |
| tct gta ttt att ggt gga cat ttt cat aag gtg ata gga aac gaa ttt<br>Ser Val Phe Ile Gly Gly His Phe His Lys Val Ile Gly Asn Glu Phe<br>225                 230                 235                 240 | 720 | |
| agg gac att cct act ctg aaa gca ttt gtt acg tca tca gct act cca<br>Arg Asp Ile Pro Thr Leu Lys Ala Phe Val Thr Ser Ser Ala Thr Pro<br>                245                 250                 255 | 768 | |
| gat cta gca ata gta aca cta agt gta tgt cat ttt gga ata gaa ctt<br>Asp Leu Ala Ile Val Thr Leu Ser Val Cys His Phe Gly Ile Glu Leu<br>            260                 265                 270 | 816 | |
| gga gga agg ttt aac ttc taa<br>Gly Gly Arg Phe Asn Phe<br>        275 | 837 | |

<210> SEQ ID NO 10
<211> LENGTH: 278
<212> TYPE: PRT
<213> ORGANISM: Ehrlichia chaffeensis

<400> SEQUENCE: 10

Met Asn Cys Lys Lys Phe Phe Ile Thr Thr Ala Leu Val Ser Leu Met
 1               5                  10                  15

Ser Phe Leu Pro Gly Ile Ser Phe Ser Asp Pro Val Gln Gly Asp Asn
            20                  25                  30

Ile Ser Gly Asn Phe Tyr Val Ser Gly Lys Tyr Met Pro Ser Ala Ser
        35                  40                  45

His Phe Gly Met Phe Ser Ala Lys Glu Glu Lys Asn Pro Thr Val Ala
    50                  55                  60

-continued

| | | | | | | | | | | | | | | | |
|---|---|---|---|---|---|---|---|---|---|---|---|---|---|---|---|
| Leu | Tyr | Gly | Leu | Lys | Gln | Asp | Trp | Glu | Gly | Ile | Ser | Ser | Ser | Ser | His |
| 65 | | | | 70 | | | | 75 | | | | | | | 80 |

Asn Asp Asn His Phe Asn Asn Lys Gly Tyr Ser Phe Lys Tyr Glu Asn
                  85                    90                    95

Asn Pro Phe Leu Gly Phe Ala Gly Ala Ile Gly Tyr Ser Met Gly Gly
          100                 105                 110

Pro Arg Val Glu Phe Glu Val Ser Tyr Glu Thr Phe Asp Val Lys Asn
          115                 120                 125

Gln Gly Asn Asn Tyr Lys Asn Asp Ala His Arg Tyr Cys Ala Leu Gly
          130                 135                 140

Gln Gln Asp Asn Ser Gly Ile Pro Lys Thr Ser Lys Tyr Val Leu Leu
145                  150                 155                 160

Lys Ser Glu Gly Leu Leu Asp Ile Ser Phe Met Leu Asn Ala Cys Tyr
          165                 170                 175

Asp Ile Ile Asn Glu Ser Ile Pro Leu Ser Pro Tyr Ile Cys Ala Gly
          180                 185                 190

Val Gly Thr Asp Leu Ile Ser Met Phe Glu Ala Thr Asn Pro Lys Ile
          195                 200                 205

Ser Tyr Gln Gly Lys Leu Gly Leu Ser Tyr Ser Ile Asn Pro Glu Ala
          210                 215                 220

Ser Val Phe Ile Gly Gly His Phe His Lys Val Ile Gly Asn Glu Phe
225                  230                 235                 240

Arg Asp Ile Pro Thr Leu Lys Ala Phe Val Thr Ser Ser Ala Thr Pro
               245                 250                 255

Asp Leu Ala Ile Val Thr Leu Ser Val Cys His Phe Gly Ile Glu Leu
          260                 265                 270

Gly Gly Arg Phe Asn Phe
          275

<210> SEQ ID NO 11
<211> LENGTH: 843
<212> TYPE: DNA
<213> ORGANISM: Ehrlichia chaffeensis
<220> FEATURE:
<221> NAME/KEY: CDS
<222> LOCATION: (1)..(843)

<400> SEQUENCE: 11

```
atg aat tgc aaa aaa ttt ttt ata aca act aca tta gta tcg cta atg      48
Met Asn Cys Lys Lys Phe Phe Ile Thr Thr Thr Leu Val Ser Leu Met
 1               5                  10                  15 tcc ttc tta cct gga ata tca ttt tct gat gca gta cag aac gac aat      96
Ser Phe Leu Pro Gly Ile Ser Phe Ser Asp Ala Val Gln Asn Asp Asn
             20                  25                  30 gtt ggt ggt aat ttc tat atc agt ggg aaa tat gta cca agt gtt tca     144
Val Gly Gly Asn Phe Tyr Ile Ser Gly Lys Tyr Val Pro Ser Val Ser
         35                  40                  45 cat ttt ggc gta ttc tct gct aaa cag gaa aga aat aca aca acc gga     192
His Phe Gly Val Phe Ser Ala Lys Gln Glu Arg Asn Thr Thr Thr Gly
     50                  55                  60 gta ttt gga tta aag caa gat tgg gat ggc agc aca ata tct aaa aat     240
Val Phe Gly Leu Lys Gln Asp Trp Asp Gly Ser Thr Ile Ser Lys Asn
 65                  70                  75                  80 tct cca gaa aat aca ttt aac gtt cca aat tat tca ttt aaa tat gaa     288
Ser Pro Glu Asn Thr Phe Asn Val Pro Asn Tyr Ser Phe Lys Tyr Glu
                 85                  90                  95 aat aat cca ttt cta ggt ttt gca gga gct gtt ggt tat tta atg aat     336
Asn Asn Pro Phe Leu Gly Phe Ala Gly Ala Val Gly Tyr Leu Met Asn
```

-continued

```
                     100                 105                 110
ggt cca aga ata gag tta gaa atg tcc tat gaa aca ttt gat gtg aaa    384
Gly Pro Arg Ile Glu Leu Glu Met Ser Tyr Glu Thr Phe Asp Val Lys
            115                 120                 125 aac cag ggt aat aac tat aag aac gat gct cac aaa tat tat gct tta    432
Asn Gln Gly Asn Asn Tyr Lys Asn Asp Ala His Lys Tyr Tyr Ala Leu
        130                 135                 140 acc cat aac agt ggg gga aag cta agc aat gca ggt gat aag ttt gtt    480
Thr His Asn Ser Gly Gly Lys Leu Ser Asn Ala Gly Asp Lys Phe Val
145                 150                 155                 160 ttt cta aaa aat gaa gga cta ctt gat ata tca ctt atg ttg aat gca    528
Phe Leu Lys Asn Glu Gly Leu Leu Asp Ile Ser Leu Met Leu Asn Ala
                165                 170                 175 tgc tat gat gta ata agt gaa gga ata cct ttc tct cct tac ata tgt    576
Cys Tyr Asp Val Ile Ser Glu Gly Ile Pro Phe Ser Pro Tyr Ile Cys
            180                 185                 190 gca ggt gtt ggt act gat tta ata tcc atg ttt gaa gct ata aac cct    624
Ala Gly Val Gly Thr Asp Leu Ile Ser Met Phe Glu Ala Ile Asn Pro
        195                 200                 205 aaa att tct tat caa gga aag tta ggt ttg agt tac tcc ata agc cca    672
Lys Ile Ser Tyr Gln Gly Lys Leu Gly Leu Ser Tyr Ser Ile Ser Pro
210                 215                 220 gaa gct tct gtt ttt gtt ggt gga cat ttt cat aag gtg ata ggg aat    720
Glu Ala Ser Val Phe Val Gly Gly His Phe His Lys Val Ile Gly Asn
225                 230                 235                 240 gaa ttc aga gat att cct gct atg ata ccc agt acc tca act ctc aca    768
Glu Phe Arg Asp Ile Pro Ala Met Ile Pro Ser Thr Ser Thr Leu Thr
                245                 250                 255 ggt aat cac ttt act ata gta aca cta agt gta tgc cac ttt gga gtg    816
Gly Asn His Phe Thr Ile Val Thr Leu Ser Val Cys His Phe Gly Val
            260                 265                 270 gaa ctt gga gga agg ttt aac ttt taa                                843
Glu Leu Gly Gly Arg Phe Asn Phe
        275                 280

<210> SEQ ID NO 12
<211> LENGTH: 280
<212> TYPE: PRT
<213> ORGANISM: Ehrlichia chaffeensis

<400> SEQUENCE: 12

Met Asn Cys Lys Lys Phe Phe Ile Thr Thr Thr Leu Val Ser Leu Met
1               5                   10                  15

Ser Phe Leu Pro Gly Ile Ser Phe Ser Asp Ala Val Gln Asn Asp Asn
                20                  25                  30

Val Gly Gly Asn Phe Tyr Ile Ser Gly Lys Tyr Val Pro Ser Val Ser
            35                  40                  45

His Phe Gly Val Phe Ser Ala Lys Gln Glu Arg Asn Thr Thr Thr Gly
        50                  55                  60

Val Phe Gly Leu Lys Gln Asp Trp Asp Gly Ser Thr Ile Ser Lys Asn
65                  70                  75                  80

Ser Pro Glu Asn Thr Phe Asn Val Pro Asn Tyr Ser Phe Lys Tyr Glu
                85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
        115                 120                 125

Asn Gln Gly Asn Asn Tyr Lys Asn Asp Ala His Lys Tyr Tyr Ala Leu
```

-continued

```
    130                 135                 140

Thr His Asn Ser Gly Gly Lys Leu Ser Asn Ala Gly Asp Lys Phe Val
145                 150                 155                 160

Phe Leu Lys Asn Glu Gly Leu Leu Asp Ile Ser Leu Met Leu Asn Ala
                165                 170                 175

Cys Tyr Asp Val Ile Ser Glu Gly Ile Pro Phe Ser Pro Tyr Ile Cys
            180                 185                 190

Ala Gly Val Gly Thr Asp Leu Ile Ser Met Phe Glu Ala Ile Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Val Gly Gly His Phe His Lys Val Ile Gly Asn
225                 230                 235                 240

Glu Phe Arg Asp Ile Pro Ala Met Ile Pro Ser Thr Ser Thr Leu Thr
                245                 250                 255

Gly Asn His Phe Thr Ile Val Thr Leu Ser Val Cys His Phe Gly Val
            260                 265                 270

Glu Leu Gly Gly Arg Phe Asn Phe
        275                 280

<210> SEQ ID NO 13
<211> LENGTH: 894
<212> TYPE: DNA
<213> ORGANISM: Ehrlichia chaffeensis
<220> FEATURE:
<221> NAME/KEY: CDS
<222> LOCATION: (1)..(894)

<400> SEQUENCE: 13 atg gaa aat ctc atg aat aag aaa aac aaa ttc ttt aca ata agt aca       48
Met Glu Asn Leu Met Asn Lys Lys Asn Lys Phe Phe Thr Ile Ser Thr
  1               5                  10                  15 gca atg gta tgc tta ttg tta tta cct ggt ata tca ttt tca gaa act       96
Ala Met Val Cys Leu Leu Leu Leu Pro Gly Ile Ser Phe Ser Glu Thr
             20                  25                  30 ata aac aac agt gct aaa aaa cag cct ggg tta tat atc agt ggg cag      144
Ile Asn Asn Ser Ala Lys Lys Gln Pro Gly Leu Tyr Ile Ser Gly Gln
         35                  40                  45 tac aaa cct agt gtt tca gtt ttt agt aat ttt tca gta aaa gaa act      192
Tyr Lys Pro Ser Val Ser Val Phe Ser Asn Phe Ser Val Lys Glu Thr
     50                  55                  60 aat gtt ccc aca aag cag tta ata gca ctt aaa aaa gac att aat tct      240
Asn Val Pro Thr Lys Gln Leu Ile Ala Leu Lys Lys Asp Ile Asn Ser
 65                  70                  75                  80 gtt gca gtt ggt agt aat gct act aca ggt att agc aat cca ggt aat      288
Val Ala Val Gly Ser Asn Ala Thr Thr Gly Ile Ser Asn Pro Gly Asn
                 85                  90                  95 ttc aca att cct tat act gca gaa ttt caa gat aat gtt gcc aat ttc      336
Phe Thr Ile Pro Tyr Thr Ala Glu Phe Gln Asp Asn Val Ala Asn Phe
            100                 105                 110 aat ggg gct gtt ggt tac tct ttt cct gat agt cta aga att gaa ata      384
Asn Gly Ala Val Gly Tyr Ser Phe Pro Asp Ser Leu Arg Ile Glu Ile
        115                 120                 125 gag gga ttt cat gaa aaa ttt gat gtc aaa aac cct gga ggt tac aca      432
Glu Gly Phe His Glu Lys Phe Asp Val Lys Asn Pro Gly Gly Tyr Thr
    130                 135                 140 caa gta aaa gat gcg tac cgt tat ttt gca cta gca cgt gat tta aaa      480
Gln Val Lys Asp Ala Tyr Arg Tyr Phe Ala Leu Ala Arg Asp Leu Lys
145                 150                 155                 160
```

-continued

```
gat ggc ttc ttt gaa cct aaa gcg gaa gat aca ggt gtt tat cat act      528
Asp Gly Phe Phe Glu Pro Lys Ala Glu Asp Thr Gly Val Tyr His Thr
            165                 170                 175 gtt atg aaa aat gat gga tta tct att tta tct act atg gtt aac gtc      576
Val Met Lys Asn Asp Gly Leu Ser Ile Leu Ser Thr Met Val Asn Val
        180                 185                 190 tgt tac gat ttt tct gta gat gaa tta cca gtc tta cct tat ata tgt      624
Cys Tyr Asp Phe Ser Val Asp Glu Leu Pro Val Leu Pro Tyr Ile Cys
    195                 200                 205 gca ggt atg ggt ata aac gcc ata gaa ttc ttc gac gct tta cat gta      672
Ala Gly Met Gly Ile Asn Ala Ile Glu Phe Phe Asp Ala Leu His Val
210                 215                 220 aaa ttt gct tac caa ggc aaa cta ggt att agc tat caa cta ttt act      720
Lys Phe Ala Tyr Gln Gly Lys Leu Gly Ile Ser Tyr Gln Leu Phe Thr
225                 230                 235                 240 aaa gta aat tta ttc ctt gat ggg tat tac cat caa gta ata ggc aat      768
Lys Val Asn Leu Phe Leu Asp Gly Tyr Tyr His Gln Val Ile Gly Asn
            245                 250                 255 caa ttc aaa aac tta aac gta aac cat gtt tac aca ctt aaa gaa tct      816
Gln Phe Lys Asn Leu Asn Val Asn His Val Tyr Thr Leu Lys Glu Ser
        260                 265                 270 cct aaa gtc aca tct gca gta gct aca ctt gac att gca tac ttt ggt      864
Pro Lys Val Thr Ser Ala Val Ala Thr Leu Asp Ile Ala Tyr Phe Gly
    275                 280                 285 ggc gaa gtt gga ata aga ttc aca ttt taa                              894
Gly Glu Val Gly Ile Arg Phe Thr Phe
290                 295
```

<210> SEQ ID NO 14
<211> LENGTH: 297
<212> TYPE: PRT
<213> ORGANISM: Ehrlichia chaffeensis

<400> SEQUENCE: 14

```
Met

```
                            180                 185                 190
Cys Tyr Asp Phe Ser Val Asp Glu Leu Pro Val Leu Pro Tyr Ile Cys
        195                 200                 205

Ala Gly Met Gly Ile Asn Ala Ile Glu Phe Phe Asp Ala Leu His Val
    210                 215                 220

Lys Phe Ala Tyr Gln Gly Lys Leu Gly Ile Ser Tyr Gln Leu Phe Thr
225                 230                 235                 240

Lys Val Asn Leu Phe Leu Asp Gly Tyr Tyr His Gln Val Ile Gly Asn
                245                 250                 255

Gln Phe Lys Asn Leu Asn Val Asn His Val Tyr Thr Leu Lys Glu Ser
            260                 265                 270

Pro Lys Val Thr Ser Ala Val Ala Thr Leu Asp Ile Ala Tyr Phe Gly
        275                 280                 285

Gly Glu Val Gly Ile Arg Phe Thr Phe
    290                 295
```

```
<210> SEQ ID NO 15
<211> LENGTH: 591
<212> TYPE: DNA
<213> ORGANISM: Ehrlichia chaffeensis
<220> FEATURE:
<221> NAME/KEY: CDS
<222> LOCATION: (1)..(591)

<400> SEQUENCE: 15 atg ata tat aaa gaa aaa ctt act aga gtg gga gaa tat atc tta gca      48
Met Ile Tyr Lys Glu Lys Leu Thr Arg Val Gly Glu Tyr Ile Leu Ala
  1               5                  10                  15 tat tta tca ttt att ctt tct act tat atc ttt cta gtg ctg gta aat      96
Tyr Leu Ser Phe Ile Leu Ser Thr Tyr Ile Phe Leu Val Leu Val Asn
                 20                  25                  30 att att aga tat aac agc ctt gct ata tgt gtt atc agt cta cta aga     144
Ile Ile Arg Tyr Asn Ser Leu Ala Ile Cys Val Ile Ser Leu Leu Arg
             35                  40                  45 act aat atc ttt aac gtt agc aca aaa aaa tta ata aaa gat aaa tgt     192
Thr Asn Ile Phe Asn Val Ser Thr Lys Lys Leu Ile Lys Asp Lys Cys
         50                  55                  60 cgt gat act aag ttt agt aac atg aat tgt tat ttg tac ggt aaa ccg     240
Arg Asp Thr Lys Phe Ser Asn Met Asn Cys Tyr Leu Tyr Gly Lys Pro
 65                  70                  75                  80 tta aat tta caa att ttt tat gga ata ttt tcc ttt att aga aac ttt     288
Leu Asn Leu Gln Ile Phe Tyr Gly Ile Phe Ser Phe Ile Arg Asn Phe
                 85                  90                  95 caa aat aac aca cta ata att cct aat gat agt aaa tgc ggc ttc tat     336
Gln Asn Asn Thr Leu Ile Ile Pro Asn Asp Ser Lys Cys Gly Phe Tyr
            100                 105                 110 acc acg tta tgg gat aat cca gca cta cat tat aca tat aca ctt act     384
Thr Thr Leu Trp Asp Asn Pro Ala Leu His Tyr Thr Tyr Thr Leu Thr
        115                 120                 125 ggc agt gag tac cgt aat ttt ttt gac att cta tat gaa aac att atc     432
Gly Ser Glu Tyr Arg Asn Phe Phe Asp Ile Leu Tyr Glu Asn Ile Ile
    130                 135                 140 tgt caa tgt aaa tta ctt att aac tat aac cgt tct gta tta aac caa     480
Cys Gln Cys Lys Leu Leu Ile Asn Tyr Asn Arg Ser Val Leu Asn Gln
145                 150                 155                 160 cat aat aaa aat act ctc gta ata ata cca ata cct aat gct aga gag     528
His Asn Lys Asn Thr Leu Val Ile Ile Pro Ile Pro Asn Ala Arg Glu
                165                 170                 175 ttc agt aat gaa att cga gta agg aat ata tca ata aat aag gaa agt     576
Phe Ser Asn Glu Ile Arg Val Arg Asn Ile Ser Ile Asn Lys Glu Ser
```

```
Phe Ser Asn Glu Ile Arg Val Arg Asn Ile Ser Ile Asn Lys Glu Ser
            180                 185                 190 tct tat gag tgc taa                                                    591
Ser Tyr Glu Cys
        195

<210> SEQ ID NO 16
<211> LENGTH: 196
<212> TYPE: PRT
<213> ORGANISM: Ehrlichia chaffeensis

<400> SEQUENCE: 16

Met Ile Tyr Lys Glu Lys Leu Thr Arg Val Gly Glu Tyr Ile Leu Ala
  1               5                  10                  15

Tyr Leu Ser Phe Ile Leu Ser Thr Tyr Ile Phe Leu Val Leu Val Asn
             20                  25                  30

Ile Ile Arg Tyr Asn Ser Leu Ala Ile Cys Val Ile Ser Leu Leu Arg
         35                  40                  45

Thr Asn Ile Phe Asn Val Ser Thr Lys Lys Leu Ile Lys Asp Lys Cys
     50                  55                  60

Arg Asp Thr Lys Phe Ser Asn Met Asn Cys Tyr Leu Tyr Gly Lys Pro
 65                  70                  75                  80

Leu Asn Leu Gln Ile Phe Tyr Gly Ile Phe Ser Phe Ile Arg Asn Phe
                 85                  90                  95

Gln Asn Asn Thr Leu Ile Ile Pro Asn Asp Ser Lys Cys Gly Phe Tyr
            100                 105                 110

Thr Thr Leu Trp Asp Asn Pro Ala Leu His Tyr Thr Tyr Thr Leu Thr
        115                 120                 125

Gly Ser Glu Tyr Arg Asn Phe Phe Asp Ile Leu Tyr Glu Asn Ile Ile
    130                 135                 140

Cys Gln Cys Lys Leu Leu Ile Asn Tyr Asn Arg Ser Val Leu Asn Gln
145                 150                 155                 160

His Asn Lys Asn Thr Leu Val Ile Ile Pro Ile Pro Asn Ala Arg Glu
                165                 170                 175

Phe Ser Asn Glu Ile Arg Val Arg Asn Ile Ser Ile Asn Lys Glu Ser
            180                 185                 190

Ser Tyr Glu Cys
        195

<210> SEQ ID NO 17
<211> LENGTH: 876
<212> TYPE: DNA
<213> ORGANISM: Ehrlichia chaffeensis
<220> FEATURE:
<221> NAME/KEY: CDS
<222> LOCATION: (1)..(876)

<400> SEQUENCE: 17 atg aat aaa aaa aac aag ttt att ata gct aca gca ttg gta tat tta    48
Met Asn Lys Lys Asn Lys Phe Ile Ile Ala Thr Ala Leu Val Tyr Leu
  1               5                  10                  15 ctg tca tta cct agt gta tcg ttt tca gag gtt aca aac agc agt att    96
Leu Ser Leu Pro Ser Val Ser Phe Ser Glu Val Thr Asn Ser Ser Ile
             20                  25                  30 aaa aaa cac tct ggg tta tat att agt gga caa tac aaa cca agt gtt   144
Lys Lys His Ser Gly Leu Tyr Ile Ser Gly Gln Tyr Lys Pro Ser Val
         35                  40                  45 tct gtt ttt agt agt ttc tca att aaa gaa act aac act atc aca aaa   192
Ser Val Phe Ser Ser Phe Ser Ile Lys Glu Thr Asn Thr Ile Thr Lys
```

```
              50                   55                   60
aat ctt ata gcg tta aaa aaa gat att aac tct ctt gaa gtt aac gcc      240
Asn Leu Ile Ala Leu Lys Lys Asp Ile Asn Ser Leu Glu Val Asn Ala
 65                  70                   75                  80 gat gct agt caa ggt att agt cat cca gga aat ttt act ata cct tat      288
Asp Ala Ser Gln Gly Ile Ser His Pro Gly Asn Phe Thr Ile Pro Tyr
                     85                   90                  95 ata gca gca ttt gaa gat aat gct ttt aat ttc aac ggt gct att ggt      336
Ile Ala Ala Phe Glu Asp Asn Ala Phe Asn Phe Asn Gly Ala Ile Gly
                100                  105                 110 tac att act gaa ggt cta agg att gaa ata gaa ggt tcc tat gaa gaa      384
Tyr Ile Thr Glu Gly Leu Arg Ile Glu Ile Glu Gly Ser Tyr Glu Glu
            115                  120                 125 ttt gat gct aaa aac cct gga ggt tat ggt cta aat gat gcc ttt cgg      432
Phe Asp Ala Lys Asn Pro Gly Gly Tyr Gly Leu Asn Asp Ala Phe Arg
        130                  135                 140 tac ttt gct tta gca cgt gat atg gaa agc aac aag ttc caa cca aaa      480
Tyr Phe Ala Leu Ala Arg Asp Met Glu Ser Asn Lys Phe Gln Pro Lys
145                  150                 155                 160 gca caa agc tca caa aaa gta ttt cac act gta atg aag agt gat ggg      528
Ala Gln Ser Ser Gln Lys Val Phe His Thr Val Met Lys Ser Asp Gly
                 165                 170                 175 tta tct ata ata tct atc atg gtt aac ggc tgt tat gat ttt tct tcg      576
Leu Ser Ile Ile Ser Ile Met Val Asn Gly Cys Tyr Asp Phe Ser Ser
            180                  185                 190 gat aat tta tta gta tca cct tat ata tgt gga ggt ata ggt gtg gat      624
Asp Asn Leu Leu Val Ser Pro Tyr Ile Cys Gly Gly Ile Gly Val Asp
        195                  200                 205 gca ata gaa ttt ttt gac gca tta cac att aaa ctt gcg tgc caa agc      672
Ala Ile Glu Phe Phe Asp Ala Leu His Ile Lys Leu Ala Cys Gln Ser
210                  215                 220 aaa tta ggc atc act tat caa tta tct tat aat atc agc tta ttt gct      720
Lys Leu Gly Ile Thr Tyr Gln Leu Ser Tyr Asn Ile Ser Leu Phe Ala
225                  230                 235                 240 gat gga tat tat cat caa gta ata ggt aac caa ttc aga aat tta aac      768
Asp Gly Tyr Tyr His Gln Val Ile Gly Asn Gln Phe Arg Asn Leu Asn
                 245                 250                 255 gtt caa cat gta gct gaa ctt aat gat gca cct aaa gtt aca tct gca      816
Val Gln His Val Ala Glu Leu Asn Asp Ala Pro Lys Val Thr Ser Ala
            260                  265                 270 gtt gcc aca ctt aat gtt gga tat ttc ggc gct gaa gtt gga gta aga      864
Val Ala Thr Leu Asn Val Gly Tyr Phe Gly Ala Glu Val Gly Val Arg
        275                  280                 285 ttt ata ttt taa                                                      876
Phe Ile Phe
    290

<210> SEQ ID NO 18
<211> LENGTH: 291
<212> TYPE: PRT
<213> ORGANISM: Ehrlichia chaffeensis

<400> SEQUENCE: 18

Met Asn Lys Lys Asn Lys Phe Ile Ile Ala Thr Ala Leu Val Tyr Leu
 1               5                  10                  15

Leu Ser Leu Pro Ser Val Ser Phe Ser Glu Val Thr Asn Ser Ser Ile
            20                  25                  30

Lys Lys His Ser Gly Leu Tyr Ile Ser Gly Gln Tyr Lys Pro Ser Val
        35                  40                  45
```

-continued

```
Ser Val Phe Ser Ser Phe Ser Ile Lys Glu Thr Asn Thr Ile Thr Lys
    50                  55                  60

Asn Leu Ile Ala Leu Lys Lys Asp Ile Asn Ser Leu Glu Val Asn Ala
65                  70                  75                  80

Asp Ala Ser Gln Gly Ile Ser His Pro Gly Asn Phe Thr Ile Pro Tyr
                85                  90                  95

Ile Ala Ala Phe Glu Asp Asn Ala Phe Asn Phe Asn Gly Ala Ile Gly
            100                 105                 110

Tyr Ile Thr Glu Gly Leu Arg Ile Glu Ile Gly Ser Tyr Glu Glu
        115                 120                 125

Phe Asp Ala Lys Asn Pro Gly Gly Tyr Gly Leu Asn Asp Ala Phe Arg
    130                 135                 140

Tyr Phe Ala Leu Ala Arg Asp Met Glu Ser Asn Lys Phe Gln Pro Lys
145                 150                 155                 160

Ala Gln Ser Ser Gln Lys Val Phe His Thr Val Met Lys Ser Asp Gly
                165                 170                 175

Leu Ser Ile Ile Ser Ile Met Val Asn Gly Cys Tyr Asp Phe Ser Ser
            180                 185                 190

Asp Asn Leu Leu Val Ser Pro Tyr Ile Cys Gly Gly Ile Gly Val Asp
        195                 200                 205

Ala Ile Glu Phe Phe Asp Ala Leu His Ile Lys Leu Ala Cys Gln Ser
    210                 215                 220

Lys Leu Gly Ile Thr Tyr Gln Leu Ser Tyr Asn Ile Ser Leu Phe Ala
225                 230                 235                 240

Asp Gly Tyr Tyr His Gln Val Ile Gly Asn Gln Phe Arg Asn Leu Asn
                245                 250                 255

Val Gln His Val Ala Glu Leu Asn Asp Ala Pro Lys Val Thr Ser Ala
            260                 265                 270

Val Ala Thr Leu Asn Val Gly Tyr Phe Gly Ala Glu Val Gly Val Arg
        275                 280                 285

Phe Ile Phe
    290

<210> SEQ ID NO 19
<211> LENGTH: 396
<212> TYPE: DNA
<213> ORGANISM: Ehrlichia chaffeensis
<220> FEATURE:
<221> NAME

```
ata tat tat cat aaa gtc atg ggt aac aga ttt aaa aat ttg tac atg       288
Ile Tyr Tyr His Lys Val Met Gly Asn Arg Phe Lys Asn Leu Tyr Met
             85                  90                  95 caa tat gta gct gat cct aat att tct gaa gaa act ata cct ata tta       336
Gln Tyr Val Ala Asp Pro Asn Ile Ser Glu Glu Thr Ile Pro Ile Leu
        100                 105                 110 gca aaa ctt gat att ggt tat ttt gga agt gaa att gga ata agg ttt       384
Ala Lys Leu Asp Ile Gly Tyr Phe Gly Ser Glu Ile Gly Ile Arg Phe
        115                 120                 125 atg ttt aac taa                                                       396
Met Phe Asn
    130

<210> SEQ ID NO 20
<211> LENGTH: 131
<212> TYPE: PRT
<213> ORGANISM: Ehrlichia chaffeensis

<400> SEQUENCE: 20

Ser Arg Ile His Asp Glu Asn Tyr Ala Ile Thr Thr Asn Asn Lys Leu
 1               5                  10                  15

Ser Ile Ala Ser Ile Met Val Asn Thr Cys Tyr Asp Ile Ser Ile Asn
            20                  25                  30

Asn Thr Ser Ile Val Pro Tyr Leu Cys Thr Gly Ile Gly Glu Asp Leu
        35                  40                  45

Val Gly Leu Phe Asn Thr Ile His Phe Lys Leu Ala Tyr Gln Gly Lys
    50                  55                  60

Val Gly Met Ser Tyr Leu Ile Asn Asn Ile Leu Leu Phe Ser Asp
65                  70                  75                  80

Ile Tyr Tyr His Lys Val Met Gly Asn Arg Phe Lys Asn Leu Tyr Met
                85                  90                  95

Gln Tyr Val Ala Asp Pro Asn Ile Ser Glu Glu Thr Ile Pro Ile Leu
            100                 105                 110

Ala Lys Leu Asp Ile Gly Tyr Phe Gly Ser Glu Ile Gly Ile Arg Phe
        115                 120                 125

Met Phe Asn
    130

<210> SEQ ID NO 21
<211> LENGTH: 888
<212> TYPE: DNA
<213> ORGANISM: Ehrlichia chaffeensis
<220> FEATURE:
<221> NAME/KEY: CDS
<222> LOCATION: (1)..(888)

<400> SEQUENCE: 21 atg aca aag aaa ttt aat ttt gta aat gtt ata tta aca ttt ttg tta       48
Met Thr Lys Lys Phe Asn Phe Val Asn Val Ile Leu Thr Phe Leu Leu
 1               5                  10                  15 ttt ctt ttc cca ctt aag tca ttt aca aca tat gca aat aat aac aca       96
Phe Leu Phe Pro Leu Lys Ser Phe Thr Thr Tyr Ala Asn Asn Asn Thr
            20                  25                  30 atc act caa aaa gtt gga ttg tac ata agt ggt caa tat aag cca agt      144
Ile Thr Gln Lys Val Gly Leu Tyr Ile Ser Gly Gln Tyr Lys Pro Ser
        35                  40                  45 att cct cat ttc aag aat ttt tca gta gaa gaa aat gac aaa gta gta      192
Ile Pro His Phe Lys Asn Phe Ser Val Glu Glu Asn Asp Lys Val Val
    50                  55                  60 gat ttg ata ggt ctt aca act gat gtt aca tat atc aca gaa cat ata      240
```

```
Asp Leu Ile Gly Leu Thr Thr Asp Val Thr Tyr Ile Thr Glu His Ile
 65                  70                  75                  80 tta cga gat aat aca aaa ttc aac act cat tat att gca aag ttc aag    288
Leu Arg Asp Asn Thr Lys Phe Asn Thr His Tyr Ile Ala Lys Phe Lys
                 85                  90                  95 aac aat ttt ata aat ttc agc agt gca att ggt tat tat tct ggg caa    336
Asn Asn Phe Ile Asn Phe Ser Ser Ala Ile Gly Tyr Tyr Ser Gly Gln
             100                 105                 110 gga cca agg tta gaa ata gaa agc tct tat ggg gat ttt gat gtt gta    384
Gly Pro Arg Leu Glu Ile Glu Ser Ser Tyr Gly Asp Phe Asp Val Val
         115                 120                 125 aat tat aaa aat tat gca gta caa gat gtt aat aga tat ttt gct tta    432
Asn Tyr Lys Asn Tyr Ala Val Gln Asp Val Asn Arg Tyr Phe Ala Leu
     130                 135                 140 gta cgt gaa aaa aat ggt tca aat ttc tct cca aaa cca cat gaa act    480
Val Arg Glu Lys Asn Gly Ser Asn Phe Ser Pro Lys Pro His Glu Thr
145                 150                 155                 160 agt caa ccc tct gac agt aat cct aaa aag tct ttt tat act tta atg    528
Ser Gln Pro Ser Asp Ser Asn Pro Lys Lys Ser Phe Tyr Thr Leu Met
                 165                 170                 175 aag aat aat ggg gta ttt gtt gca tca gta ata atc aac ggt tgt tat    576
Lys Asn Asn Gly Val Phe Val Ala Ser Val Ile Ile Asn Gly Cys Tyr
             180                 185                 190 gat ttt tct ttt aat aac aca aca ata tca cct tac gta tgt ata gga    624
Asp Phe Ser Phe Asn Asn Thr Thr Ile Ser Pro Tyr Val Cys Ile Gly
         195                 200                 205 gtt gga gga gat ttt ata gag ttt ttt gaa gta atg cat atc aag ttt    672
Val Gly Gly Asp Phe Ile Glu Phe Phe Glu Val Met His Ile Lys Phe
     210                 215                 220 gct tgc caa agt aag gtt ggt att agc tat cca ata tct ccc tct att    720
Ala Cys Gln Ser Lys Val Gly Ile Ser Tyr Pro Ile Ser Pro Ser Ile
225                 230                 235                 240 act att ttt gct gat gca vat tat cac aag gtc ata aat aat aaa ttt    768
Thr Ile Phe Ala Asp Ala Xaa Tyr His Lys Val Ile Asn Asn Lys Phe
                 245                 250                 255 aac aac cta cat gtt aag tat tca tat gaa ctt aaa aac tca cct acc    816
Asn Asn Leu His Val Lys Tyr Ser Tyr Glu Leu Lys Asn Ser Pro Thr
             260                 265                 270 att acc tct gca aca gcc aaa cta aac att gaa tat ttt ggt ggt gaa    864
Ile Thr Ser Ala Thr Ala Lys Leu Asn Ile Glu Tyr Phe Gly Gly Glu
         275                 280                 285 gtt ggg atg aga ttt ata ttt taa                                    888
Val Gly Met Arg Phe Ile Phe
     290                 295

<210> SEQ ID NO 22
<211> LENGTH: 295
<212> TYPE: PRT
<213> ORGANISM: Ehrlichia chaffeensis

<400> SEQUENCE: 22

Met Thr Lys Lys Phe Asn Phe Val Asn Val Ile Leu Thr Phe Leu Leu
  1               5                  10                  15

Phe Leu Phe Pro Leu Lys Ser Phe Thr Thr Tyr Ala Asn Asn Asn Thr
                 20                  25                  30

Ile Thr Gln Lys Val Gly Leu Tyr Ile Ser Gly Gln Tyr Lys Pro Ser
             35                  40                  45

Ile Pro His Phe Lys Asn Phe Ser Val Glu Glu Asn Asp Lys Val Val
         50                  55                  60
```

-continued

```
Asp Leu Ile Gly Leu Thr Thr Asp Val Thr Tyr Ile Thr Glu His Ile
 65                  70                  75                  80

Leu Arg Asp Asn Thr Lys Phe Asn Thr His Tyr Ile Ala Lys Phe Lys
                 85                  90                  95

Asn Asn Phe Ile Asn Phe Ser Ser Ala Ile Gly Tyr Tyr Ser Gly Gln
            100                 105                 110

Gly Pro Arg Leu Glu Ile Glu Ser Ser Tyr Gly Asp Phe Asp Val Val
        115                 120                 125

Asn Tyr Lys Asn Tyr Ala Val Gln Asp Val Asn Arg Tyr Phe Ala Leu
    130                 135                 140

Val Arg Glu Lys Asn Gly Ser Asn Phe Ser Pro Lys Pro His Glu Thr
145                 150                 155                 160

Ser Gln Pro Ser Asp Ser Asn Pro Lys Lys Ser Phe Tyr Thr Leu Met
                165                 170                 175

Lys Asn Asn Gly Val Phe Val Ala Ser Val Ile Ile Asn Gly Cys Tyr
            180                 185                 190

Asp Phe Ser Phe Asn Asn Thr Thr Ile Ser Pro Tyr Val Cys Ile Gly
        195                 200                 205

Val Gly Gly Asp Phe Ile Glu Phe Phe Glu Val Met His Ile Lys Phe
    210                 215                 220

Ala Cys Gln Ser Lys Val Gly Ile Ser Tyr Pro Ile Ser Pro Ser Ile
225                 230                 235                 240

Thr Ile Phe Ala Asp Ala Xaa Tyr His Lys Val Ile Asn Asn Lys Phe
                245                 250                 255

Asn Asn Leu His Val Lys Tyr Ser Tyr Glu Leu Lys Asn Ser Pro Thr
            260                 265                 270

Ile Thr Ser Ala Thr Ala Lys Leu Asn Ile Glu Tyr Phe Gly Gly Glu
        275                 280                 285

Val Gly Met Arg Phe Ile Phe
    290                 295
```

<210> SEQ ID NO 23
<211> LENGTH: 840
<212> TYPE: DNA
<213> ORGANISM: Ehrlichia chaffeensis
<220

-continued

```
aat gct gct agt ttc agt gga gca att gga tat tct tac ccc gaa agt      336
Asn Ala Ala Ser Phe Ser Gly Ala Ile Gly Tyr Ser Tyr Pro Glu Ser
            100                 105                 110 cta aga ctt gaa ctt gaa ggt tct tac gaa aaa ttt gat gtc aaa gat      384
Leu Arg Leu Glu Leu Glu Gly Ser Tyr Glu Lys Phe Asp Val Lys Asp
            115                 120                 125 cct aaa gac tac tca gca aaa gat gct ttt agg ttt ttt gct cta gca      432
Pro Lys Asp Tyr Ser Ala Lys Asp Ala Phe Arg Phe Phe Ala Leu Ala
        130                 135                 140 cgt aat acg tct act act gtt cct gat gct caa aaa tat aca gtt atg      480
Arg Asn Thr Ser Thr Thr Val Pro Asp Ala Gln Lys Tyr Thr Val Met
145                 150                 155                 160 aag aat aat ggc tta tct gtt gca tca atc atg atc aat ggt tgt tat      528
Lys Asn Asn Gly Leu Ser Val Ala Ser Ile Met Ile Asn Gly Cys Tyr
                165                 170                 175 gat cta tct ttt aat aat tta gtc gta tca cct tat ata tgt gca ggt      576
Asp Leu Ser Phe Asn Asn Leu Val Val Ser Pro Tyr Ile Cys Ala Gly
            180                 185                 190 att ggt gaa gat ttc att gaa ttt ttt gat act ttg cac att aaa ctt      624
Ile Gly Glu Asp Phe Ile Glu Phe Phe Asp Thr Leu His Ile Lys Leu
        195                 200                 205 gct tat caa gga aaa cta ggt att agt tat tac ttc ttt cct aag att      672
Ala Tyr Gln Gly Lys Leu Gly Ile Ser Tyr Tyr Phe Phe Pro Lys Ile
    210                 215                 220 aat gta ttt gct ggt ggg tac tat cat aga gtt ata ggg aat aaa ttt      720
Asn Val Phe Ala Gly Gly Tyr Tyr His Arg Val Ile Gly Asn Lys Phe
225                 230                 235                 240 aaa aat tta aat gtt aac cat gtt gtt aca ctt gat gaa ttt cct aaa      768
Lys Asn Leu Asn Val Asn His Val Val Thr Leu Asp Glu Phe Pro Lys
                245                 250                 255 gca act tct gca gta gct aca ctt aat gtt gct tat ttt ggt ggt gaa      816
Ala Thr Ser Ala Val Ala Thr Leu Asn Val Ala Tyr Phe Gly Gly Glu
            260                 265                 270 gct gga gta aag ttt aca ttt taa                                       840
Ala Gly Val Lys Phe Thr Phe
        275                 280
```

<210> SEQ ID NO 24
<211> LENGTH: 279
<212> TYPE: PRT
<213> ORGANISM: Ehrlichia chaffeensis

<400> SEQUENCE: 24

```
Met Ser Lys Lys Phe Ile Thr Ile Gly Thr Val Leu Ala Ser Leu
 1               5                  10                  15

Leu Ser Phe Leu Ser Ile Glu Ser Phe Ser Ala Ile Asn His Asn His
            20                  25                  30

Thr Gly Asn Asn Thr Ser Gly Ile Tyr Ile Thr Gly Gln Tyr Arg Pro
        35                  40                  45

Gly Val Ser His Phe Ser Asn Phe Ser Val Lys Glu Thr Asn Val Asp
    50                  55                  60

Thr Ile Gln Leu Val Gly Tyr Lys Lys Ser Ala Ser Ser Ile Asp Pro
65                  70                  75                  80

Asn Thr Tyr Ser Asn Phe Gln Gly Pro Tyr Thr Val Thr Phe Gln Asp
                85                  90                  95

Asn Ala Ala Ser Phe Ser Gly Ala Ile Gly Tyr Ser Tyr Pro Glu Ser
            100                 105                 110

Leu Arg Leu Glu Leu Glu Gly Ser Tyr Glu Lys Phe Asp Val Lys Asp
```

```
                115                 120                 125
Pro Lys Asp Tyr Ser Ala Lys Asp Ala Phe Arg Phe Ala Leu Ala
    130                 135                 140

Arg Asn Thr Ser Thr Thr Val Pro Asp Ala Gln Lys Tyr Thr Val Met
145                 150                 155                 160

Lys Asn Asn Gly Leu Ser Val Ala Ser Ile Met Ile Asn Gly Cys Tyr
                165                 170                 175

Asp Leu Ser Phe Asn Asn Leu Val Val Ser Pro Tyr Ile Cys Ala Gly
            180                 185                 190

Ile Gly Glu Asp Phe Ile Glu Phe Phe Asp Thr Leu His Ile Lys Leu
        195                 200                 205

Ala Tyr Gln Gly Lys Leu Gly Ile Ser Tyr Tyr Phe Phe Pro Lys Ile
    210                 215                 220

Asn Val Phe Ala Gly Gly Tyr Tyr His Arg Val Ile Gly Asn Lys Phe
225                 230                 235                 240

Lys Asn Leu Asn Val Asn His Val Val Thr Leu Asp Glu Phe Pro Lys
                245                 250                 255

Ala Thr Ser Ala Val Ala Thr Leu Asn Val Ala Tyr Phe Gly Gly Glu
            260                 265                 270

Ala Gly Val Lys Phe Thr Phe
        275

<210> SEQ ID NO 25
<211> LENGTH: 852
<212> TYPE: DNA
<213> ORGANISM: Ehrlichia chaffeensis
<220> FEAT

```
tta gca aga gga att gat aat ctt caa aaa tat cct gaa aca aat aag      480
Leu Ala Arg Gly Ile Asp Asn Leu Gln Lys Tyr Pro Glu Thr Asn Lys
145                 150                 155                 160 tat gtt gtt ata aag aac aat ggc tta tct gtc gca tcc att ata atc      528
Tyr Val Val Ile Lys Asn Asn Gly Leu Ser Val Ala Ser Ile Ile Ile
                165                 170                 175 aat ggc tgt tat gat ttt tct tta aac aat tta aaa gta tca cct tac      576
Asn Gly Cys Tyr Asp Phe Ser Leu Asn Asn Leu Lys Val Ser Pro Tyr
            180                 185                 190 ata tgc gta ggg ttt ggt ggg gac att ata gaa ttt ttt agt gct gta      624
Ile Cys Val Gly Phe Gly Gly Asp Ile Ile Glu Phe Phe Ser Ala Val
        195                 200                 205 agt ttt aaa ttt gct tat caa ggt aag gta ggt atc agt tat cca tta      672
Ser Phe Lys Phe Ala Tyr Gln Gly Lys Val Gly Ile Ser Tyr Pro Leu
    210                 215                 220 ttc tct aat atg att ata ttt gct gac gga tat tac cat aag gtc ata      720
Phe Ser Asn Met Ile Ile Phe Ala Asp Gly Tyr Tyr His Lys Val Ile
225                 230                 235                 240 gga aat aaa ttt aac aat tta aat gtt caa cac gtt gtt agt ctt aac      768
Gly Asn Lys Phe Asn Asn Leu Asn Val Gln His Val Val Ser Leu Asn
                245                 250                 255 agt cat cct aag tct act ttt gca gta gct act ctt aat gtt gag tat      816
Ser His Pro Lys Ser Thr Phe Ala Val Ala Thr Leu Asn Val Glu Tyr
            260                 265                 270 ttc ggt agt gaa ttt ggg tta aaa ttt ata ttt taa                      852
Phe Gly Ser Glu Phe Gly Leu Lys Phe Ile Phe
        275                 280
```

<210> SEQ ID NO 26
<211> LENGTH: 283
<212> TYPE: PRT
<213> ORGANISM: Ehrlichia chaffeensis

<400> SEQUENCE: 26

```
Met Ser Ala Lys Lys Leu Phe Ile Ile Gly Ser Val Leu Val Cys
 1               5                  10                  15

Leu Val Ser Tyr Leu Pro Thr Lys Ser Leu Ser Asn Leu Asn Asn Ile
                20                  25                  30

Asn Asn Asn Thr Lys Cys Thr Gly Leu Tyr Val Ser Gly Gln Tyr Lys
            35                  40                  45

Pro Thr Val Ser His Phe Ser Asn Phe Ser Leu Lys Glu Thr Tyr Thr
        50                  55                  60

Asp Thr Lys Glu Leu Leu Gly Leu Ala Lys Asp Ile Lys Ser Ile Thr
65                  70                  75                  80

Asp Ile Thr Thr Asn Lys Lys Phe Asn Ile Pro Tyr Asn Thr Lys Phe
                85                  90                  95

Gln Asp Asn Ala Val Ser Phe Ser Ala Ala Val Gly Tyr Ile Ser Gln
            100                 105                 110

Asp Ser Pro Arg Val Glu Val Glu Trp Ser Tyr Glu Phe Asp Val
        115                 120                 125

Lys Asn Pro Gly Asn Tyr Val Val Ser Glu Ala Phe Arg Tyr Ile Ala
130                 135                 140

Leu Ala Arg Gly Ile Asp Asn Leu Gln Lys Tyr Pro Glu Thr Asn Lys
145                 150                 155                 160

Tyr Val Val Ile Lys Asn Asn Gly Leu Ser Val Ala Ser Ile Ile Ile
                165                 170                 175

Asn Gly Cys Tyr Asp Phe Ser Leu Asn Asn Leu Lys Val Ser Pro Tyr
            180                 185                 190
```

```
Ile Cys Val Gly Phe Gly Gly Asp Ile Ile Glu Phe Phe Ser Ala Val
            195                 200                 205

Ser Phe Lys Phe Ala Tyr Gln Gly Lys Val Gly Ile Ser Tyr Pro Leu
            210                 215                 220

Phe Ser Asn Met Ile Ile Phe Ala Asp Gly Tyr Tyr His Lys Val Ile
225                 230                 235                 240

Gly Asn Lys Phe Asn Asn Leu Asn Val Gln His Val Val Ser Leu Asn
                245                 250                 255

Ser His Pro Lys Ser Thr Phe Ala Val Ala Thr Leu Asn Val Glu Tyr
            260                 265                 270

Phe Gly Ser Glu Phe Gly Leu Lys Phe Ile Phe
            275                 280

<210> SEQ ID NO 27
<211> LENGTH: 828
<212> TYPE: DNA
<213> ORGANISM: Ehrlichia chaffeensis
<220> FEATURE:
<221> NAME/KEY: CDS
<222> LOCATION: (1)..(828)

<400> SEQUENCE: 27
```

| | | |
|---|---|---|
| atg agt aaa aaa aat ttt att aca ata gga gca aca ctt att cat atg<br>Met Ser Lys Lys Asn Phe Ile Thr Ile Gly Ala Thr Leu Ile His Met<br>1               5                   10                  15 | 48 |
| ttg tta cct aac ata tct ttt cca gaa act att aac aat aac act gat<br>Leu Leu Pro Asn Ile Ser Phe Pro Glu Thr Ile Asn Asn Asn Thr Asp<br>            20                  25                  30 | 96 |
| aaa ctt tct ggg tta tat ata agt ggg caa tat aaa cca ggg att tct<br>Lys Leu Ser Gly Leu Tyr Ile Ser Gly Gln Tyr Lys Pro Gly Ile Ser<br>        35                  40                  45 | 144 |
| cat ttc agc aaa ttt tca gtc aaa gaa atc tat aat gat aac att caa<br>His Phe Ser Lys Phe Ser Val Lys Glu Ile Tyr Asn Asp Asn Ile Gln<br>    50                  55                  60 | 192 |
| cta att ggg tta aga cac aac gca att tct act agt acc ctt aat att<br>Leu Ile Gly Leu Arg His Asn Ala Ile Ser Thr Ser Thr Leu Asn Ile<br>65                  70                  75                  80 | 240 |
| aat aca gat ttt aat atc ccc tat aaa gta aca ttt caa aat aac att<br>Asn Thr Asp Phe Asn Ile Pro Tyr Lys Val Thr Phe Gln Asn Asn Ile<br>                85                  90                  95 | 288 |
| acc agc ttt agt gga gct att ggt tat tct gat ccc aca ggg gca aga<br>Thr Ser Phe Ser Gly Ala Ile Gly Tyr Ser Asp Pro Thr Gly Ala Arg<br>            100                 105                 110 | 336 |
| ttt gag ctt gaa ggt tct tat gaa gaa ttt gat gtg aca gat cct gga<br>Phe Glu Leu Glu Gly Ser Tyr Glu Glu Phe Asp Val Thr Asp Pro Gly<br>        115                 120                 125 | 384 |
| gac tgc tta ata aaa gat acc tat aga tat ttc gct tta gct aga aac<br>Asp Cys Leu Ile Lys Asp Thr Tyr Arg Tyr Phe Ala Leu Ala Arg Asn<br>    130                 135                 140 | 432 |
| cca tca ggt tct agc cct acc tca aac aac tat act gtt atg aga aat<br>Pro Ser Gly Ser Ser Pro Thr Ser Asn Asn Tyr Thr Val Met Arg Asn<br>145                 150                 155                 160 | 480 |
| gat ggt gtt tcc att act tct gtt ata ttt aat ggc tgt tat gac atc<br>Asp Gly Val Ser Ile Thr Ser Val Ile Phe Asn Gly Cys Tyr Asp Ile<br>                165                 170                 175 | 528 |
| ttt tta aag gat tta gaa gta tca cct tat gta tgt gtt ggt gta ggt<br>Phe Leu Lys Asp Leu Glu Val Ser Pro Tyr Val Cys Val Gly Val Gly<br>            180                 185                 190 | 576 |
| gga gat ttt ata gaa ttt ttt gac gca tta cac att aaa tta gca tac<br>            | 624 |

```
Gly Asp Phe Ile Glu Phe Phe Asp Ala Leu His Ile Lys Leu Ala Tyr
        195                 200                 205 caa ggc aag tta ggt atc aat tat cac tta tcg act caa gca agc gta    672
Gln Gly Lys Leu Gly Ile Asn Tyr His Leu Ser Thr Gln Ala Ser Val
    210                 215                 220 ttt att gat gga tat tat cat aag gtt ata gga aat caa ttc aac aat    720
Phe Ile Asp Gly Tyr Tyr His Lys Val Ile Gly Asn Gln Phe Asn Asn
225                 230                 235                 240 cta aat gtt caa cac gtg gct agt aca gat ttt gga cct gta tac gca    768
Leu Asn Val Gln His Val Ala Ser Thr Asp Phe Gly Pro Val Tyr Ala
                245                 250                 255 gta gcc aca ctt aac att ggt tat ttt ggt ggt gaa atc gga att aga    816
Val Ala Thr Leu Asn Ile Gly Tyr Phe Gly Gly Glu Ile Gly Ile Arg
            260                 265                 270 ctt aca ttt taa                                                    828
Leu Thr Phe
        275

<210> SEQ ID NO 28
<211> LENGTH: 275
<212> TYPE: PRT
<213> ORGANISM: Ehrlichia chaffeensis

<400> SEQUENCE: 28

Met Ser Lys Lys Asn Phe Ile Thr Ile Gly Ala Thr Leu Ile His Met
1               5                   10                  15

Leu Leu Pro Asn Ile Ser Phe Pro Glu Thr Ile Asn Asn Asn Thr Asp
            20                  25                  30

Lys Leu Ser Gly Leu Tyr Ile Ser Gly Gln Tyr Lys Pro Gly Ile Ser
        35                  40                  45

His Phe Ser Lys Phe Ser Val Lys Glu Ile Tyr Asn Asp Asn Ile Gln
    50                  55                  60

Leu Ile Gly Leu Arg His Asn Ala Ile Ser Thr Ser Thr Leu Asn Ile
65                  70                  75                  80

Asn Thr Asp Phe Asn Ile Pro Tyr Lys Val Thr Phe Gln Asn Asn Ile
                85                  90                  95

Thr Ser Phe Ser Gly Ala Ile Gly Tyr Ser Asp Pro Thr Gly Ala Arg
            100                 105                 110

Phe Glu Leu Glu Gly Ser Tyr Glu Glu Phe Asp Val Thr Asp Pro Gly
        115                 120                 125

Asp Cys Leu Ile Lys Asp Thr Tyr Arg Tyr Phe Ala Leu Ala Arg Asn
130                 135                 140

Pro Ser Gly Ser Ser Pro Thr Ser Asn Asn Tyr Thr Val Met Arg Asn
145                 150                 155                 160

Asp Gly Val Ser Ile Thr Ser Val Ile Phe Asn Gly Cys Tyr Asp Ile
                165                 170                 175

Phe Leu Lys Asp Leu Glu Val Ser Pro Tyr Val Cys Val Gly Val Gly
            180                 185                 190

Gly Asp Phe Ile Glu Phe Phe Asp Ala Leu His Ile Lys Leu Ala Tyr
        195                 200                 205

Gln Gly Lys Leu Gly Ile Asn Tyr His Leu Ser Thr Gln Ala Ser Val
    210                 215                 220

Phe Ile Asp Gly Tyr Tyr His Lys Val Ile Gly Asn Gln Phe Asn Asn
225                 230                 235                 240

Leu Asn Val Gln His Val Ala Ser Thr Asp Phe Gly Pro Val Tyr Ala
                245                 250                 255
```

```
            Val Ala Thr Leu Asn Ile Gly Tyr Phe Gly Gly Glu Ile Gly Ile Arg
                            260                 265                 270

Leu Thr Phe
                275

<210> SEQ ID NO 29
<211> LENGTH: 858
<212> TYPE: DNA
<213> ORGANISM: Ehrlichia chaffeensis
<220> FEATURE:
<221> NAME/KEY: CDS
<222> LOCATION: (1)..(858)

<400> SEQUENCE: 29 atg aat aat aga aaa agt ttt ttt ata ata ggt gca tca tta cta gca       48
Met Asn Asn Arg Lys Ser Phe Phe Ile Ile Gly Ala Ser Leu Leu Ala
  1               5                  10                  15 agc tta tta ttc aca tct gag gcc tct tct aca gga aat gta agt aac       96
Ser Leu Leu Phe Thr Ser Glu Ala Ser Ser Thr Gly Asn Val Ser Asn
             20                  25                  30 cat act tat ttt aaa cct agg tta tat atc agt gga caa tat aga cca      144
His Thr Tyr Phe Lys Pro Arg Leu Tyr Ile Ser Gly Gln Tyr Arg Pro
         35                  40                  45 gga gtt tct cat ttt agc aaa ttt tca gtc aaa gaa acc aac tac aat      192
Gly Val Ser His Phe Ser Lys Phe Ser Val Lys Glu Thr Asn Tyr Asn
     50                  55                  60 act act caa cta gtt ggg ctt aaa aag gac atc agt gtc ata ggg aac      240
Thr Thr Gln Leu Val Gly Leu Lys Lys Asp Ile Ser Val Ile Gly Asn
 65                  70                  75                  80 agt aat atc aca acc tac aca aat ttc aac ttt cct tac att gca gaa      288
Ser Asn Ile Thr Thr Tyr Thr Asn Phe Asn Phe Pro Tyr Ile Ala Glu
                 85                  90                  95 ttt caa gac aat gcc ata agt ttc agt ggg gca att gga tac ttg tat      336
Phe Gln Asp Asn Ala Ile Ser Phe Ser Gly Ala Ile Gly Tyr Leu Tyr
            100                 105                 110 tcc gag aat ttt aga att gaa gta gag gct tct tat gaa gaa ttt gat      384
Ser Glu Asn Phe Arg Ile Glu Val Glu Ala Ser Tyr Glu Glu Phe Asp
        115                 120                 125 gtt aaa aat cca gaa gga tct gct aca gac gca tac agg tat ttt gca      432
Val Lys Asn Pro Glu Gly Ser Ala Thr Asp Ala Tyr Arg Tyr Phe Ala
    130                 135                 140 cta gca cgt gct atg gat ggc act aat aaa tct agt cct gat gac aca      480
Leu Ala Arg Ala Met Asp Gly Thr Asn Lys Ser Ser Pro Asp Asp Thr
145                 150                 155                 160 aga aaa ttc act gtc atg aga aat gac ggg tta tca att tca tca gta      528
Arg Lys Phe Thr Val Met Arg Asn Asp Gly Leu Ser Ile Ser Ser Val
                165                 170                 175 atg ata aat ggg tgt tac aat ttt aca tta gat gat ata cca gta gta      576
Met Ile Asn Gly Cys Tyr Asn Phe Thr Leu Asp Asp Ile Pro Val Val
            180                 185                 190 ccg tat gta tgc gca gga ata gga gga gat ttc ata gag ttt ttt aat      624
Pro Tyr Val Cys Ala Gly Ile Gly Gly Asp Phe Ile Glu Phe Phe Asn
        195                 200                 205 gat tta cat gtt aag ttt cgt cat caa ggc aag gta ggt att agt tat      672
Asp Leu His Val Lys Phe Arg His Gln Gly Lys Val Gly Ile Ser Tyr
    210                 215                 220 tct ata tcc cct gaa gta agt tta ttt ctt aac gga tat tac cat aaa      720
Ser Ile Ser Pro Glu Val Ser Leu Phe Leu Asn Gly Tyr Tyr His Lys
225                 230                 235                 240 gta aca ggt aac aga ttt aaa aac tta cac gtt caa cac gta agt gat      768
Val Thr Gly Asn Arg Phe Lys Asn Leu His Val Gln His Val Ser Asp
```

-continued

```
                                 245                 250                 255
tta agt gac gct cct aag ttc aca tct gca gtt gct aca ctc aat gtt         816
Leu Ser Asp Ala Pro Lys Phe Thr Ser Ala Val Ala Thr Leu Asn Val
            260                 265                 270 ggg tac ttt ggt ggc gaa att gga gta aga ttt ata ttt taa                 858
Gly Tyr Phe Gly Gly Glu Ile Gly Val Arg Phe Ile Phe
        275                 280                 285
```

<210> SEQ ID NO 30
<211> LENGTH: 285
<212> TYPE: PRT
<213> ORGANISM: Ehrlichia chaffeensis

<400> SEQUENCE: 30

Met Asn Asn Arg Lys Ser Phe Phe Ile Ile Gly Ala Ser Leu Leu Ala
 1               5                  10                  15

Ser Leu Leu Phe Thr Ser Glu Ala Ser Ser Thr Gly Asn Val Ser Asn
             20                  25                  30

His Thr Tyr Phe Lys Pro Arg Leu Tyr Ile Ser Gly Gln Tyr Arg Pro
         35                  40                  45

Gly Val Ser His Phe Ser Lys Phe Ser Val Lys Glu Thr Asn Tyr Asn
     50                  55                  60

Thr Thr Gln Leu Val Gly Leu Lys Lys Asp Ile Ser Val Ile Gly Asn
 65                  70                  75                  80

Ser Asn Ile Thr Thr Tyr Thr Asn Phe Asn Phe Pro Tyr Ile Ala Glu
                 85                  90                  95

Phe Gln Asp Asn Ala Ile Ser Phe Ser Gly Ala Ile Gly Tyr Leu Tyr
            100                 105                 110

Ser Glu Asn Phe Arg Ile Glu Val Glu Ala Ser Tyr Glu Glu Phe Asp
        115                 120                 125

Val Lys Asn Pro Glu Gly Ser Ala Thr Asp Ala Tyr Arg Tyr Phe Ala
    130                 135                 140

Leu Ala Arg Ala Met Asp Gly Thr Asn Lys Ser Ser Pro Asp Asp Thr
145                 150                 155                 160

Arg Lys Phe Thr Val Met Arg Asn Asp Gly Leu Ser Ile Ser Ser Val
                165                 170                 175

Met Ile Asn Gly Cys Tyr Asn Phe Thr Leu Asp Asp Ile Pro Val Val
            180                 185                 190

Pro Tyr Val Cys Ala Gly Ile Gly Gly Asp Phe Ile Glu Phe Phe Asn
        195                 200                 205

Asp Leu His Val Lys Phe Arg His Gln Gly Lys Val Gly Ile Ser Tyr
    210                 215                 220

Ser Ile Ser Pro Glu Val Ser Leu Phe Leu Asn Gly Tyr Tyr His Lys
225                 230                 235                 240

Val Thr Gly Asn Arg Phe Lys Asn Leu His Val Gln His Val Ser Asp
                245                 250                 255

Leu Ser Asp Ala Pro Lys Phe Thr Ser Ala Val Ala Thr Leu Asn Val
            260                 265                 270

Gly Tyr Phe Gly Gly Glu Ile Gly Val Arg Phe Ile Phe
        275                 280                 285

<210> SEQ ID NO 31
<211> LENGTH: 867
<212> TYPE: DNA
<213> ORGANISM: Ehrlichia canis
<220> FEATURE:
<221> NAME/KEY: CDS

<222> LOCATION: (1)..(867)

<400> SEQUENCE: 31

| | | |
|---|---|---:|
| atg aat tgc aaa aga ttt ttc ata gca agt gca ttg ata tca cta atg<br>Met Asn Cys Lys Arg Phe Phe Ile Ala Ser Ala Leu Ile Ser Leu Met<br>1               5                    10                 15 | | 48 |
| tct ttc tta cct agc gta tct ttt tct gaa tca ata cat gaa gat aat<br>Ser Phe Leu Pro Ser Val Ser Phe Ser Glu Ser Ile His Glu Asp Asn<br>                   20                    25                    30 | | 96 |
| ata aat ggt aac ttt tac att agt gca aag tat atg cca agt gcc tca<br>Ile Asn Gly Asn Phe Tyr Ile Ser Ala Lys Tyr Met Pro Ser Ala Ser<br>             35                    40                    45 | | 144 |
| cac ttt ggc gta ttt tca gtt aaa gaa gag aaa aac aca aca act gga<br>His Phe Gly Val Phe Ser Val Lys Glu Glu Lys Asn Thr Thr Thr Gly<br>50                    55                    60 | | 192 |
| gtt ttc gga tta aaa caa gat tgg gac gga gca aca ata aag gat gca<br>Val Phe Gly Leu Lys Gln Asp Trp Asp Gly Ala Thr Ile Lys Asp Ala<br>65                   70                    75                    80 | | 240 |
| agc agc agc cac aca ata gac cca agt aca ata ttc tcc att tca aat<br>Ser Ser Ser His Thr Ile Asp Pro Ser Thr Ile Phe Ser Ile Ser Asn<br>                   85                    90                    95 | | 288 |
| tat tca ttt aaa tat gaa aac aat cca ttt tta ggg ttt gca gga gct<br>Tyr Ser Phe Lys Tyr Glu Asn Asn Pro Phe Leu Gly Phe Ala Gly Ala<br>             100                  105               110 | | 336 |
| att ggc tac tca atg ggt ggt cca agg gta gag ttt gaa gtg tct tac<br>Ile Gly Tyr Ser Met Gly Gly Pro Arg Val Glu Phe Glu Val Ser Tyr<br>             115                  120               125 | | 384 |
| gaa ata ttt gat gta aaa aac caa ggt aac agt tac aag aac gat gct<br>Glu Ile Phe Asp Val Lys Asn Gln Gly Asn Ser Tyr Lys Asn Asp Ala<br>130                    135                  140 | | 432 |
| cac aaa tat tgc gct tta tca aga cac acc gga ggt atg cca caa gcc<br>His Lys Tyr Cys Ala Leu Ser Arg His Thr Gly Gly Met Pro Gln Ala<br>145                    150                  155                    160 | | 480 |
| ggt cat caa aat aaa ttt gtc ttc cta aaa aat gaa gga tta ctt gac<br>Gly His Gln Asn Lys Phe Val Phe Leu Lys Asn Glu Gly Leu Leu Asp<br>             165                  170               175 | | 528 |
| ata tca ctt atg ata aac gca tgt tat gat ata aca atc gac agc atg<br>Ile Ser Leu Met Ile Asn Ala Cys Tyr Asp Ile Thr Ile Asp Ser Met<br>180                    185                  190 | | 576 |
| cca ttt tct cca tat ata tgt gca ggt att ggt agt gac tta gtt tcg<br>Pro Phe Ser Pro Tyr Ile Cys Ala Gly Ile Gly Ser Asp Leu Val Ser<br>             195                  200               205 | | 624 |
| atg ttt gaa act aca aat cct aaa att tct tat caa gga aaa tta ggt<br>Met Phe Glu Thr Thr Asn Pro Lys Ile Ser Tyr Gln Gly Lys Leu Gly<br>210                    215                  220 | | 672 |
| gta agt tac tcc ata agc cca gaa gca tct gtt ttt gtt gga gga cac<br>Val Ser Tyr Ser Ile Ser Pro Glu Ala Ser Val Phe Val Gly Gly His<br>225                    230                  235                    240 | | 720 |
| ttt cac aga gtt ata ggt aat gaa ttt aaa gac att cct gca ata act<br>Phe His Arg Val Ile Gly Asn Glu Phe Lys Asp Ile Pro Ala Ile Thr<br>             245                  250               255 | | 768 |
| cct gct gga gca aca gaa att aaa ggc aca cag ttt aca aca gta aca<br>Pro Ala Gly Ala Thr Glu Ile Lys Gly Thr Gln Phe Thr Thr Val Thr<br>260                    265                  270 | | 816 |
| tta aac ata tgc cac ttc gga cta gag ctt gga ggc agg ttt act ttt<br>Leu Asn Ile Cys His Phe Gly Leu Glu Leu Gly Gly Arg Phe Thr Phe<br>             275                  280               285 | | 864 |
| taa | | 867 |

<210> SEQ ID NO 32
<211> LENGTH: 288
<212> TYPE: PRT
<213> ORGANISM: Ehrlichia canis

<400> SEQUENCE: 32

```
Met Asn Cys Lys Arg Phe Phe Ile Ala Ser Ala Leu Ile Ser Leu Met
  1               5                  10                  15

Ser Phe Leu Pro Ser Val Ser Phe Ser Glu Ser Ile His Glu Asp Asn
             20                  25                  30

Ile Asn Gly Asn Phe Tyr Ile Ser Ala Lys Tyr Met Pro Ser Ala Ser
         35                  40                  45

His Phe Gly Val Phe Ser Val Lys Glu Glu Lys Asn Thr Thr Thr Gly
     50                  55                  60

Val Phe Gly Leu Lys Gln Asp Trp Asp Gly Ala Thr Ile Lys Asp Ala
 65                  70                  75                  80

Ser Ser Ser His Thr Ile Asp Pro Ser Thr Ile Phe Ser Ile Ser Asn
                 85                  90                  95

Tyr Ser Phe Lys Tyr Glu Asn Asn Pro Phe Leu Gly Phe Ala Gly Ala
            100                 105                 110

Ile Gly Tyr Ser Met Gly Gly Pro Arg Val Glu Phe Glu Val Ser Tyr
        115                 120                 125

Glu Ile Phe Asp Val Lys Asn Gln Gly Asn Ser Tyr Lys Asn Asp Ala
    130                 135                 140

His Lys Tyr Cys Ala Leu Ser Arg His Thr Gly Gly Met Pro Gln Ala
145                 150                 155                 160

Gly His Gln Asn Lys Phe Val Phe Leu Lys Asn Glu Gly Leu Leu Asp
                165                 170                 175

Ile Ser Leu Met Ile Asn Ala Cys Tyr Asp Ile Thr Ile Asp Ser Met
            180                 185                 190

Pro Phe Ser Pro Tyr Ile Cys Ala Gly Ile Gly Ser Asp Leu Val Ser
        195                 200                 205

Met Phe Glu Thr Thr Asn Pro Lys Ile Ser Tyr Gln Gly Lys Leu Gly
    210                 215                 220

Val Ser Tyr Ser Ile Ser Pro Glu Ala Ser Val Phe Val Gly Gly His
225                 230                 235                 240

Phe His Arg Val Ile Gly Asn Glu Phe Lys Asp Ile Pro Ala Ile Thr
                245                 250                 255

Pro Ala Gly Ala Thr Glu Ile Lys Gly Thr Gln Phe Thr Thr Val Thr
            260                 265                 270

Leu Asn Ile Cys His Phe Gly Leu Glu Leu Gly Gly Arg Phe Thr Phe
        275                 280                 285
```

<210> SEQ ID NO 33
<211> LENGTH: 864
<212> TYPE: DNA
<213> ORGANISM: Ehrlichia chaffeensis
<220> FEATURE:
<221> NAME/KEY: CDS
<222> LOCATION: (1)..(864)

<400> SEQUENCE: 33

```
atg aaa tat aaa aaa act ttt aca gta act gca tta gta tta tta act      48
Met Lys Tyr Lys Lys Thr Phe Thr Val Thr Ala Leu Val Leu Leu Thr
  1               5                  10                  15 tcc ttt aca cat ttt ata cct ttt tat agt cca gca cgt gcc agt aca      96
Ser Phe Thr His Phe Ile Pro Phe Tyr Ser Pro Ala Arg Ala Ser Thr
             20                  25                  30
```

```
att cac aac ttc tac att agt gga aaa tat atg cca aca gcg tca cat      144
Ile His Asn Phe Tyr Ile Ser Gly Lys Tyr Met Pro Thr Ala Ser His
        35                  40                  45 ttt gga att ttt tca gct aaa gaa gaa caa agt ttt act aag gta tta      192
Phe Gly Ile Phe Ser Ala Lys Glu Glu Gln Ser Phe Thr Lys Val Leu
 50                  55                  60 gtt ggg tta gat caa cga tta tca cat aat att ata aac aat aat gat      240
Val Gly Leu Asp Gln Arg Leu Ser His Asn Ile Ile Asn Asn Asn Asp
 65                  70                  75                  80 aca gca aag agt ctt aag gtt caa aat tat tca ttt aaa tac aaa aat      288
Thr Ala Lys Ser Leu Lys Val Gln Asn Tyr Ser Phe Lys Tyr Lys Asn
                 85                  90                  95 aac cca ttt cta gga ttt gca aga gct att ggt tat tca ata ggc aat      336
Asn Pro Phe Leu Gly Phe Ala Arg Ala Ile Gly Tyr Ser Ile Gly Asn
            100                 105                 110 tca aga ata gaa cta gaa gta tca cat gaa ata ttt gat act aaa aac      384
Ser Arg Ile Glu Leu Glu Val Ser His Glu Ile Phe Asp Thr Lys Asn
        115                 120                 125 cca gga aac aat tat tta aat gac tct cac aaa tat tgc gct tta tct      432
Pro Gly Asn Asn Tyr Leu Asn Asp Ser His Lys Tyr Cys Ala Leu Ser
130                 135                 140 cat gga agt cac ata tgc agt gat gga aat agc gga gat tgg tac act      480
His Gly Ser His Ile Cys Ser Asp Gly Asn Ser Gly Asp Trp Tyr Thr
145                 150                 155                 160 gca aaa act gat aag ttt gta ctt ctg aaa aat gaa ggt tta ctt gac      528
Ala Lys Thr Asp Lys Phe Val Leu Leu Lys Asn Glu Gly Leu Leu Asp
                165                 170                 175 gtc tca ttt atg tta aac gca tgt tat gac ata aca act gaa aaa atg      576
Val Ser Phe Met Leu Asn Ala Cys Tyr Asp Ile Thr Thr Glu Lys Met
            180                 185                 190 cct ttt tca cct tat ata tgt gca ggt att ggt act gat ctc ata tct      624
Pro Phe Ser Pro Tyr Ile Cys Ala Gly Ile Gly Thr Asp Leu Ile Ser
        195                 200                 205 atg ttt gag aca aca caa aac aaa ata tct tat caa gga aag tta ggt      672
Met Phe Glu Thr Thr Gln Asn Lys Ile Ser Tyr Gln Gly Lys Leu Gly
210                 215                 220 tta aac tat act ata aac tca aga gtt tct gtt ttt gca ggt ggg cac      720
Leu Asn Tyr Thr Ile Asn Ser Arg Val Ser Val Phe Ala Gly Gly His
225                 230                 235                 240 ttt cat aaa gta ata ggt aat gaa ttt aaa ggt att cct act cta tta      768
Phe His Lys Val Ile Gly Asn Glu Phe Lys Gly Ile Pro Thr Leu Leu
                245                 250                 255 cct gat gga tca aac att aaa gta caa cag tct gca aca gta aca tta      816
Pro Asp Gly Ser Asn Ile Lys Val Gln Gln Ser Ala Thr Val Thr Leu
            260                 265                 270 gat gtg tgc cat ttc ggg tta gag att gga agt aga ttt ttc ttt taa      864
Asp Val Cys His Phe Gly Leu Glu Ile Gly Ser Arg Phe Phe Phe
        275                 280                 285

<210> SEQ ID NO 34
<211> LENGTH: 287
<212> TYPE: PRT
<213> ORGANISM: Ehrlichia chaffeensis

<400> SEQUENCE: 34

Met Lys Tyr Lys Lys Thr Phe Thr Val Thr Ala Leu Val Leu Leu Thr
 1               5                  10                  15

Ser Phe Thr His Phe Ile Pro Phe Tyr Ser Pro Ala Arg Ala Ser Thr
             20                  25                  30
```

```
Ile His Asn Phe Tyr Ile Ser Gly Lys Tyr Met Pro Thr Ala Ser His
        35                  40                  45

Phe Gly Ile Phe Ser Ala Lys Glu Glu Gln Ser Phe Thr Lys Val Leu
    50                  55                  60

Val Gly Leu Asp Gln Arg Leu Ser His Asn Ile Ile Asn Asn Asn Asp
 65                  70                  75                  80

Thr Ala Lys Ser Leu Lys Val Gln Asn Tyr Ser Phe Lys Tyr Lys Asn
                 85                  90                  95

Asn Pro Phe Leu Gly Phe Ala Arg Ala Ile Gly Tyr Ser Ile Gly Asn
            100                 105                 110

Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175

Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285

<210> SEQ ID NO 35
<211> LENGTH: 924
<212> TYPE: DNA
<213> ORGANISM: Ehrlichia canis
<220> FEATURE:
<221> NAME/KEY: CDS
<222> LOCATION: (1)..(924)

<400> SEQUENCE: 35 atg ttt tat act aat ata tat att ctg gct tgt att tac ttt gca ctt      48
Met Phe Tyr Thr Asn Ile Tyr Ile Leu Ala Cys Ile Tyr Phe Ala Leu
 1               5                  10                  15 cca cta ttg tta att tat ttt cac tat ttt agg tgt aat atg aat tgc      96
Pro Leu Leu Leu Ile Tyr Phe His Tyr Phe Arg Cys Asn Met Asn Cys
             20                  25                  30 aaa aaa att ctt ata aca act gca tta ata tca tta atg tac tct att     144
Lys Lys Ile Leu Ile Thr Thr Ala Leu Ile Ser Leu Met Tyr Ser Ile
         35                  40                  45 cca agc ata tct ttt tct gat act ata caa gat ggt aac atg ggt ggt     192
Pro Ser Ile Ser Phe Ser Asp Thr Ile Gln Asp Gly Asn Met Gly Gly
     50                  55                  60 aac ttc tat att agt gga aag tat gta cca agt gtc tca cat ttt ggt     240
Asn Phe Tyr Ile Ser Gly Lys Tyr Val Pro Ser Val Ser His Phe Gly
 65                  70                  75                  80
```

```
agc ttc tca gct aaa gaa gaa agc aaa tca act gtt gga gtt ttt gga    288
Ser Phe Ser Ala Lys Glu Glu Ser Lys Ser Thr Val Gly Val Phe Gly
             85                  90                  95 tta aaa cat gat tgg gat gga agt cca ata ctt aag aat aaa cac gct    336
Leu Lys His Asp Trp Asp Gly Ser Pro Ile Leu Lys Asn Lys His Ala
            100                 105                 110 gac ttt act gtt cca aac tat tcg ttc aga tac gag aac aat cca ttt    384
Asp Phe Thr Val Pro Asn Tyr Ser Phe Arg Tyr Glu Asn Asn Pro Phe
        115                 120                 125 cta ggg ttt gca gga gct atc ggt tac tca atg ggt ggc cca aga ata    432
Leu Gly Phe Ala Gly Ala Ile Gly Tyr Ser Met Gly Gly Pro Arg Ile
    130                 135                 140 gaa ttc gaa ata tct tat gaa gca ttc gac gta aaa agt cct aat atc    480
Glu Phe Glu Ile Ser Tyr Glu Ala Phe Asp Val Lys Ser Pro Asn Ile
145                 150                 155                 160 aat tat caa aat gac gcg cac agg tac tgc gct cta tct cat cac aca    528
Asn Tyr Gln Asn Asp Ala His Arg Tyr Cys Ala Leu Ser His His Thr
                165                 170                 175 tcg gca gcc atg gaa gct gat aaa ttt gtc ttc tta aaa aac gaa ggg    576
Ser Ala Ala Met Glu Ala Asp Lys Phe Val Phe Leu Lys Asn Glu Gly
            180                 185                 190 tta att gac ata tca ctt gca ata aat gca tgt tat gat ata ata aat    624
Leu Ile Asp Ile Ser Leu Ala Ile Asn Ala Cys Tyr Asp Ile Ile Asn
        195                 200                 205 gac aaa gta cct gtt tct cct tat ata tgc gca ggt att ggt act gat    672
Asp Lys Val Pro Val Ser Pro Tyr Ile Cys Ala Gly Ile Gly Thr Asp
    210                 215                 220 ttg att tct atg ttt gaa gct aca agt cct aaa att tcc tac caa gga    720
Leu Ile Ser Met Phe Glu Ala Thr Ser Pro Lys Ile Ser Tyr Gln Gly
225                 230                 235                 240 aaa ctg ggc att agt tac tct att aat ccg gaa acc tct gtt ttc atc    768
Lys Leu Gly Ile Ser Tyr Ser Ile Asn Pro Glu Thr Ser Val Phe Ile
                245                 250                 255 ggt ggg cat ttc cac agg atc ata ggt aat gag ttt aga gat att cct    816
Gly Gly His Phe His Arg Ile Ile Gly Asn Glu Phe Arg Asp Ile Pro
            260                 265                 270 gca ata gta cct agt aac tca act aca ata agt gga cca caa ttt gca    864
Ala Ile Val Pro Ser Asn Ser Thr Thr Ile Ser Gly Pro Gln Phe Ala
        275                 280                 285 aca gta aca cta aat gtg tgt cac ttt ggt tta gaa ctt gga gga aga    912
Thr Val Thr Leu Asn Val Cys His Phe Gly Leu Glu Leu Gly Gly Arg
    290                 295                 300 ttt aac ttc taa                                                    924
Phe Asn Phe
305

<210> SEQ ID NO 36
<211> LENGTH: 307
<212> TYPE: PRT
<213> ORGANISM: Ehrlichia canis

<400> SEQUENCE: 36

Met Phe Tyr Thr Asn Ile Tyr Ile Leu Ala Cys Ile Tyr Phe Ala Leu
1               5                   10                  15

Pro Leu Leu Leu Ile Tyr Phe His Tyr Phe Arg Cys Asn Met Asn Cys
            20                  25                  30

Lys Lys Ile Leu Ile Thr Thr Ala Leu Ile Ser Leu Met Tyr Ser Ile
        35                  40                  45

Pro Ser Ile Ser Phe Ser Asp Thr Ile Gln Asp Gly Asn Met Gly Gly
    50                  55                  60
```

-continued

```
Asn Phe Tyr Ile Ser Gly Lys Tyr Val Pro Ser Val Ser His Phe Gly
 65                  70                  75                  80

Ser Phe Ser Ala Lys Glu Ser Lys Ser Thr Val Gly Val Phe Gly
                 85                  90                  95

Leu Lys His Asp Trp Asp Gly Ser Pro Ile Leu Lys Asn Lys His Ala
                100                 105                 110

Asp Phe Thr Val Pro Asn Tyr Ser Phe Arg Tyr Glu Asn Asn Pro Phe
                115                 120                 125

Leu Gly Phe Ala Gly Ala Ile Gly Tyr Ser Met Gly Gly Pro Arg Ile
            130                 135                 140

Glu Phe Glu Ile Ser Tyr Glu Ala Phe Asp Val Lys Ser Pro Asn Ile
145                 150                 155                 160

Asn Tyr Gln Asn Asp Ala His Arg Tyr Cys Ala Leu Ser His His Thr
                165                 170                 175

Ser Ala Ala Met Glu Ala Asp Lys Phe Val Phe Leu Lys Asn Glu Gly
                180                 185                 190

Leu Ile Asp Ile Ser Leu Ala Ile Asn Ala Cys Tyr Asp Ile Ile Asn
            195                 200                 205

Asp Lys Val Pro Val Ser Pro Tyr Ile Cys Ala Gly Ile Gly Thr Asp
210                 215                 220

Leu Ile Ser Met Phe Glu Ala Thr Ser Pro Lys Ile Ser Tyr Gln Gly
225                 230                 235                 240

Lys Leu Gly Ile Ser Tyr Ser Ile Asn Pro Glu Thr Ser Val Phe Ile
                245                 250                 255

Gly Gly His Phe His Arg Ile Ile Gly Asn Glu Phe Arg Asp Ile Pro
            260                 265                 270

Ala Ile Val Pro Ser Asn Ser Thr Thr Ile Ser Gly Pro Gln Phe Ala
                275                 280                 285

Thr Val Thr Leu Asn Val Cys His Phe Gly Leu Glu Leu Gly Gly Arg
            290                 295                 300

Phe Asn Phe
305
```

<210> SEQ ID NO 37
<211> LENGTH: 843
<212> TYPE: DNA
<213> ORGANISM: Ehrlichia canis
<220> FEATURE:
<221> NAME/KEY: CDS
<222> LOCATION: (1)..(843)

<400> SEQUENCE: 37

```
atg aat tgc aaa aaa att ctt ata aca act gca tta atg tca tta atg      48
Met Asn Cys Lys Lys Ile Leu Ile Thr Thr Ala Leu Met Ser Leu Met
 1               5                  10                  15 tac tat gct cca agc ata tct ttt tct gat act ata caa gac gat aac      96
Tyr Tyr Ala Pro Ser Ile Ser Phe Ser Asp Thr Ile Gln Asp Asp Asn
             20                  25                  30 act ggt agc ttc tac atc agt gga aaa tat gta cca agt gtt tca cat     144
Thr Gly Ser Phe Tyr Ile Ser Gly Lys Tyr Val Pro Ser Val Ser His
         35                  40                  45 ttt ggt gtt ttc tca gct aaa gaa gaa aga aac tca act gtt gga gtt     192
Phe Gly Val Phe Ser Ala Lys Glu Glu Arg Asn Ser Thr Val Gly Val
     50                  55                  60 ttt gga tta aaa cat gat tgg aat gga ggt aca ata tct aac tct tct     240
Phe Gly Leu Lys His Asp Trp Asn Gly Gly Thr Ile Ser Asn Ser Ser
 65                  70                  75                  80
```

```
cca gaa aat ata ttc aca gtt caa aat tat tcg ttt aaa tac gaa aac    288
Pro Glu Asn Ile Phe Thr Val Gln Asn Tyr Ser Phe Lys Tyr Glu Asn
                85                  90                  95 aac cca ttc tta ggg ttt gca gga gct att ggt tat tca atg ggt ggc    336
Asn Pro Phe Leu Gly Phe Ala Gly Ala Ile Gly Tyr Ser Met Gly Gly
            100                 105                 110 cca aga ata gaa ctt gaa gtt ctg tac gag aca ttc gat gtg aaa aat    384
Pro Arg Ile Glu Leu Glu Val Leu Tyr Glu Thr Phe Asp Val Lys Asn
        115                 120                 125 cag aac aat aat tat aag aac ggc gca cac aga tac tgt gct tta tct    432
Gln Asn Asn Asn Tyr Lys Asn Gly Ala His Arg Tyr Cys Ala Leu Ser
    130                 135                 140 cat cat agt tca gca aca aac atg tcc tcc gca agt aac aaa ttt gtt    480
His His Ser Ser Ala Thr Asn Met Ser Ser Ala Ser Asn Lys Phe Val
145                 150                 155                 160 ttc tta aaa aat gaa ggg tta att gac tta tca ttt atg ata aat gca    528
Phe Leu Lys Asn Glu Gly Leu Ile Asp Leu Ser Phe Met Ile Asn Ala
                165                 170                 175 tgc tat gac ata ata att gaa gga atg cct ttt tca cct tat att tgt    576
Cys Tyr Asp Ile Ile Ile Glu Gly Met Pro Phe Ser Pro Tyr Ile Cys
            180                 185                 190 gca ggt gtt ggt act gat gtt gtt tcc atg ttt gaa gct ata aat cct    624
Ala Gly Val Gly Thr Asp Val Val Ser Met Phe Glu Ala Ile Asn Pro
        195                 200                 205 aaa att tct tac caa gga aaa cta gga tta ggt tat agt ata agt tca    672
Lys Ile Ser Tyr Gln Gly Lys Leu Gly Leu Gly Tyr Ser Ile Ser Ser
    210                 215                 220 gaa gcc tct gtt ttt atc ggt gga cac ttt cac aga gtc ata ggt aat    720
Glu Ala Ser Val Phe Ile Gly Gly His Phe His Arg Val Ile Gly Asn
225                 230                 235                 240 gaa ttt aga gac atc cct gct atg gtt cct agt gga tca aat ctt cca    768
Glu Phe Arg Asp Ile Pro Ala Met Val Pro Ser Gly Ser Asn Leu Pro
                245                 250                 255 gaa aac caa ttt gca ata gta aca cta aat gtg tgt cac ttt ggt tta    816
Glu Asn Gln Phe Ala Ile Val Thr Leu Asn Val Cys His Phe Gly Leu
            260                 265                 270 gaa ctt gga gga aga ttt aac ttc tga                                843
Glu Leu Gly Gly Arg Phe Asn Phe
        275                 280

<210> SEQ ID NO 38
<211> LENGTH: 280
<212> TYPE: PRT
<213> ORGANISM: Ehrlichia canis

<400> SEQUENCE: 38

Met Asn Cys Lys Lys Ile Leu Ile Thr Thr Ala Leu Met Ser Leu Met
 1               5                  10                  15

Tyr Tyr Ala Pro Ser Ile Ser Phe Ser Asp Thr Ile Gln Asp Asp Asn
            20                  25                  30

Thr Gly Ser Phe Tyr Ile Ser Gly Lys Tyr Val Pro Ser Val Ser His
        35                  40                  45

Phe Gly Val Phe Ser Ala Lys Glu Glu Arg Asn Ser Thr Val Gly Val
    50                  55                  60

Phe Gly Leu Lys His Asp Trp Asn Gly Gly Thr Ile Ser Asn Ser Ser
65                  70                  75                  80

Pro Glu Asn Ile Phe Thr Val Gln Asn Tyr Ser Phe Lys Tyr Glu Asn
                85                  90                  95
```

```
Asn Pro Phe Leu Gly Phe Ala Gly Ala Ile Gly Tyr Ser Met Gly Gly
            100                 105                 110

Pro Arg Ile Glu Leu Glu Val Leu Tyr Glu Thr Phe Asp Val Lys Asn
            115                 120                 125

Gln Asn Asn Tyr Lys Asn Gly Ala His Arg Tyr Cys Ala Leu Ser
    130                 135                 140

His His Ser Ser Ala Thr Asn Met Ser Ala Ser Asn Lys Phe Val
145                 150                 155                 160

Phe Leu Lys Asn Glu Gly Leu Ile Asp Leu Ser Phe Met Ile Asn Ala
                165                 170                 175

Cys Tyr Asp Ile Ile Glu Gly Met Pro Phe Ser Pro Tyr Ile Cys
                180                 185                 190

Ala Gly Val Gly Thr Asp Val Val Ser Met Phe Glu Ala Ile Asn Pro
            195                 200                 205

Lys Ile Ser Tyr Gln Gly Lys Leu Gly Leu Gly Tyr Ser Ile Ser Ser
            210                 215                 220

Glu Ala Ser Val Phe Ile Gly Gly His Phe His Arg Val Ile Gly Asn
225                 230                 235                 240

Glu Phe Arg Asp Ile Pro Ala Met Val Pro Ser Gly Ser Asn Leu Pro
                245                 250                 255

Glu Asn Gln Phe Ala Ile Val Thr Leu Asn Val Cys His Phe Gly Leu
            260                 265                 270

Glu Leu Gly Gly Arg Phe Asn Phe
            275                 280

<210> SEQ ID NO 39
<211> LENGTH: 852
<212> TYPE: DNA
<213> ORGANISM: Ehrlichia canis
<220> FEATURE:
<221> NAME/KEY: CDS
<222> LOCATION: (1)..(852)

<400> SEQUENCE: 39 atg aat tgt aaa aaa gtt ttc aca ata agt gca ttg ata tca tcc ata      48
Met Asn Cys Lys Lys Val Phe Thr Ile Ser Ala Leu Ile Ser Ser Ile
  1               5                  10                  15 tac ttc cta cct aat gtc tca tac tct aac cca gta tat ggt aac agt      96
Tyr Phe Leu Pro Asn Val Ser Tyr Ser Asn Pro Val Tyr Gly Asn Ser
                 20                  25                  30 atg tat ggt aat ttt tac ata tca gga aag tac atg cca agt gtt cct     144
Met Tyr Gly Asn Phe Tyr Ile Ser Gly Lys Tyr Met Pro Ser Val Pro
             35                  40                  45 cat ttt gga att ttt tca gct gaa gaa gag aaa aaa aag aca act gta     192
His Phe Gly Ile Phe Ser Ala Glu Glu Glu Lys Lys Lys Thr Thr Val
         50                  55                  60 gta tat ggc tta aaa gga aaa ctg gca gga gat gca ata tct agt caa     240
Val Tyr Gly Leu Lys Gly Lys Leu Ala Gly Asp Ala Ile Ser Ser Gln
 65                  70                  75                  80 agt cca gat gat aat ttt acc att cga aat tac tca ttc aag tat gca     288
Ser Pro Asp Asp Asn Phe Thr Ile Arg Asn Tyr Ser Phe Lys Tyr Ala
                 85                  90                  95 agc aac aag ttt tta ggg ttt gca gta gct att ggt tac tcg ata ggc     336
Ser Asn Lys Phe Leu Gly Phe Ala Val Ala Ile Gly Tyr Ser Ile Gly
                100                 105                 110 agt cca aga ata gaa gtt gag atg tct tat gaa gca ttt gat gtg aaa     384
Ser Pro Arg Ile Glu Val Glu Met Ser Tyr Glu Ala Phe Asp Val Lys
            115                 120                 125
```

```
aat cca ggt gat aat tac aaa aac ggt gct tac agg tat tgt gct tta      432
Asn Pro Gly Asp Asn Tyr Lys Asn Gly Ala Tyr Arg Tyr Cys Ala Leu
    130                 135                 140 tct cat caa gat gat gcg gat gat gac atg act agt gca act gac aaa      480
Ser His Gln Asp Asp Ala Asp Asp Asp Met Thr Ser Ala Thr Asp Lys
145                 150                 155                 160 ttt gta tat tta att aat gaa gga tta ctt aac ata tca ttt atg aca      528
Phe Val Tyr Leu Ile Asn Glu Gly Leu Leu Asn Ile Ser Phe Met Thr
                165                 170                 175 aac ata tgt tat gaa aca gca agc aaa aat ata cct ctc tct cct tac      576
Asn Ile Cys Tyr Glu Thr Ala Ser Lys Asn Ile Pro Leu Ser Pro Tyr
            180                 185                 190 ata tgt gca ggt att ggt act gat tta att cac atg ttt gaa act aca      624
Ile Cys Ala Gly Ile Gly Thr Asp Leu Ile His Met Phe Glu Thr Thr
        195                 200                 205 cat cct aaa att tct tat caa gga aag cta ggg ttg gcc tac ttc gta      672
His Pro Lys Ile Ser Tyr Gln Gly Lys Leu Gly Leu Ala Tyr Phe Val
    210                 215                 220 agt gca gag tct tcg gtt tct ttt ggt ata tat ttt cat aaa att ata      720
Ser Ala Glu Ser Ser Val Ser Phe Gly Ile Tyr Phe His Lys Ile Ile
225                 230                 235                 240 aat aat aag ttt aaa aat gtt cca gcc atg gta cct att aac tca gac      768
Asn Asn Lys Phe Lys Asn Val Pro Ala Met Val Pro Ile Asn Ser Asp
                245                 250                 255 gag ata gta gga cca cag ttt gca aca gta aca tta aat gta tgc tac      816
Glu Ile Val Gly Pro Gln Phe Ala Thr Val Thr Leu Asn Val Cys Tyr
            260                 265                 270 ttt gga tta gaa ctt gga tgt agg ttc aac ttc taa                      852
Phe Gly Leu Glu Leu Gly Cys Arg Phe Asn Phe
        275                 280
```

<210> SEQ ID NO 40
<211> LENGTH: 283
<212> TYPE: PRT
<213> ORGANISM: Ehrlichia canis

<400> SEQUENCE: 40

```
Met Asn Cys Lys Lys Val Phe Thr Ile Ser Ala Leu Ile Ser Ser Ile
1               5                   10                  15

Tyr Phe Leu Pro Asn Val Ser Tyr Ser Asn Pro Val Tyr Gly Asn Ser
            20                  25                  30

Met Tyr Gly Asn Phe Tyr Ile Ser Gly Lys Tyr Met Pro Ser Val Pro
        35                  40                  45

His Phe Gly Ile Phe Ser Ala Glu Glu Lys Lys Lys Thr Thr Val
    50                  55                  60

Val Tyr Gly Leu Lys Gly Lys Leu Ala Gly Asp Ala Ile Ser Ser Gln
65                  70                  75                  80

Ser Pro Asp Asp Asn Phe Thr Ile Arg Asn Tyr Ser Phe Lys Tyr Ala
                85                  90                  95

Ser Asn Lys Phe Leu Gly Phe Ala Val Ala Ile Gly Tyr Ser Ile Gly
            100                 105                 110

Ser Pro Arg Ile Glu Val Glu Met Ser Tyr Glu Ala Phe Asp Val Lys
        115                 120                 125

Asn Pro Gly Asp Asn Tyr Lys Asn Gly Ala Tyr Arg Tyr Cys Ala Leu
    130                 135                 140

Ser His Gln Asp Asp Ala Asp Asp Asp Met Thr Ser Ala Thr Asp Lys
145                 150                 155                 160

Phe Val Tyr Leu Ile Asn Glu Gly Leu Leu Asn Ile Ser Phe Met Thr
```

```
                        165                 170                 175
Asn Ile Cys Tyr Glu Thr Ala Ser Lys Asn Ile Pro Leu Ser Pro Tyr
            180                 185                 190

Ile Cys Ala Gly Ile Gly Thr Asp Leu Ile His Met Phe Glu Thr Thr
            195                 200                 205

His Pro Lys Ile Ser Tyr Gln Gly Lys Leu Gly Leu Ala Tyr Phe Val
            210                 215                 220

Ser Ala Glu Ser Ser Val Ser Phe Gly Ile Tyr Phe His Lys Ile Ile
225                 230                 235                 240

Asn Asn Lys Phe Lys Asn Val Pro Ala Met Val Pro Ile Asn Ser Asp
                245                 250                 255

Glu Ile Val Gly Pro Gln Phe Ala Thr Val Thr Leu Asn Val Cys Tyr
            260                 265                 270

Phe Gly Leu Glu Leu Gly Cys Arg Phe Asn Phe
            275                 280

<210> SEQ ID NO 41
<211> LENGTH: 831
<212> TYPE: DNA
<213> ORGANISM: Ehrlichia canis
<220> FEATURE:
<221> NAME/KEY: CDS
<222> LOCATION: (1)..(831)

<400> SEQUENCE: 41 atg aac tgt aaa aaa ttt ctt ata aca act aca ttg gta tca cta aca      48
Met Asn Cys Lys Lys Phe Leu Ile Thr Thr Thr Leu Val Ser Leu Thr
 1               5                  10                  15 att ctt tta cct ggc ata tct ttc tcc aaa cca ata cat gaa aac aat      96
Ile Leu Leu Pro Gly Ile Ser Phe Ser Lys Pro Ile His Glu Asn Asn
             20                  25                  30 act aca gga aac ttt tac att att gga aaa tat gta cca agt att tca     144
Thr Thr Gly Asn Phe Tyr Ile Ile Gly Lys Tyr Val Pro Ser Ile Ser
         35                  40                  45 cat ttt ggg aac ttt tca gct aaa gaa gaa aaa aac aca act act gga     192
His Phe Gly Asn Phe Ser Ala Lys Glu Glu Lys Asn Thr Thr Thr Gly
     50                  55                  60 att ttt gga tta aaa gaa tca tgg act ggt ggt atc atc ctt gat aaa     240
Ile Phe Gly Leu Lys Glu Ser Trp Thr Gly Gly Ile Ile Leu Asp Lys
 65                  70                  75                  80 gaa cat gca gct ttt aat atc cca aat tat tca ttt aaa tat gaa aat     288
Glu His Ala Ala Phe Asn Ile Pro Asn Tyr Ser Phe Lys Tyr Glu Asn
                 85                  90                  95 aat cca ttt tta gga ttt gca ggg gta att ggc tat tca ata ggt agt     336
Asn Pro Phe Leu Gly Phe Ala Gly Val Ile Gly Tyr Ser Ile Gly Ser
            100                 105                 110 cca aga ata gaa ttt gaa gta tca tac gag aca ttc gat gta caa aat     384
Pro Arg Ile Glu Phe Glu Val Ser Tyr Glu Thr Phe Asp Val Gln Asn
        115                 120                 125 cca gga gat aag ttt aac aat gat gca cat aag tat tgt gct tta tcc     432
Pro Gly Asp Lys Phe Asn Asn Asp Ala His Lys Tyr Cys Ala Leu Ser
    130                 135                 140 aat gat tcc agt aaa aca atg aaa agt ggt aaa ttc gtt ttt ctc aaa     480
Asn Asp Ser Ser Lys Thr Met Lys Ser Gly Lys Phe Val Phe Leu Lys
145                 150                 155                 160 aat gaa gga tta agt gac ata tca ctc atg tta aat gta tgt tat gat     528
Asn Glu Gly Leu Ser Asp Ile Ser Leu Met Leu Asn Val Cys Tyr Asp
                165                 170                 175 ata ata aac aaa aga atg cct ttt tca cct tac ata tgt gca ggc att     576
```

```
Ile Ile Asn Lys Arg Met Pro Phe Ser Pro Tyr Ile Cys Ala Gly Ile
            180                 185                 190 ggt act gac tta ata ttc atg ttt gac gct ata aac cat aaa gct gct    624
Gly Thr Asp Leu Ile Phe Met Phe Asp Ala Ile Asn His Lys Ala Ala
            195                 200                 205 tat caa gga aaa tta ggt ttt aat tat cca ata agc cca gaa gct aac    672
Tyr Gln Gly Lys Leu Gly Phe Asn Tyr Pro Ile Ser Pro Glu Ala Asn
            210                 215                 220 att tct atg ggt gtg cac ttt cac aaa gta aca aac aac gag ttt aga    720
Ile Ser Met Gly Val His Phe His Lys Val Thr Asn Asn Glu Phe Arg
225                 230                 235                 240 gtt cct gtt cta tta act gct gga gga ctc gct cca gat aat cta ttt    768
Val Pro Val Leu Leu Thr Ala Gly Gly Leu Ala Pro Asp Asn Leu Phe
                245                 250                 255 gca ata gta aag ttg agt ata tgt cat ttt ggg tta gaa ttt ggg tac    816
Ala Ile Val Lys Leu Ser Ile Cys His Phe Gly Leu Glu Phe Gly Tyr
            260                 265                 270 agg gtc agt ttt taa                                                831
Arg Val Ser Phe
            275

<210> SEQ ID NO 42
<211> LENGTH: 276
<212> TYPE: PRT
<213> ORGANISM: Ehrlichia canis

<400> SEQUENCE: 42

Met Asn Cys Lys Lys Phe Leu Ile Thr Thr Thr Leu Val Ser Leu Thr
 1               5                  10                  15

Ile Leu Leu Pro Gly Ile Ser Phe Ser Lys Pro Ile His Glu Asn Asn
            20                  25                  30

Thr Thr Gly Asn Phe Tyr Ile Ile Gly Lys Tyr Val Pro Ser Ile Ser
        35                  40                  45

His Phe Gly Asn Phe Ser Ala Lys Glu Glu Lys Asn Thr Thr Thr Gly
    50                  55                  60

Ile Phe Gly Leu Lys Glu Ser Trp Thr Gly Gly Ile Ile Leu Asp Lys
65                  70                  75                  80

Glu His Ala Ala Phe Asn Ile Pro Asn Tyr Ser Phe Lys Tyr Glu Asn
                85                  90                  95

Asn Pro Phe Leu Gly Phe Ala Gly Val Ile Gly Tyr Ser Ile Gly Ser
            100                 105                 110

Pro Arg Ile Glu Phe Glu Val Ser Tyr Glu Thr Phe Asp Val Gln Asn
        115                 120                 125

Pro Gly Asp Lys Phe Asn Asn Asp Ala His Lys Tyr Cys Ala Leu Ser
    130                 135                 140

Asn Asp Ser Ser Lys Thr Met Lys Ser Gly Lys Phe Val Phe Leu Lys
145                 150                 155                 160

Asn Glu Gly Leu Ser Asp Ile Ser Leu Met Leu Asn Val Cys Tyr Asp
                165                 170                 175

Ile Ile Asn Lys Arg Met Pro Phe Ser Pro Tyr Ile Cys Ala Gly Ile
            180                 185                 190

Gly Thr Asp Leu Ile Phe Met Phe Asp Ala Ile Asn His Lys Ala Ala
        195                 200                 205

Tyr Gln Gly Lys Leu Gly Phe Asn Tyr Pro Ile Ser Pro Glu Ala Asn
    210                 215                 220

Ile Ser Met Gly Val His Phe His Lys Val Thr Asn Asn Glu Phe Arg
225                 230                 235                 240
```

```
Val Pro Val Leu Leu Thr Ala Gly Gly Leu Ala Pro Asp Asn Leu Phe
            245                 250                 255

Ala Ile Val Lys Leu Ser Ile Cys His Phe Gly Leu Glu Phe Gly Tyr
        260                 265                 270

Arg Val Ser Phe
        275

<210> SEQ ID NO 43
<211> LENGTH: 882
<212> TYPE: DNA
<213> ORGANISM: Ehrlichia canis
<220> FEATURE:
<221> NAME/KEY: CDS
<222> LOCATION: (1)..(882)

<400> SEQUENCE: 43 atg aat aat aaa ctc aaa ttt act ata ata aac aca gta tta gta tgc      48
Met Asn Asn Lys Leu Lys Phe Thr Ile Ile Asn Thr Val Leu Val Cys
  1               5                  10                  15 tta ttg tca tta cct aat ata tct tcc tca aag gcc ata aac aat aac      96
Leu Leu Ser Leu Pro Asn Ile Ser Ser Ser Lys Ala Ile Asn Asn Asn
             20                  25                  30 gct aaa aag tac tac gga tta tat atc agt gga caa tat aaa ccc agt     144
Ala Lys Lys Tyr Tyr Gly Leu Tyr Ile Ser Gly Gln Tyr Lys Pro Ser
         35                  40                  45 gtt tct gtt ttc agt aat ttt tca gtt aaa gaa acc aat gtc ata act     192
Val Ser Val Phe Ser Asn Phe Ser Val Lys Glu Thr Asn Val Ile Thr
     50                  55                  60 aaa aac ctt ata gct tta aaa aaa gat gtt gac tct att gaa acc aag     240
Lys Asn Leu Ile Ala Leu Lys Lys Asp Val Asp Ser Ile Glu Thr Lys
 65                  70                  75                  80 act gat gcc agt gta ggt att agt aac cca tca aat ttt act atc ccc     288
Thr Asp Ala Ser Val Gly Ile Ser Asn Pro Ser Asn Phe Thr Ile Pro
                 85                  90                  95 tat aca gct gta ttt caa gat aat tct gtc aat ttc aat gga act att     336
Tyr Thr Ala Val Phe Gln Asp Asn Ser Val Asn Phe Asn Gly Thr Ile
            100                 105                 110 ggt tac acc ttt gct gaa ggt aca aga gtt gaa ata gaa ggt tct tat     384
Gly Tyr Thr Phe Ala Glu Gly Thr Arg Val Glu Ile Glu Gly Ser Tyr
        115                 120                 125 gag gaa ttt gat gtt aaa aac cct gga ggc tat aca cta agt gat gcc     432
Glu Glu Phe Asp Val Lys Asn Pro Gly Gly Tyr Thr Leu Ser Asp Ala
    130                 135                 140 tat cgc tat ttt gca tta gca cgt gaa atg aaa ggt aat agt ttt aca     480
Tyr Arg Tyr Phe Ala Leu Ala Arg Glu Met Lys Gly Asn Ser Phe Thr
145                 150                 155                 160 cct aaa gaa aaa gtt tct aat agt ttt ttt cac act gta atg aga aat     528
Pro Lys Glu Lys Val Ser Asn Ser Phe Phe His Thr Val Met Arg Asn
                165                 170                 175 gat gga tta tct ata ata tct gtt ata gta aat gtt tgc tac gat ttc     576
Asp Gly Leu Ser Ile Ile Ser Val Ile Val Asn Val Cys Tyr Asp Phe
            180                 185                 190 tct ttg aac aat ttg tca ata tcg cct tac ata tgt gga gga gca ggg     624
Ser Leu Asn Asn Leu Ser Ile Ser Pro Tyr Ile Cys Gly Gly Ala Gly
        195                 200                 205 gta gat gct ata gaa ttc ttc gat gta tta cac att aag ttt gca tat     672
Val Asp Ala Ile Glu Phe Phe Asp Val Leu His Ile Lys Phe Ala Tyr
    210                 215                 220 caa agc aag cta ggt att gct tat tct cta cca tct aac att agt ctc     720
Gln Ser Lys Leu Gly Ile Ala Tyr Ser Leu Pro Ser Asn Ile Ser Leu
```

```
ttt gct agt tta tat tac cat aaa gta atg ggc aat caa ttt aaa aat    768
Phe Ala Ser Leu Tyr Tyr His Lys Val Met Gly Asn Gln Phe Lys Asn
            245                 250                 255 tta aat gtc caa gat gtt gct gaa ctt gca agt ata cct aaa att aca    816
Leu Asn Val Gln Asp Val Ala Glu Leu Ala Ser Ile Pro Lys Ile Thr
            260                 265                 270 tcc gca gtt gct aca ctt aat att ggt tat ttt gga ggt gaa att ggt    864
Ser Ala Val Ala Thr Leu Asn Ile Gly Tyr Phe Gly Gly Glu Ile Gly
            275                 280                 285 gca aga ttg aca ttt taa                                            882
Ala Arg Leu Thr Phe
    290

<210> SEQ ID NO 44
<211> LENGTH: 293
<212> TYPE: PRT
<213> ORGANISM: Ehrlichia canis

<400> SEQUENCE: 44

Met Asn Asn Lys Leu Lys Phe Thr Ile Ile Asn Thr Val Leu Val Cys
 1               5                  10                  15

Leu Leu Ser Leu Pro Asn Ile Ser Ser Ser Lys Ala Ile Asn Asn Asn
            20                  25                  30

Ala Lys Lys Tyr Tyr Gly Leu Tyr Ile Ser Gly Gln Tyr Lys Pro Ser
        35                  40                  45

Val Ser Val Phe Ser Asn Phe Ser Val Lys Glu Thr Asn Val Ile Thr
    50                  55                  60

Lys Asn Leu Ile Ala Leu Lys Lys Asp Val Asp Ser Ile Glu Thr Lys
65                  70                  75                  80

Thr Asp Ala Ser Val Gly Ile Ser Asn Pro Ser Asn Phe Thr Ile Pro
                85                  90                  95

Tyr Thr Ala Val Phe Gln Asp Asn Ser Val Asn Phe Asn Gly Thr Ile
            100                 105                 110

Gly Tyr Thr Phe Ala Glu Gly Thr Arg Val Glu Ile Glu Gly Ser Tyr
        115                 120                 125

Glu Glu Phe Asp Val Lys Asn Pro Gly Gly Tyr Thr Leu Ser Asp Ala
130                 135                 140

Tyr Arg Tyr Phe Ala Leu Ala Arg Glu Met Lys Gly Asn Ser Phe Thr
145                 150                 155                 160

Pro Lys Glu Lys Val Ser Asn Ser Phe Phe His Thr Val Met Arg Asn
                165                 170                 175

Asp Gly Leu Ser Ile Ile Ser Val Ile Val Asn Val Cys Tyr Asp Phe
            180                 185                 190

Ser Leu Asn Asn Leu Ser Ile Ser Pro Tyr Ile Cys Gly Gly Ala Gly
        195                 200                 205

Val Asp Ala Ile Glu Phe Phe Asp Val Leu His Ile Lys Phe Ala Tyr
    210                 215                 220

Gln Ser Lys Leu Gly Ile Ala Tyr Ser Leu Pro Ser Asn Ile Ser Leu
225                 230                 235                 240

Phe Ala Ser Leu Tyr Tyr His Lys Val Met Gly Asn Gln Phe Lys Asn
                245                 250                 255

Leu Asn Val Gln Asp Val Ala Glu Leu Ala Ser Ile Pro Lys Ile Thr
            260                 265                 270

Ser Ala Val Ala Thr Leu Asn Ile Gly Tyr Phe Gly Gly Glu Ile Gly
        275                 280                 285
```

Ala Arg Leu Thr Phe
    290

<210> SEQ ID NO 45
<211> LENGTH: 900
<212> TYPE: DNA
<213> ORGANISM: Ehrlichia canis
<220> FEATURE:
<221> NAME/KEY: CDS
<222> LOCATION: (1)..(900)

<400> SEQUENCE: 45

```
atg aat agc aag agt aag ttc ttt aca ata tgt aca tcg tta ata tgc      48
Met Asn Ser Lys Ser Lys Phe Phe Thr Ile Cys Thr Ser Leu Ile Cys
 1               5                  10                  15 tta tta tca tca cct aac aca tct ctc tca aac ttc ata ggc aat agt      96
Leu Leu Ser Ser Pro Asn Thr Ser Leu Ser Asn Phe Ile Gly Asn Ser
             20                  25                  30 aca aaa cat tct gga tta tat gtt agc gga cat tat aag ccc agc gtt     144
Thr Lys His Ser Gly Leu Tyr Val Ser Gly His Tyr Lys Pro Ser Val
         35                  40                  45 tcc att ttt agc aaa ttt tca gta aaa gaa aca aat aca cat aca gta     192
Ser Ile Phe Ser Lys Phe Ser Val Lys Glu Thr Asn Thr His Thr Val
     50                  55                  60 cag tta gta gct ctt aaa aaa gat gtt aat tct att tct atg aac atc     240
Gln Leu Val Ala Leu Lys Lys Asp Val Asn Ser Ile Ser Met Asn Ile
 65                  70                  75                  80 agt aat ggt gct aca ggc att agc aaa gca aca aat ttt aat ctt cct     288
Ser Asn Gly Ala Thr Gly Ile Ser Lys Ala Thr Asn Phe Asn Leu Pro
                 85                  90                  95 tat gtt gca gaa ttt caa gac aat gcc ttc aac ttc agt gga gct att     336
Tyr Val Ala Glu Phe Gln Asp Asn Ala Phe Asn Phe Ser Gly Ala Ile
            100                 105                 110 ggt tat tca ctt ttt gaa caa cta aac att gaa gtt gaa ggt tct tat     384
Gly Tyr Ser Leu Phe Glu Gln Leu Asn Ile Glu Val Glu Gly Ser Tyr
        115                 120                 125 gaa gaa ttc gat gcc aaa aat cct ggt ggt tat att tta aat gat gca     432
Glu Glu Phe Asp Ala Lys Asn Pro Gly Gly Tyr Ile Leu Asn Asp Ala
    130                 135                 140 ttc cgc tat ttt gca ttg gca cgt gaa atg gga caa gaa aaa aat gat     480
Phe Arg Tyr Phe Ala Leu Ala Arg Glu Met Gly Gln Glu Lys Asn Asp
145                 150                 155                 160 aat aag cat ctt agt cct aag gag gag cat gat ata agt aaa aca tat     528
Asn Lys His Leu Ser Pro Lys Glu Glu His Asp Ile Ser Lys Thr Tyr
                165                 170                 175 tac aca gtc atg aga aat aat ggg tta tct ata tta tct att atg ata     576
Tyr Thr Val Met Arg Asn Asn Gly Leu Ser Ile Leu Ser Ile Met Ile
            180                 185                 190 aat ggc tgc tat aat cta cct ctc aat gat tta tca ata tca cct tat     624
Asn Gly Cys Tyr Asn Leu Pro Leu Asn Asp Leu Ser Ile Ser Pro Tyr
        195                 200                 205 ttt tgt aca gga ata ggt gta gat gct ata gaa ttt ttt gat gca ctg     672
Phe Cys Thr Gly Ile Gly Val Asp Ala Ile Glu Phe Phe Asp Ala Leu
    210                 215                 220 cat ctt aaa ctt gct ttg caa agt aaa ata gga gct act tac caa tta     720
His Leu Lys Leu Ala Leu Gln Ser Lys Ile Gly Ala Thr Tyr Gln Leu
225                 230                 235                 240 tca gac aac att agt tta ttt aca aat gga tat tac cat caa gta ata     768
Ser Asp Asn Ile Ser Leu Phe Thr Asn Gly Tyr Tyr His Gln Val Ile
                245                 250                 255
```

```
ggt gat caa ttt aaa aac tta aaa gtc caa tat ata ggt gaa ctt aaa      816
Gly Asp Gln Phe Lys Asn Leu Lys Val Gln Tyr Ile Gly Glu Leu Lys
        260                 265                 270 gag aac ccg aaa att aca tct gca gtt gct act ctc aat gtt gga tac      864
Glu Asn Pro Lys Ile Thr Ser Ala Val Ala Thr Leu Asn Val Gly Tyr
        275                 280                 285 ttt gga ggt gaa att gga gta aga ctc aca ctt taa                      900
Phe Gly Gly Glu Ile Gly Val Arg Leu Thr Leu
        290                 295                 300

<210> SEQ ID NO 46
<211> LENGTH: 299
<212> TYPE: PRT
<213> ORGANISM: Ehrlichia canis

<400> SEQUENCE: 46

Met Asn Ser Lys Ser Lys Phe Phe Thr Ile Cys Thr Ser Leu Ile Cys
  1               5                  10                  15

Leu Leu Ser Ser Pro Asn Thr Ser Leu Ser Asn Phe Ile Gly Asn Ser
             20                  25                  30

Thr Lys His Ser Gly Leu Tyr Val Ser Gly His Tyr Lys Pro Ser Val
         35                  40                  45

Ser Ile Phe Ser Lys Phe Ser Val Lys Glu Thr Asn Thr His Thr Val
     50                  55                  60

Gln Leu Val Ala Leu Lys Lys Asp Val Asn Ser Ile Ser Met Asn Ile
 65                  70                  75                  80

Ser Asn Gly Ala Thr Gly Ile Ser Lys Ala Thr Asn Phe Asn Leu Pro
                 85                  90                  95

Tyr Val Ala Glu Phe Gln Asp Asn Ala Phe Asn Phe Ser Gly Ala Ile
            100                 105                 110

Gly Tyr Ser Leu Phe Glu Gln Leu Asn Ile Glu Val Glu Gly Ser Tyr
        115                 120                 125

Glu Glu Phe Asp Ala Lys Asn Pro Gly Gly Tyr Ile Leu Asn Asp Ala
    130                 135                 140

Phe Arg Tyr Phe Ala Leu Ala Arg Glu Met Gly Gln Glu Lys Asn Asp
145                 150                 155                 160

Asn Lys His Leu Ser Pro Lys Glu Glu His Asp Ile Ser Lys Thr Tyr
                165                 170                 175

Tyr Thr Val Met Arg Asn Asn Gly Leu Ser Ile Leu Ser Ile Met Ile
            180                 185                 190

Asn Gly Cys Tyr Asn Leu Pro Leu Asn Asp Leu Ser Ile Ser Pro Tyr
        195                 200                 205

Phe Cys Thr Gly Ile Gly Val Asp Ala Ile Glu Phe Phe Asp Ala Leu
    210                 215                 220

His Leu Lys Leu Ala Leu Gln Ser Lys Ile Gly Ala Thr Tyr Gln Leu
225                 230                 235                 240

Ser Asp Asn Ile Ser Leu Phe Thr Asn Gly Tyr Tyr His Gln Val Ile
                245                 250                 255

Gly Asp Gln Phe Lys Asn Leu Val Gln Tyr Ile Gly Glu Leu Lys
            260                 265                 270

Glu Asn Pro Lys Ile Thr Ser Ala Val Ala Thr Leu Asn Val Gly Tyr
        275                 280                 285

Phe Gly Gly Glu Ile Gly Val Arg Leu Thr Leu
    290                 295

<210> SEQ ID NO 47
```

```
<211> LENGTH: 843
<212> TYPE: DNA
<213> ORGANISM: Ehrlichia canis
<220> FEATURE:
<221> NAME/KEY: CDS
<222> LOCATION: (1)..(843)

<400> SEQUENCE: 47
```

| | | | | | | | | | | | | | | | | |
|---|---|---|---|---|---|---|---|---|---|---|---|---|---|---|---|---|
| atg | aat | tat | aag | aaa | att | cta | gta | aga | agc | gcg | tta | atc | tca | tta | atg | 48 |
| Met | Asn | Tyr | Lys | Lys | Ile | Leu | Val | Arg | Ser | Ala | Leu | Ile | Ser | Leu | Met | |
| 1 | | | | 5 | | | | | 10 | | | | | 15 | | |
| tca | atc | tta | cca | tat | cag | tct | ttt | gca | gat | cct | gta | ggt | tca | aga | act | 96 |
| Ser | Ile | Leu | Pro | Tyr | Gln | Ser | Phe | Ala | Asp | Pro | Val | Gly | Ser | Arg | Thr | |
| | | | 20 | | | | | 25 | | | | | 30 | | | |
| aat | gat | aac | aaa | gaa | ggc | ttc | tac | att | agt | gca | aag | tac | aat | cca | agt | 144 |
| Asn | Asp | Asn | Lys | Glu | Gly | Phe | Tyr | Ile | Ser | Ala | Lys | Tyr | Asn | Pro | Ser | |
| | | 35 | | | | | 40 | | | | | 45 | | | | |
| ata | tca | cac | ttt | aga | aaa | ttc | tct | gct | gaa | gaa | act | cct | att | aat | gga | 192 |
| Ile | Ser | His | Phe | Arg | Lys | Phe | Ser | Ala | Glu | Glu | Thr | Pro | Ile | Asn | Gly | |
| | 50 | | | | | 55 | | | | | 60 | | | | | |
| aca | aat | tct | ctc | act | aaa | aaa | gtt | ttc | gga | cta | aag | aaa | gat | ggt | gat | 240 |
| Thr | Asn | Ser | Leu | Thr | Lys | Lys | Val | Phe | Gly | Leu | Lys | Lys | Asp | Gly | Asp | |
| 65 | | | | | 70 | | | | | 75 | | | | | 80 | |
| ata | aca | aaa | aaa | gac | gat | ttt | aca | aga | gta | gct | cca | ggc | att | gat | ttt | 288 |
| Ile | Thr | Lys | Lys | Asp | Asp | Phe | Thr | Arg | Val | Ala | Pro | Gly | Ile | Asp | Phe | |
| | | | | 85 | | | | | 90 | | | | | 95 | | |
| caa | aat | aac | tta | ata | tca | gga | ttt | tca | gga | agt | att | ggt | tac | tct | atg | 336 |
| Gln | Asn | Asn | Leu | Ile | Ser | Gly | Phe | Ser | Gly | Ser | Ile | Gly | Tyr | Ser | Met | |
| | | | 100 | | | | | 105 | | | | | 110 | | | |
| gac | gga | cca | aga | ata | gaa | ctt | gaa | gct | gca | tat | caa | caa | ttt | aat | cca | 384 |
| Asp | Gly | Pro | Arg | Ile | Glu | Leu | Glu | Ala | Ala | Tyr | Gln | Gln | Phe | Asn | Pro | |
| | | 115 | | | | | 120 | | | | | 125 | | | | |
| aaa | aac | acc | gat | aac | aat | gat | act | gat | aat | ggt | gaa | tac | tat | aaa | cat | 432 |
| Lys | Asn | Thr | Asp | Asn | Asn | Asp | Thr | Asp | Asn | Gly | Glu | Tyr | Tyr | Lys | His | |
| 130 | | | | | 135 | | | | | 140 | | | | | | |
| ttt | gca | tta | tct | cgt | aaa | gat | gca | atg | gaa | gat | cag | caa | tat | gta | gta | 480 |
| Phe | Ala | Leu | Ser | Arg | Lys | Asp | Ala | Met | Glu | Asp | Gln | Gln | Tyr | Val | Val | |
| 145 | | | | | 150 | | | | | 155 | | | | | 160 | |
| ctt | aaa | aat | gac | ggc | ata | act | ttt | atg | tca | ttg | atg | gtt | aat | act | tgc | 528 |
| Leu | Lys | Asn | Asp | Gly | Ile | Thr | Phe | Met | Ser | Leu | Met | Val | Asn | Thr | Cys | |
| | | | | 165 | | | | | 170 | | | | | 175 | | |
| tat | gac | att | aca | gct | gaa | gga | gta | tct | ttc | gta | cca | tat | gca | tgt | gca | 576 |
| Tyr | Asp | Ile | Thr | Ala | Glu | Gly | Val | Ser | Phe | Val | Pro | Tyr | Ala | Cys | Ala | |
| | | | 180 | | | | | 185 | | | | | 190 | | | |
| ggt | ata | gga | gca | gat | ctt | atc | act | att | ttt | aaa | gac | ctc | aat | cta | aaa | 624 |
| Gly | Ile | Gly | Ala | Asp | Leu | Ile | Thr | Ile | Phe | Lys | Asp | Leu | Asn | Leu | Lys | |
| | | 195 | | | | | 200 | | | | | 205 | | | | |
| ttt | gct | tac | caa | gga | aaa | ata | ggt | att | agt | tac | cct | atc | aca | cca | gaa | 672 |
| Phe | Ala | Tyr | Gln | Gly | Lys | Ile | Gly | Ile | Ser | Tyr | Pro | Ile | Thr | Pro | Glu | |
| | 210 | | | | | 215 | | | | | 220 | | | | | |
| gtc | tct | gca | ttt | att | ggt | gga | tac | tac | cat | ggc | gtt | att | ggt | aat | aaa | 720 |
| Val | Ser | Ala | Phe | Ile | Gly | Gly | Tyr | Tyr | His | Gly | Val | Ile | Gly | Asn | Lys | |
| 225 | | | | | 230 | | | | | 235 | | | | | 240 | |
| ttt | gag | aag | ata | cct | gta | ata | act | cct | gta | gta | tta | aat | gat | gct | cct | 768 |
| Phe | Glu | Lys | Ile | Pro | Val | Ile | Thr | Pro | Val | Val | Leu | Asn | Asp | Ala | Pro | |
| | | | | 245 | | | | | 250 | | | | | 255 | | |
| caa | acc | aca | tct | gct | tca | gta | act | ctt | gac | gtt | gga | tac | ttt | ggc | gga | 816 |
| Gln | Thr | Thr | Ser | Ala | Ser | Val | Thr | Leu | Asp | Val | Gly | Tyr | Phe | Gly | Gly | |
| | | | 260 | | | | | 265 | | | | | 270 | | | |
| gaa | att | gga | atg | agg | ttc | acc | ttc | taa | | | | | | | | 843 |
| Glu | Ile | Gly | Met | Arg | Phe | Thr | Phe | | | | | | | | | |

-continued

<210> SEQ ID NO 48
<211> LENGTH: 280
<212> TYPE: PRT
<213> ORGANISM: Ehrlichia canis

<400> SEQUENCE: 48

```
Met Asn Tyr Lys Lys Ile Leu Val Arg Ser Ala Leu Ile Ser Leu Met
 1               5                  10                  15

Ser Ile Leu Pro Tyr Gln Ser Phe Ala Asp Pro Val Gly Ser Arg Thr
            20                  25                  30

Asn Asp Asn Lys Glu Gly Phe Tyr Ile Ser Ala Lys Tyr Asn Pro Ser
        35                  40                  45

Ile Ser His Phe Arg Lys Phe Ser Ala Glu Glu Thr Pro Ile Asn Gly
    50                  55                  60

Thr Asn Ser Leu Thr Lys Lys Val Phe Gly Leu Lys Lys Asp Gly Asp
 65                  70                  75                  80

Ile Thr Lys Lys Asp Asp Phe Thr Arg Val Ala Pro Gly Ile Asp Phe
                85                  90                  95

Gln Asn Asn Leu Ile Ser Gly Phe Ser Gly Ser Ile Gly Tyr Ser Met
            100                 105                 110

Asp Gly Pro Arg Ile Glu Leu Glu Ala Ala Tyr Gln Gln Phe Asn Pro
        115                 120                 125

Lys Asn Thr Asp Asn Asn Asp Thr Asp Asn Gly Glu Tyr Tyr Lys His
    130                 135                 140

Phe Ala Leu Ser Arg Lys Asp Ala Met Glu Asp Gln Gln Tyr Val Val
145                 150                 155                 160

Leu Lys Asn Asp Gly Ile Thr Phe Met Ser Leu Met Val Asn Thr Cys
                165                 170                 175

Tyr Asp Ile Thr Ala Glu Gly Val Ser Phe Val Pro Tyr Ala Cys Ala
            180                 185                 190

Gly Ile Gly Ala Asp Leu Ile Thr Ile Phe Lys Asp Leu Asn Leu Lys
        195                 200                 205

Phe Ala Tyr Gln Gly Lys Ile Gly Ile Ser Tyr Pro Ile Thr Pro Glu
    210                 215                 220

Val Ser Ala Phe Ile Gly Gly Tyr Tyr His Gly Val Ile Gly Asn Lys
225                 230                 235                 240

Phe Glu Lys Ile Pro Val Ile Thr Pro Val Val Leu Asn Asp Ala Pro
                245                 250                 255

Gln Thr Thr Ser Ala Ser Val Thr Leu Asp Val Gly Tyr Phe Gly Gly
            260                 265                 270

Glu Ile Gly Met Arg Phe Thr Phe
        275                 280
```

<210> SEQ ID NO 49
<211> LENGTH: 903
<212> TYPE: DNA
<213> ORGANISM: OMP-1Z
<220> FEATURE:
<221> NAME/KEY: CDS
<222> LOCATION: (1)..(903)

<400> SEQUENCE: 49

```
atg aag aag aaa aat caa ttt atc aca ata agt aca ata tta gta tgt    48
Met Lys Lys Lys Asn Gln Phe Ile Thr Ile Ser Thr Ile Leu Val Cys
 1               5                  10                  15
```

-continued

| | | |
|---|---|---|
| tta ttg tca tta tct aat gca tca ctt tca aac act aca aat agc agc<br>Leu Leu Ser Leu Ser Asn Ala Ser Leu Ser Asn Thr Thr Asn Ser Ser<br>20                25                30 | 96 | |
| act aaa aaa cag ttt ggg tta tat gtt agt gga caa tac aag cct agt<br>Thr Lys Lys Gln Phe Gly Leu Tyr Val Ser Gly Gln Tyr Lys Pro Ser<br>    35                40                45 | 144 | |
| gtt tct att ttt agc aat ttc tca gta aag gaa act aat ttt cct aca<br>Val Ser Ile Phe Ser Asn Phe Ser Val Lys Glu Thr Asn Phe Pro Thr<br>50                55                60 | 192 | |
| aag tat cta gca gct ctt aaa aaa gac att aat tct gtc gaa ttt gac<br>Lys Tyr Leu Ala Ala Leu Lys Lys Asp Ile Asn Ser Val Glu Phe Asp<br>65                70                75                80 | 240 | |
| gat agt gtt act gct ggc att agt tac cca ctt aat ttc agt act cct<br>Asp Ser Val Thr Ala Gly Ile Ser Tyr Pro Leu Asn Phe Ser Thr Pro<br>            85                90                95 | 288 | |
| tat ata gct gta ttt caa gat aat att tct aat ttt aat ggc gct att<br>Tyr Ile Ala Val Phe Gln Asp Asn Ile Ser Asn Phe Asn Gly Ala Ile<br>            100               105               110 | 336 | |
| ggg tac act ttt gtt gaa ggc cca aga att gaa ata gaa ggt tct tat<br>Gly Tyr Thr Phe Val Glu Gly Pro Arg Ile Glu Ile Glu Gly Ser Tyr<br>        115               120               125 | 384 | |
| gaa gaa ttc gat gtc aaa gac ctg gaa gat ata cag aaa tac aag atg<br>Glu Glu Phe Asp Val Lys Asp Leu Glu Asp Ile Gln Lys Tyr Lys Met<br>130               135               140 | 432 | |
| cat acc gtt gac ttt gct tta gca cgt gat ata gac tct att cct act<br>His Thr Val Asp Phe Ala Leu Ala Arg Asp Ile Asp Ser Ile Pro Thr<br>145               150               155               160 | 480 | |
| agc cca aaa aat aga act tca cat gat ggc aac agt tca tat aag gta<br>Ser Pro Lys Asn Arg Thr Ser His Asp Gly Asn Ser Ser Tyr Lys Val<br>            165               170               175 | 528 | |
| tac cac act gta atg aaa aat gaa gga cta tct ata ata tcc att atg<br>Tyr His Thr Val Met Lys Asn Glu Gly Leu Ser Ile Ile Ser Ile Met<br>        180               185               190 | 576 | |
| gtc aat ggc tgc tat gat ttt tct tca gat aat tta tca ata tta cct<br>Val Asn Gly Cys Tyr Asp Phe Ser Ser Asp Asn Leu Ser Ile Leu Pro<br>    195               200               205 | 624 | |
| tat gta tgt ggt ggt ata ggt gta aat gct ata gag ttt ttc gat gca<br>Tyr Val Cys Gly Gly Ile Gly Val Asn Ala Ile Glu Phe Phe Asp Ala<br>210               215               220 | 672 | |
| tta cat gtt aaa ttc gcg tgt cag ggt aaa tta ggt att act tat cca<br>Leu His Val Lys Phe Ala Cys Gln Gly Lys Leu Gly Ile Thr Tyr Pro<br>225               230               235               240 | 720 | |
| tta tct tcc aac gtt agt tta ttt gct ggt gga tat tat cac caa gta<br>Leu Ser Ser Asn Val Ser Leu Phe Ala Gly Gly Tyr Tyr His Gln Val<br>            245               250               255 | 768 | |
| atg ggc aac caa ttt aaa aat cta aat gtt caa cat gta gct gaa ctt<br>Met Gly Asn Gln Phe Lys Asn Leu Asn Val Gln His Val Ala Glu Leu<br>        260               265               270 | 816 | |
| aat gac gca ccc aaa gtt aca tct gca gta gct aca ctt gac att ggg<br>Asn Asp Ala Pro Lys Val Thr Ser Ala Val Ala Thr Leu Asp Ile Gly<br>    275               280               285 | 864 | |
| tat ttt ggt ggt gaa att gga gca agg ctt ata ttt taa<br>Tyr Phe Gly Gly Glu Ile Gly Ala Arg Leu Ile Phe<br>290               295               300 | 903 | |

<210> SEQ ID NO 50
<211> LENGTH: 300
<212> TYPE: PRT
<213> ORGANISM: OMP-1Z

<400> SEQUENCE: 50

-continued

```
Met Lys Lys Lys Asn Gln Phe Ile Thr Ile Ser Thr Ile Leu Val Cys
 1               5                  10                  15

Leu Leu Ser Leu Ser Asn Ala Ser Leu Ser Asn Thr Thr Asn Ser Ser
             20                  25                  30

Thr Lys Lys Gln Phe Gly Leu Tyr Val Ser Gly Gln Tyr Lys Pro Ser
         35                  40                  45

Val Ser Ile Phe Ser Asn Phe Ser Val Lys Glu Thr Asn Phe Pro Thr
     50                  55                  60

Lys Tyr Leu Ala Ala Leu Lys Lys Asp Ile Asn Ser Val Glu Phe Asp
 65                  70                  75                  80

Asp Ser Val Thr Ala Gly Ile Ser Tyr Pro Leu Asn Phe Ser Thr Pro
                 85                  90                  95

Tyr Ile Ala Val Phe Gln Asp Asn Ile Ser Asn Phe Asn Gly Ala Ile
                100                 105                 110

Gly Tyr Thr Phe Val Glu Gly Pro Arg Ile Glu Ile Glu Gly Ser Tyr
            115                 120                 125

Glu Glu Phe Asp Val Lys Asp Leu Glu Asp Ile Gln Lys Tyr Lys Met
130                 135                 140

His Thr Val Asp Phe Ala Leu Ala Arg Asp Ile Asp Ser Ile Pro Thr
145                 150                 155                 160

Ser Pro Lys Asn Arg Thr Ser His Asp Gly Asn Ser Ser Tyr Lys Val
                165                 170                 175

Tyr His Thr Val Met Lys Asn Glu Gly Leu Ser Ile Ile Ser Ile Met
                180                 185                 190

Val Asn Gly Cys Tyr Asp Phe Ser Asp Asn Leu Ser Ile Leu Pro
            195                 200                 205

Tyr Val Cys Gly Gly Ile Gly Val Asn Ala Ile Glu Phe Phe Asp Ala
        210                 215                 220

Leu His Val Lys Phe Ala Cys Gln Gly Lys Leu Gly Ile Thr Tyr Pro
225                 230                 235                 240

Leu Ser Ser Asn Val Ser Leu Phe Ala Gly Gly Tyr Tyr His Gln Val
                245                 250                 255

Met Gly Asn Gln Phe Lys Asn Leu Asn Val Gln His Val Ala Glu Leu
            260                 265                 270

Asn Asp Ala Pro Lys Val Thr Ser Ala Val Ala Thr Leu Asp Ile Gly
        275                 280                 285

Tyr Phe Gly Gly Glu Ile Gly Ala Arg Leu Ile Phe
    290                 295                 300
```

<210> SEQ ID NO 51
<211> LENGTH: 897
<212> TYPE: DNA
<213> ORGANISM: OMP-1H
<220> FEATURE:
<221> NAME/KEY: CDS
<222> LOCATION: (1)..(897)

<400> SEQUENCE: 51

```
atg aat cac aaa agt atg ctc ttt aca ata ggt aca gct ttg ata tcc    48
Met Asn His Lys Ser Met Leu Phe Thr Ile Gly Thr Ala Leu Ile Ser
 1               5                  10                  15 tta ttg tca tta cct aat gta tca ttc tca gga atc ata aat aac aat    96
Leu Leu Ser Leu Pro Asn Val Ser Phe Ser Gly Ile Ile Asn Asn Asn
             20                  25                  30 gct aac aat tta ggt ata tac att agt ggg caa tat aaa ccc agt gtt   144
Ala Asn Asn Leu Gly Ile Tyr Ile Ser Gly Gln Tyr Lys Pro Ser Val
```

```
                35                  40                  45
tct gtt ttt agc aat ttc tca gta aaa gaa act aac ttc act aca caa         192
Ser Val Phe Ser Asn Phe Ser Val Lys Glu Thr Asn Phe Thr Thr Gln
    50                  55                  60 cag tta gta gca ctt aaa aaa gat att gat tct gtt gac att agt acc         240
Gln Leu Val Ala Leu Lys Lys Asp Ile Asp Ser Val Asp Ile Ser Thr
65                  70                  75                  80 aat gct gat agc ggt att aat aat ccg cag aat ttc act atc cct tat         288
Asn Ala Asp Ser Gly Ile Asn Asn Pro Gln Asn Phe Thr Ile Pro Tyr
                85                  90                  95 ata cca aaa ttt caa gac aat gct gct agt ttt agt gga gca ctt gga         336
Ile Pro Lys Phe Gln Asp Asn Ala Ala Ser Phe Ser Gly Ala Leu Gly
            100                 105                 110 ttc ttc tac gct aga ggt tta aga ctt gaa atg gaa ggt tcc tat gaa         384
Phe Phe Tyr Ala Arg Gly Leu Arg Leu Glu Met Glu Gly Ser Tyr Glu
        115                 120                 125 gaa ttt gat gtt aaa aac cct gga gga tat aca aaa gta aaa gat gca         432
Glu Phe Asp Val Lys Asn Pro Gly Gly Tyr Thr Lys Val Lys Asp Ala
    130                 135                 140 tat cgt tac ttt gcc ctg gca cgt gag atg caa tct ggt caa act tgc         480
Tyr Arg Tyr Phe Ala Leu Ala Arg Glu Met Gln Ser Gly Gln Thr Cys
145                 150                 155                 160 cct aaa cac aaa gaa aca tca ggt att caa cct cac ggt att tat cac         528
Pro Lys His Lys Glu Thr Ser Gly Ile Gln Pro His Gly Ile Tyr His
                165                 170                 175 act gtt atg agg aat gat ggg gta tct att tca tct gtc ata atc aat         576
Thr Val Met Arg Asn Asp Gly Val Ser Ile Ser Ser Val Ile Ile Asn
            180                 185                 190 ggt tgt tat aac ttt act tta agt aat cta cca ata tca cct tac atg         624
Gly Cys Tyr Asn Phe Thr Leu Ser Asn Leu Pro Ile Ser Pro Tyr Met
        195                 200                 205 tgt gta ggt atg gga ata gat gct ata caa ttt ttt gat tca cta cat         672
Cys Val Gly Met Gly Ile Asp Ala Ile Gln Phe Phe Asp Ser Leu His
    210                 215                 220 att aag ttt gca cat caa agt aag tta ggt att act tac cca cta tct         720
Ile Lys Phe Ala His Gln Ser Lys Leu Gly Ile Thr Tyr Pro Leu Ser
225                 230                 235                 240 tca aat gtt cat tta ttt gct gat agc tat tat cat aaa gta ata ggt         768
Ser Asn Val His Leu Phe Ala Asp Ser Tyr Tyr His Lys Val Ile Gly
                245                 250                 255 aat aaa ttt aaa aat cta agg gtt caa cac gtt tat gaa tta caa cag         816
Asn Lys Phe Lys Asn Leu Arg Val Gln His Val Tyr Glu Leu Gln Gln
            260                 265                 270 gta cct aaa gtt aca tct gct gtt gct aca ctt gat att ggg tat ttt         864
Val Pro Lys Val Thr Ser Ala Val Ala Thr Leu Asp Ile Gly Tyr Phe
        275                 280                 285 ggt ggt gaa gtt gga gta agg ttt ata ctt taa                             897
Gly Gly Glu Val Gly Val Arg Phe Ile Leu
    290                 295
```

<210> SEQ ID NO 52
<211> LENGTH: 298
<212> TYPE: PRT
<213> ORGANISM: OMP-1H

<400> SEQUENCE: 52

```
Met Asn His Lys Ser Met Leu Phe Thr Ile Gly Thr Ala Leu Ile Ser
1               5                   10                  15

Leu Leu Ser Leu Pro Asn Val Ser Phe Ser Gly Ile Ile Asn Asn Asn
            20                  25                  30
```

```
Ala Asn Asn Leu Gly Ile Tyr Ile Ser Gly Gln Tyr Lys Pro Ser Val
         35                  40                  45

Ser Val Phe Ser Asn Phe Ser Val Lys Glu Thr Asn Phe Thr Thr Gln
 50                  55                  60

Gln Leu Val Ala Leu Lys Lys Asp Ile Asp Ser Val Asp Ile Ser Thr
 65                  70                  75                  80

Asn Ala Asp Ser Gly Ile Asn Asn Pro Gln Asn Phe Thr Ile Pro Tyr
                 85                  90                  95

Ile Pro Lys Phe Gln Asp Asn Ala Ala Ser Phe Ser Gly Ala Leu Gly
                100                 105                 110

Phe Phe Tyr Ala Arg Gly Leu Arg Leu Glu Met Glu Gly Ser Tyr Glu
            115                 120                 125

Glu Phe Asp Val Lys Asn Pro Gly Gly Tyr Thr Lys Val Lys Asp Ala
        130                 135                 140

Tyr Arg Tyr Phe Ala Leu Ala Arg Glu Met Gln Ser Gly Gln Thr Cys
145                 150                 155                 160

Pro Lys His Lys Glu Thr Ser Gly Ile Gln Pro His Gly Ile Tyr His
                165                 170                 175

Thr Val Met Arg Asn Asp Gly Val Ser Ile Ser Ser Val Ile Ile Asn
                180                 185                 190

Gly Cys Tyr Asn Phe Thr Leu Ser Asn Leu Pro Ile Ser Pro Tyr Met
            195                 200                 205

Cys Val Gly Met Gly Ile Asp Ala Ile Gln Phe Phe Asp Ser Leu His
        210                 215                 220

Ile Lys Phe Ala His Gln Ser Lys Leu Gly Ile Thr Tyr Pro Leu Ser
225                 230                 235                 240

Ser Asn Val His Leu Phe Ala Asp Ser Tyr Tyr His Lys Val Ile Gly
                245                 250                 255

Asn Lys Phe Lys Asn Leu Arg Val Gln His Val Tyr Glu Leu Gln Gln
                260                 265                 270

Val Pro Lys Val Thr Ser Ala Val Ala Thr Leu Asp Ile Gly Tyr Phe
            275                 280                 285

Gly Gly Glu Val Gly Val Arg Phe Ile Leu
        290                 295

<210> SEQ ID NO 53
<211> LENGTH: 882
<212> TYPE: DNA
<213> ORGANISM: p30-6
<220> FEATURE:
<221> NAME/KEY: CDS
<222> LOCATION: (1)..(882)

<400> SEQUENCE: 53 atg gca aat ttt atg tac aaa aaa tac aaa cta atg aca gca ggt gta      48
Met Ala Asn Phe Met Tyr Lys Lys Tyr Lys Leu Met Thr Ala Gly Val
 1               5                  10                  15 gta tta ttt cac atg tta ttt cta cct cat gtt tct ttc gca aaa aat      96
Val Leu Phe His Met Leu Phe Leu Pro His Val Ser Phe Ala Lys Asn
             20                  25                  30 aca aac agc aat aaa ctt gga tta tac atc agt gga cag tat aac cct     144
Thr Asn Ser Asn Lys Leu Gly Leu Tyr Ile Ser Gly Gln Tyr Asn Pro
         35                  40                  45 agt gtt tct gtt ttt agc aat ttt tca gca aaa gaa acc aat gtt cat     192
Ser Val Ser Val Phe Ser Asn Phe Ser Ala Lys Glu Thr Asn Val His
 50                  55                  60
```

```
aca gta caa ctc atg gcg ctt aaa aaa gac att gat tct att gaa gtt      240
Thr Val Gln Leu Met Ala Leu Lys Lys Asp Ile Asp Ser Ile Glu Val
 65              70                  75                  80 gat act gga aat agc gca ggt att agc aaa cca caa aat ttc aca gtt      288
Asp Thr Gly Asn Ser Ala Gly Ile Ser Lys Pro Gln Asn Phe Thr Val
                 85                  90                  95 ctt tat act cca aaa ttt caa gat aat gtt gct ggt ctt agc ggt gca      336
Leu Tyr Thr Pro Lys Phe Gln Asp Asn Val Ala Gly Leu Ser Gly Ala
            100                 105                 110 ctt gga ttc ttt tat tct aaa gga tta agg att gaa atg ggg ttt tct      384
Leu Gly Phe Phe Tyr Ser Lys Gly Leu Arg Ile Glu Met Gly Phe Ser
        115                 120                 125 tat gaa aaa ttt gat gct aaa gac ctt ggt gag tac acc aaa ata aaa      432
Tyr Glu Lys Phe Asp Ala Lys Asp Leu Gly Glu Tyr Thr Lys Ile Lys
130                 135                 140 gat gct tat aga tat ttt gct cta gta cgt gaa atg cat gtt agt ctc      480
Asp Ala Tyr Arg Tyr Phe Ala Leu Val Arg Glu Met His Val Ser Leu
145                 150                 155                 160 att tat cca aaa gat aat aac aca gga aca cat tat act gtt atg aga      528
Ile Tyr Pro Lys Asp Asn Asn Thr Gly Thr His Tyr Thr Val Met Arg
                165                 170                 175 aat gat ggt ata tct att tct tct gct aca gta aat ggc tgc tat gat      576
Asn Asp Gly Ile Ser Ile Ser Ser Ala Thr Val Asn Gly Cys Tyr Asp
            180                 185                 190 tct ttt ttc cag ttt atc ttt gtc acc tat atg tgt ata ggc atc ggt      624
Ser Phe Phe Gln Phe Ile Phe Val Thr Tyr Met Cys Ile Gly Ile Gly
        195                 200                 205 ata gat gct ata gaa ttt ctt aat gca tac ata tta agt ttg ctt gcc      672
Ile Asp Ala Ile Glu Phe Leu Asn Ala Tyr Ile Leu Ser Leu Leu Ala
210                 215                 220 aag gta gtt aag gtg tta act tat tct gta tct ccc aat gtt aat tta      720
Lys Val Val Lys Val Leu Thr Tyr Ser Val Ser Pro Asn Val Asn Leu
225                 230                 235                 240 ttt gca gat gga tat tat cat aaa gtg atg ggc aat aaa ttt aaa aat      768
Phe Ala Asp Gly Tyr Tyr His Lys Val Met Gly Asn Lys Phe Lys Asn
                245                 250                 255 tta cct gtt caa tac gtt aat act tta gaa gag tat cca aga gtt aca      816
Leu Pro Val Gln Tyr Val Asn Thr Leu Glu Glu Tyr Pro Arg Val Thr
            260                 265                 270 tct gca att gct aca ctt gat att ggc tac ctc ggt ggt gaa att ggc      864
Ser Ala Ile Ala Thr Leu Asp Ile Gly Tyr Leu Gly Gly Glu Ile Gly
        275                 280                 285 ata aga ttt ata ttt taa                                              882
Ile Arg Phe Ile Phe
    290

<210> SEQ ID NO 54
<211> LENGTH: 293
<212> TYPE: PRT
<213> ORGANISM: p30-6

<400> SEQUENCE: 54

Met Ala Asn Phe Met Tyr Lys Lys Tyr Lys Leu Met Thr Ala Gly Val
 1               5                  10                  15

Val Leu Phe His Met Leu Phe Leu Pro His Val Ser Phe Ala Lys Asn
                20                  25                  30

Thr Asn Ser Asn Lys Leu Gly Leu Tyr Ile Ser Gly Gln Tyr Asn Pro
            35                  40                  45

Ser Val Ser Val Phe Ser Asn Phe Ser Ala Lys Glu Thr Asn Val His
        50                  55                  60
```

-continued

```
Thr Val Gln Leu Met Ala Leu Lys Lys Asp Ile Asp Ser Ile Glu Val
 65                  70                  75                  80

Asp Thr Gly Asn Ser Ala Gly Ile Ser Lys Pro Gln Asn Phe Thr Val
                 85                  90                  95

Leu Tyr Thr Pro Lys Phe Gln Asp Asn Val Ala Gly Leu Ser Gly Ala
            100                 105                 110

Leu Gly Phe Phe Tyr Ser Lys Gly Leu Arg Ile Glu Met Gly Phe Ser
        115                 120                 125

Tyr Glu Lys Phe Asp Ala Lys Asp Leu Gly Glu Tyr Thr Lys Ile Lys
130                 135                 140

Asp Ala Tyr Arg Tyr Phe Ala Leu Val Arg Glu Met His Val Ser Leu
145                 150                 155                 160

Ile Tyr Pro Lys Asp Asn Thr Gly Thr His Tyr Thr Val Met Arg
                165                 170                 175

Asn Asp Gly Ile Ser Ile Ser Ser Ala Thr Val Asn Gly Cys Tyr Asp
                180                 185                 190

Ser Phe Phe Gln Phe Ile Phe Val Thr Tyr Met Cys Ile Gly Ile Gly
        195                 200                 205

Ile Asp Ala Ile Glu Phe Leu Asn Ala Tyr Ile Leu Ser Leu Leu Ala
210                 215                 220

Lys Val Val Lys Val Leu Thr Tyr Ser Val Ser Pro Asn Val Asn Leu
225                 230                 235                 240

Phe Ala Asp Gly Tyr Tyr His Lys Val Met Gly Asn Lys Phe Lys Asn
                245                 250                 255

Leu Pro Val Gln Tyr Val Asn Thr Leu Glu Glu Tyr Pro Arg Val Thr
            260                 265                 270

Ser Ala Ile Ala Thr Leu Asp Ile Gly Tyr Leu Gly Gly Glu Ile Gly
        275                 280                 285

Ile Arg Phe Ile Phe
    290
```

<210> SEQ ID NO 55
<211> LENGTH: 891
<212> TYPE: DNA
<213> ORGANISM: p30-7
<220> FEATURE:
<221> NAME/KEY: CDS
<222> LOCATION: (1)..(891)

<400> SEQUENCE: 55

```
atg gga aat tct atg aat aat aaa agt caa ttc tta ata aga ttt ata     48
Met Gly Asn Ser Met Asn Asn Lys Ser Gln Phe Leu Ile Arg Phe Ile
  1               5                  10                  15 ttt tta aca tgc atg ctg tca tta cct aat ata tct ctt tca aaa gta     96
Phe Leu Thr Cys Met Leu Ser Leu Pro Asn Ile Ser Leu Ser Lys Val
             20                  25                  30 aat aac gaa aaa cat tct ggt ttg tat att agc ggg caa tac aaa ccc    144
Asn Asn Glu Lys His Ser Gly Leu Tyr Ile Ser Gly Gln Tyr Lys Pro
         35                  40                  45 agt gtt tct gtt ttc agt aat ttt tca gtt aaa gaa acc aac ttt cat    192
Ser Val Ser Val Phe Ser Asn Phe Ser Val Lys Glu Thr Asn Phe His
     50                  55                  60 aca aaa cat ctc ata gct ctt aaa caa gat gtt gat tct gtt gaa att    240
Thr Lys His Leu Ile Ala Leu Lys Gln Asp Val Asp Ser Val Glu Ile
 65                  70                  75                  80 gat act ggt agt aat aca gca ggt att agt aac cca tct aac ttt aca    288
Asp Thr Gly Ser Asn Thr Ala Gly Ile Ser Asn Pro Ser Asn Phe Thr
```

-continued

```
atc cct tat act gca gaa ttt caa gac aac cat act aac tgc aat ggc    336
Ile Pro Tyr Thr Ala Glu Phe Gln Asp Asn His Thr Asn Cys Asn Gly
        100                 105                 110 tct att ggt tat gct ttt gct gaa ggt cca aga att gaa ata gaa tta    384
Ser Ile Gly Tyr Ala Phe Ala Glu Gly Pro Arg Ile Glu Ile Glu Leu
    115                 120                 125 tca tat gaa aaa ttt gat gta aaa aat ccc aca ggg tat act aca gta    432
Ser Tyr Glu Lys Phe Asp Val Lys Asn Pro Thr Gly Tyr Thr Thr Val
130                 135                 140 aaa gat gct tat aga tac ttt gct tta gca cgt gaa ata aat att tct    480
Lys Asp Ala Tyr Arg Tyr Phe Ala Leu Ala Arg Glu Ile Asn Ile Ser
145                 150                 155                 160 cta ttc caa cca aaa caa aaa gaa ggt agt gga att tac cat gtc gta    528
Leu Phe Gln Pro Lys Gln Lys Glu Gly Ser Gly Ile Tyr His Val Val
                165                 170                 175 atg aaa aac gat ggg tta tct atc tta tcc aat ata gtt aat att tgc    576
Met Lys Asn Asp Gly Leu Ser Ile Leu Ser Asn Ile Val Asn Ile Cys
            180                 185                 190 tac gat ttt tct tta aat aat tta cct ata tca cct tat tta tgc gga    624
Tyr Asp Phe Ser Leu Asn Asn Leu Pro Ile Ser Pro Tyr Leu Cys Gly
        195                 200                 205 gga atg ggt ata aat gcc ata gaa ttc ttt gac gct tta cat gtg aaa    672
Gly Met Gly Ile Asn Ala Ile Glu Phe Phe Asp Ala Leu His Val Lys
    210                 215                 220 ttt gct tat caa agc aag gca gga att agt tat caa cta tta cgt aaa    720
Phe Ala Tyr Gln Ser Lys Ala Gly Ile Ser Tyr Gln Leu Leu Arg Lys
225                 230                 235                 240 atc aac tta ttt att gat gta tat tac tac gaa gta ata agt aat aaa    768
Ile Asn Leu Phe Ile Asp Val Tyr Tyr Tyr Glu Val Ile Ser Asn Lys
                245                 250                 255 ttt aaa aac ctg aaa gtc caa cat gta cat gaa ctt aaa gat aat cca    816
Phe Lys Asn Leu Lys Val Gln His Val His Glu Leu Lys Asp Asn Pro
            260                 265                 270 aaa gtc aca tct gca gtt gct aca ctt gat ata gca tat ttt ggt agt    864
Lys Val Thr Ser Ala Val Ala Thr Leu Asp Ile Ala Tyr Phe Gly Ser
        275                 280                 285 gaa gct ggc ata aga att ata ttt taa                                891
Glu Ala Gly Ile Arg Ile Ile Phe
    290                 295
```

<210> SEQ ID NO 56
<211> LENGTH: 296
<212> TYPE: PRT
<213> ORGANISM: p30-7

<400> SEQUENCE: 56

```
Met Gly Asn Ser Met Asn Asn Lys Ser Gln Phe Leu Ile Arg Phe Ile
1               5                   10                  15

Phe Leu Thr Cys Met Leu Ser Leu Pro Asn Ile Ser Leu Ser Lys Val
            20                  25                  30

Asn Asn Glu Lys His Ser Gly Leu Tyr Ile Ser Gly Gln Tyr Lys Pro
        35                  40                  45

Ser Val Ser Val Phe Ser Asn Phe Ser Val Lys Glu Thr Asn Phe His
    50                  55                  60

Thr Lys His Leu Ile Ala Leu Lys Gln Asp Val Asp Ser Val Glu Ile
65                  70                  75                  80

Asp Thr Gly Ser Asn Thr Ala Gly Ile Ser Asn Pro Ser Asn Phe Thr
                85                  90                  95
```

-continued

```
Ile Pro Tyr Thr Ala Glu Phe Gln Asp Asn His Thr Asn Cys Asn Gly
            100                 105                 110

Ser Ile Gly Tyr Ala Phe Ala Glu Gly Pro Arg Ile Glu Ile Glu Leu
        115                 120                 125

Ser Tyr Glu Lys Phe Asp Val Lys Asn Pro Thr Gly Tyr Thr Thr Val
    130                 135                 140

Lys Asp Ala Tyr Arg Tyr Phe Ala Leu Ala Arg Glu Ile Asn Ile Ser
145                 150                 155                 160

Leu Phe Gln Pro Lys Gln Lys Glu Gly Ser Gly Ile Tyr His Val Val
                165                 170                 175

Met Lys Asn Asp Gly Leu Ser Ile Leu Ser Asn Ile Val Asn Ile Cys
            180                 185                 190

Tyr Asp Phe Ser Leu Asn Asn Leu Pro Ile Ser Pro Tyr Leu Cys Gly
        195                 200                 205

Gly Met Gly Ile Asn Ala Ile Glu Phe Phe Asp Ala Leu His Val Lys
    210                 215                 220

Phe Ala Tyr Gln Ser Lys Ala Gly Ile Ser Tyr Gln Leu Leu Arg Lys
225                 230                 235                 240

Ile Asn Leu Phe Ile Asp Val Tyr Tyr Glu Val Ile Ser Asn Lys
                245                 250                 255

Phe Lys Asn Leu Lys Val Gln His Val His Glu Leu Lys Asp Asn Pro
            260                 265                 270

Lys Val Thr Ser Ala Val Ala Thr Leu Asp Ile Ala Tyr Phe Gly Ser
        275                 280                 285

Glu Ala Gly Ile Arg Ile Phe
    290                 295
```

```
<210> SEQ ID NO 57
<211> LENGTH: 846
<212> TYPE: DNA
<213> ORGANISM: p30-9
<220> FEATURE:
<221> NAME/KEY: CDS
<222> LOCATION: (1)..(846)

<400> SEQUENCE: 57
```

```
atg aat aat aaa aga aat ttt ttt tta ata ggt atg tct cta ttg ata    48
Met Asn Asn Lys Arg Asn Phe Phe Leu Ile Gly Met Ser Leu Leu Ile
 1               5                  10                  15 aat cta cta ttg cca att gat gcc tct tct atg gaa gta cat aat tat    96
Asn Leu Leu Leu Pro Ile Asp Ala Ser Ser Met Glu Val His Asn Tyr
             20                  25                  30 aca cat ttt aca cct agg ctg tat att agt ggg caa tac agg cca gga   144
Thr His Phe Thr Pro Arg Leu Tyr Ile Ser Gly Gln Tyr Arg Pro Gly
         35                  40                  45 gtt tcc cac ttt agc aaa ttt tca gtc aaa gaa aca cat tgt aat act   192
Val Ser His Phe Ser Lys Phe Ser Val Lys Glu Thr His Cys Asn Thr
     50                  55                  60 gtg caa tta gtt ggg cta aca aaa gat ata aaa gta act aat aac agt   240
Val Gln Leu Val Gly Leu Thr Lys Asp Ile Lys Val Thr Asn Asn Ser
 65                  70                  75                  80 agt atc aac aca aat act agt ttt aac ttt cct tat gtt gca gaa ttt   288
Ser Ile Asn Thr Asn Thr Ser Phe Asn Phe Pro Tyr Val Ala Glu Phe
                 85                  90                  95 caa gat aac gca atg agc ttt agt gga gca ata gga tgc ttt tat tca   336
Gln Asp Asn Ala Met Ser Phe Ser Gly Ala Ile Gly Cys Phe Tyr Ser
            100                 105                 110
```

| | | |
|---|---|---|
| gaa cac ttc aga att gaa gta gaa gct tct tat gaa gaa ttt gac gtt<br>Glu His Phe Arg Ile Glu Val Glu Ala Ser Tyr Glu Glu Phe Asp Val<br>     115                   120                  125 | | 384 |
| aaa aat cct gaa gga tct act aca gac tcc tat aga tat ttc gcg tta<br>Lys Asn Pro Glu Gly Ser Thr Thr Asp Ser Tyr Arg Tyr Phe Ala Leu<br>130                   135                  140 | | 432 |
| gca cgt ggc atg gat ggt aat aat att cct aca agt caa aaa ttt act<br>Ala Arg Gly Met Asp Gly Asn Asn Ile Pro Thr Ser Gln Lys Phe Thr<br>145                   150                  155                  160 | | 480 |
| gta atg aga aac gac ggg tta tta atc tca tct gtt atg ata aat ggc<br>Val Met Arg Asn Asp Gly Leu Leu Ile Ser Ser Val Met Ile Asn Gly<br>               165                  170                  175 | | 528 |
| tgt tac aat gtc ata cta aat gat ata caa gca gaa cct tac ata tgt<br>Cys Tyr Asn Val Ile Leu Asn Asp Ile Gln Ala Glu Pro Tyr Ile Cys<br>                  180                  185                  190 | | 576 |
| gca gga cta gga gga gat ttt ata gaa ttc ttc aat ggc ttt cat gtt<br>Ala Gly Leu Gly Gly Asp Phe Ile Glu Phe Phe Asn Gly Phe His Val<br>               195                  200                  205 | | 624 |
| aag cta gct tat caa ggt aaa gta ggc att agt tat caa ata ttc cct<br>Lys Leu Ala Tyr Gln Gly Lys Val Gly Ile Ser Tyr Gln Ile Phe Pro<br>210                   215                  220 | | 672 |
| gaa gta aga tta ttt att gat gga tac tac cat aaa gta aaa ggc aac<br>Glu Val Arg Leu Phe Ile Asp Gly Tyr Tyr His Lys Val Lys Gly Asn<br>225                   230                  235                  240 | | 720 |
| aag ttt aaa aat tta cac gtt caa cat gta ggt gca ctt gca gca ctc<br>Lys Phe Lys Asn Leu His Val Gln His Val Gly Ala Leu Ala Ala Leu<br>               245                  250                  255 | | 768 |
| cct aaa gtt aca tct gca gtt gca aca ctt aat att gga tac ttt ggt<br>Pro Lys Val Thr Ser Ala Val Ala Thr Leu Asn Ile Gly Tyr Phe Gly<br>260                   265                  270 | | 816 |
| tgt gaa gct gga gta aga ttc ata ttt taa<br>Cys Glu Ala Gly Val Arg Phe Ile Phe<br>275                   280 | | 846 |

<210> SEQ ID NO 58
<211> LENGTH: 281
<212> TYPE: PRT
<213> ORGANISM: p30-9

<400> SEQUENCE: 58

Met Asn Asn Lys Arg Asn Phe Phe Leu Ile Gly Met Ser Leu Leu Ile
1                  5                  10                 15

Asn Leu Leu Leu Pro Ile Asp Ala Ser Ser Met Glu Val His Asn Tyr
              20                  25                  30

Thr His Phe Thr Pro Arg Leu Tyr Ile Ser Gly Gln Tyr Arg Pro Gly
            35                  40                  45

Val Ser His Phe Ser Lys Phe Ser Val Lys Glu Thr His Cys Asn Thr
    50                  55                  60

Val Gln Leu Val Gly Leu Thr Lys Asp Ile Lys Val Thr Asn Asn Ser
65                  70                  75                  80

Ser Ile Asn Thr Asn Thr Ser Phe Asn Phe Pro Tyr Val Ala Glu Phe
              85                  90                  95

Gln Asp Asn Ala Met Ser Phe Ser Gly Ala Ile Gly Cys Phe Tyr Ser
            100                 105               110

Glu His Phe Arg Ile Glu Val Glu Ala Ser Tyr Glu Glu Phe Asp Val
            115                 120               125

Lys Asn Pro Glu Gly Ser Thr Thr Asp Ser Tyr Arg Tyr Phe Ala Leu
130                   135                  140

-continued

```
Ala Arg Gly Met Asp Gly Asn Asn Ile Pro Thr Ser Gln Lys Phe Thr
145                 150                 155                 160

Val Met Arg Asn Asp Gly Leu Leu Ile Ser Ser Val Met Ile Asn Gly
            165                 170                 175

Cys Tyr Asn Val Ile Leu Asn Asp Ile Gln Ala Glu Pro Tyr Ile Cys
        180                 185                 190

Ala Gly Leu Gly Gly Asp Phe Ile Glu Phe Phe Asn Gly Phe His Val
        195                 200                 205

Lys Leu Ala Tyr Gln Gly Lys Val Gly Ile Ser Tyr Gln Ile Phe Pro
        210                 215                 220

Glu Val Arg Leu Phe Ile Asp Gly Tyr Tyr His Lys Val Lys Gly Asn
225                 230                 235                 240

Lys Phe Lys Asn Leu His Val Gln His Val Gly Ala Leu Ala Ala Leu
            245                 250                 255

Pro Lys Val Thr Ser Ala Val Ala Thr Leu Asn Ile Gly Tyr Phe Gly
            260                 265                 270

Cys Glu Ala Gly Val Arg Phe Ile Phe
        275                 280
```

<210> SEQ ID NO 59
<211> LENGTH: 840
<212> TYPE: DNA
<213> ORGANISM: p30-11
<220> FEATURE:
<221> NAME/KEY: CDS
<222> LOCATION: (1)..(840)

<400> SEQUENCE: 59

```
atg aac aaa aag aaa att att aca gta gga aca aca tta gct tat tta      48
Met Asn Lys Lys Lys Ile Ile Thr Val Gly Thr Thr Leu Ala Tyr Leu
1               5                   10                  15 tta tta tca cct aac ata tct ttt tca gaa gta atc aac aat gat act      96
Leu Leu Ser Pro Asn Ile Ser Phe Ser Glu Val Ile Asn Asn Asp Thr
            20                  25                  30 gat aaa tat tct aga cta tat ata agt gga caa tat aaa cca gga ttt     144
Asp Lys Tyr Ser Arg Leu Tyr Ile Ser Gly Gln Tyr Lys Pro Gly Phe
        35                  40                  45 tct tat ttt aat aag ttc tca gtt aga gaa act gat cat ttc act aaa     192
Ser Tyr Phe Asn Lys Phe Ser Val Arg Glu Thr Asp His Phe Thr Lys
50                  55                  60 gca tta ata gga tta aga cat gac gca ata tct act aaa aat tta aca     240
Ala Leu Ile Gly Leu Arg His Asp Ala Ile Ser Thr Lys Asn Leu Thr
65                  70                  75                  80 act aat aca gat ttc aat act ctt tat aaa gta aca ttt caa aac aac     288
Thr Asn Thr Asp Phe Asn Thr Leu Tyr Lys Val Thr Phe Gln Asn Asn
                85                  90                  95 atc att agc ttt agc ggt gct att ggt tat tct gat agc aca ggt gta     336
Ile Ile Ser Phe Ser Gly Ala Ile Gly Tyr Ser Asp Ser Thr Gly Val
            100                 105                 110 agg ttt gag cta gaa ggc tct tat gaa gag ttc gat gtt aca gac cct     384
Arg Phe Glu Leu Glu Gly Ser Tyr Glu Glu Phe Asp Val Thr Asp Pro
        115                 120                 125 gga gat tgt ata ata aaa gat act tac agg tac ttt gca tta gct aga     432
Gly Asp Cys Ile Ile Lys Asp Thr Tyr Arg Tyr Phe Ala Leu Ala Arg
    130                 135                 140 aaa aca agt ggt aat cat ccc aac gat aat ggg gaa tat act gtc atg     480
Lys Thr Ser Gly Asn His Pro Asn Asp Asn Gly Glu Tyr Thr Val Met
145                 150                 155                 160 aga aat gat gga gta tcc att acc tcc gtt ata ttc aat ggt tgt tat     528
```

```
                                                                                              -continued Arg Asn Asp Gly Val Ser Ile Thr Ser Val Ile Phe Asn Gly Cys Tyr
                165                 170                 175 gat ctc tct tta aaa gag cta gaa ata tca cca tat gtt tgc att ggt        576
Asp Leu Ser Leu Lys Glu Leu Glu Ile Ser Pro Tyr Val Cys Ile Gly
            180                 185                 190 atc gga gga gac ttt ata gaa ttt ttt gat gct tta cac att aaa tta        624
Ile Gly Gly Asp Phe Ile Glu Phe Phe Asp Ala Leu His Ile Lys Leu
        195                 200                 205 gca tat caa ggt aaa cta ggt att agc tat tct ttt tcc act aga aca        672
Ala Tyr Gln Gly Lys Leu Gly Ile Ser Tyr Ser Phe Ser Thr Arg Thr
    210                 215                 220 aat tta ttt atc gat tgt tat tac cat aga gtt ata ggt aat caa ttt        720
Asn Leu Phe Ile Asp Cys Tyr Tyr His Arg Val Ile Gly Asn Gln Phe
225                 230                 235                 240 aat aat tta aat gtt caa cat gta gtt gag ctt aca gaa gca cct aaa        768
Asn Asn Leu Asn Val Gln His Val Val Glu Leu Thr Glu Ala Pro Lys
                245                 250                 255 gct aca tct gca att gct aca ctt aat gtt agt tac ttc ggt gga gaa        816
Ala Thr Ser Ala Ile Ala Thr Leu Asn Val Ser Tyr Phe Gly Gly Glu
            260                 265                 270 gtt gga att aga ctt atg ttt taa                                        840
Val Gly Ile Arg Leu Met Phe
        275                 280

<210> SEQ ID NO 60
<211> LENGTH: 279
<212> TYPE: PRT
<213> ORGANISM: p30-11

<400> SEQUENCE: 60

Met Asn Lys Lys Ile Ile Thr Val Gly Thr Thr Leu Ala Tyr Leu
 1               5                  10                  15

Leu Leu Ser Pro Asn Ile Ser Phe Ser Glu Val Ile Asn Asn Asp Thr
            20                  25                  30

Asp Lys Tyr Ser Arg Leu Tyr Ile Ser Gly Gln Tyr Lys Pro Gly Phe
        35                  40                  45

Ser Tyr Phe Asn Lys Phe Ser Val Arg Glu Thr Asp His Phe Thr Lys
    50                  55                  60

Ala Leu Ile Gly Leu Arg His Asp Ala Ile Ser Thr Lys Asn Leu Thr
65                  70                  75                  80

Thr Asn Thr Asp Phe Asn Thr Leu Tyr Lys Val Thr Phe Gln Asn Asn
                85                  90                  95

Ile Ile Ser Phe Ser Gly Ala Ile Gly Tyr Ser Asp Ser Thr Gly Val
            100                 105                 110

Arg Phe Glu Leu Glu Gly Ser Tyr Glu Glu Phe Asp Val Thr Asp Pro
        115                 120                 125

Gly Asp Cys Ile Ile Lys Asp Thr Tyr Arg Tyr Phe Ala Leu Ala Arg
    130                 135                 140

Lys Thr Ser Gly Asn His Pro Asn Asp Asn Gly Glu Tyr Thr Val Met
145                 150                 155                 160

Arg Asn Asp Gly Val Ser Ile Thr Ser Val Ile Phe Asn Gly Cys Tyr
                165                 170                 175

Asp Leu Ser Leu Lys Glu Leu Glu Ile Ser Pro Tyr Val Cys Ile Gly
            180                 185                 190

Ile Gly Gly Asp Phe Ile Glu Phe Phe Asp Ala Leu His Ile Lys Leu
        195                 200                 205

Ala Tyr Gln Gly Lys Leu Gly Ile Ser Tyr Ser Phe Ser Thr Arg Thr
```

-continued

```
                210                 215                 220
Asn Leu Phe Ile Asp Cys Tyr Tyr His Arg Val Ile Gly Asn Gln Phe
225                 230                 235                 240

Asn Asn Leu Asn Val Gln His Val Val Glu Leu Thr Glu Ala Pro Lys
            245                 250                 255

Ala Thr Ser Ala Ile Ala Thr Leu Asn Val Ser Tyr Phe Gly Gly Glu
            260                 265                 270

Val Gly Ile Arg Leu Met Phe
        275

<210> SEQ ID NO 61
<211> LENGTH: 726
<212> TYPE: DNA
<213> ORGANISM: p30-12
<220> FEATURE:
<221> NAME/KEY: CDS
<222> LOCATION: (1)..(726)

<400> SEQUENCE: 61 ccc gtc gtt tct cat tac agt gac ttt tca att aaa gaa act tat act      48
Pro Val Val Ser His Tyr Ser Asp Phe Ser Ile Lys Glu Thr Tyr Thr
 1               5                  10                  15 aac act gag gca ttg ttt ggg cta aaa caa gat att agt tct att tta      96
Asn Thr Glu Ala Leu Phe Gly Leu Lys Gln Asp Ile Ser Ser Ile Leu
                20                  25                  30 cgt aat aaa gag acc aca caa tat aat aac aat ttt aac gtt ccc tat     144
Arg Asn Lys Glu Thr Thr Gln Tyr Asn Asn Asn Phe Asn Val Pro Tyr
            35                  40                  45 act gca aaa ttt caa gac gac ttt gcg agt ttc agc ata gct gtt gga     192
Thr Ala Lys Phe Gln Asp Asp Phe Ala Ser Phe Ser Ile Ala Val Gly
        50                  55                  60 tat att gct aac aat ggt cca aga att gaa ata gaa gga tct tac gaa     240
Tyr Ile Ala Asn Asn Gly Pro Arg Ile Glu Ile Glu Gly Ser Tyr Glu
 65                  70                  75                  80 gaa ttt gat gtt aaa aac cca gga aat tat aca aca ata gat gct cat     288
Glu Phe Asp Val Lys Asn Pro Gly Asn Tyr Thr Thr Ile Asp Ala His
                 85                  90                  95 agg tac att gct tta gct aga gaa aaa act tct tac tat cta agt tct     336
Arg Tyr Ile Ala Leu Ala Arg Glu Lys Thr Ser Tyr Tyr Leu Ser Ser
            100                 105                 110 cct aaa gaa aac aaa tat gta att ata aag aat aac ggc ata tct att     384
Pro Lys Glu Asn Lys Tyr Val Ile Ile Lys Asn Asn Gly Ile Ser Ile
        115                 120                 125 gta tct att ata att aat ggt tgt tat gat att tct tta aat gat tct     432
Val Ser Ile Ile Ile Asn Gly Cys Tyr Asp Ile Ser Leu Asn Asp Ser
130                 135                 140 aag gtg tca cct tac ata tgc aca ggg ttt ggt gga gat ttt ata gag     480
Lys Val Ser Pro Tyr Ile Cys Thr Gly Phe Gly Gly Asp Phe Ile Glu
145                 150                 155                 160 ttt ttt agt gct ata cgt ttt aag ttt gct tat caa ggt aaa ata ggt     528
Phe Phe Ser Ala Ile Arg Phe Lys Phe Ala Tyr Gln Gly Lys Ile Gly
                165                 170                 175 atc agt tat tca tta tct tct aac ata att tta ttt act gat gga tat     576
Ile Ser Tyr Ser Leu Ser Ser Asn Ile Ile Leu Phe Thr Asp Gly Tyr
            180                 185                 190 tac cac aag gta ata aat tcc caa ttt aaa aat tta aat gtt gaa cat     624
Tyr His Lys Val Ile Asn Ser Gln Phe Lys Asn Leu Asn Val Glu His
        195                 200                 205 gtt gtt aat gag tta act aca gat cct aaa gtg act tct gca aca gca     672
Val Val Asn Glu Leu Thr Thr Asp Pro Lys Val Thr Ser Ala Thr Ala
```

```
            210                 215                 220
ttt ctt aat att gag tat ttt ggt ggt gaa ttt gga tta aaa ttt ata     720
Phe Leu Asn Ile Glu Tyr Phe Gly Gly Glu Phe Gly Leu Lys Phe Ile
225                 230                 235                 240 ttt taa                                                             726
Phe
```

<210> SEQ ID NO 62
<211> LENGTH: 241
<212> TYPE: PRT
<213> ORGANISM: p30-12

<400> SEQUENCE: 62

```
Pro Val Ser His Tyr Ser Asp Phe Ser Ile Lys Glu Thr Tyr Thr
1               5                   10                  15

Asn Thr Glu Ala Leu Phe Gly Leu Lys Gln Asp Ile Ser Ser Ile Leu
                20                  25                  30

Arg Asn Lys Glu Thr Thr Gln Tyr Asn Asn Phe Asn Val Pro Tyr
            35                  40                  45

Thr Ala Lys Phe Gln Asp Asp Phe Ala Ser Phe Ser Ile Ala Val Gly
        50                  55                  60

Tyr Ile Ala Asn Asn Gly Pro Arg Ile Glu Ile Glu Gly Ser Tyr Glu
65                  70                  75                  80

Glu Phe Asp Val Lys Asn Pro Gly Asn Tyr Thr Thr Ile Asp Ala His
                85                  90                  95

Arg Tyr Ile Ala Leu Ala Arg Glu Lys Thr Ser Tyr Tyr Leu Ser Ser
            100                 105                 110

Pro Lys Glu Asn Lys Tyr Val Ile Ile Lys Asn Asn Gly Ile Ser Ile
        115                 120                 125

Val Ser Ile Ile Ile Asn Gly Cys Tyr Asp Ile Ser Leu Asn Asp Ser
130                 135                 140

Lys Val Ser Pro Tyr Ile Cys Thr Gly Phe Gly Gly Asp Phe Ile Glu
145                 150                 155                 160

Phe Phe Ser Ala Ile Arg Phe Lys Phe Ala Tyr Gln Gly Lys Ile Gly
                165                 170                 175

Ile Ser Tyr Ser Leu Ser Ser Asn Ile Ile Leu Phe Thr Asp Gly Tyr
            180                 185                 190

Tyr His Lys Val Ile Asn Ser Gln Phe Lys Asn Leu Asn Val Glu His
        195                 200                 205

Val Val Asn Glu Leu Thr Thr Asp Pro Lys Val Thr Ser Ala Thr Ala
210                 215                 220

Phe Leu Asn Ile Glu Tyr Phe Gly Gly Glu Phe Gly Leu Lys Phe Ile
225                 230                 235                 240

Phe
```

<210> SEQ ID NO 63
<211> LENGTH: 19
<212> TYPE: PRT
<213> ORGANISM: N-terminal of OMP-1 protein

<400> SEQUENCE: 63

```
Asp Pro Ala Gly Ser Gly Ile Asn Gly Asn Phe Tyr Ile Ser Gly Lys
1               5                   10                  15

Tyr Met Pro
```

<210> SEQ ID NO 64

```
<211> LENGTH: 45
<212> TYPE: DNA
<213> ORGANISM: FECH1

<400> SEQUENCE: 64
cgggatccga attcggatgc atatcaatcg gatgcaatct ttcta            45

<210> SEQ ID NO 65
<211> LENGTH: 36
<212> TYPE: DNA
<213> ORGANISM: RECH2

<400> SEQUENCE: 65
agcggccgct taagaatcac gagaactctt cgctcc                      36

<210> SEQ ID NO 66
<211> LENGTH: 20
<212> TYPE: DNA
<213> ORGANISM: REC1

<400> SEQUENCE: 66
acctaacttt ccttggtaag                                        20
```